Figure 1:
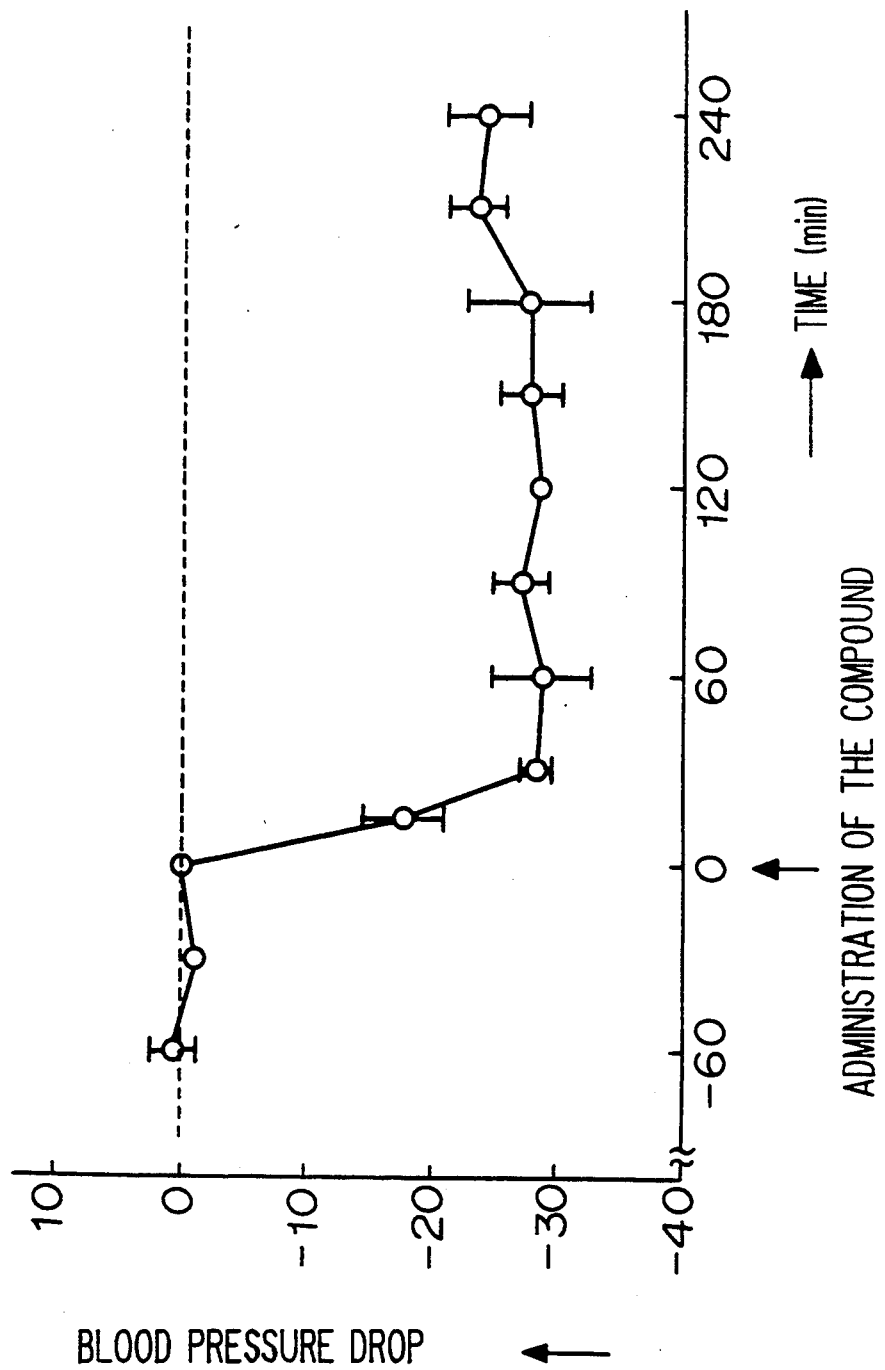

United States Patent [19]

Morishima et al.

[11] Patent Number: 5,424,309
[45] Date of Patent: Jun. 13, 1995

[54] N-SUBSTITUTED ACYLAMINO ACID COMPOUNDS, PROCESS FOR THEIR PRODUCTION AND THEIR USE

[75] Inventors: Hajime Morishima, Tokyo; Yutaka Kokie, Koshigaya; Masato Nakano, Ichikawa; Shugo Atsuumi; Seiichi Tanaka, both of Tokyo; Kenji Matsuyama, Kashiwa, all of Japan

[73] Assignee: Banyu Pharmaceutical Co., Ltd., Tokyo, Japan

[21] Appl. No.: 200,536

[22] Filed: Feb. 22, 1994

Related U.S. Application Data

[63] Continuation of Ser. No. 818,474, Jan. 6, 1992, abandoned, which is a continuation of Ser. No. 446,113, Dec. 5, 1985, abandoned.

[30] Foreign Application Priority Data

Dec. 19, 1988 [JP] Japan ................ 63-320096
Mar. 20, 1989 [JP] Japan ................ 1-68921

[51] Int. Cl.$^6$ .................. A61K 31/535; C07D 265/30
[52] U.S. Cl. ................ 514/237.8; 514/238.8; 514/239.2; 514/227.5; 514/227.8; 514/255; 514/315; 514/317; 514/318; 514/336; 514/340; 514/396; 514/397; 514/399; 514/365; 514/406; 544/158; 544/159; 544/160; 544/161; 544/59; 544/60; 544/358; 544/359; 544/360; 546/184; 546/192; 546/268; 546/275; 548/146; 548/202; 548/203; 548/204; 548/311.1; 548/312.4; 548/314.7; 548/356.1; 548/364.1; 548/373.1
[58] Field of Search ............... 544/158, 159, 160, 161, 544/59, 60, 358, 359, 360; 514/237.8, 238.8, 239.2, 227.5, 227.8, 255, 315, 317, 318, 336, 340, 396, 397, 399, 365, 406; 546/184, 192, 268, 275; 548/146, 202, 203, 204, 311.1, 312.4, 314.7, 356.1, 364.1, 373.1

[56] References Cited

U.S. PATENT DOCUMENTS 4,851,387 7/1989 Koike et al. .
4,927,565 5/1990 Tanaka et al. .
5,122,523 6/1992 Morishima et al. .
5,240,924 8/1993 Morishima et al. .

FOREIGN PATENT DOCUMENTS 0206807 12/1986 European Pat. Off. .
0309766 5/1989 European Pat. Off. .

OTHER PUBLICATIONS

Plattner et al. J. Med. Chem., 31, 2277–2288 (1988).
Bolis et al. J. Med. Chem., 30, 1729–1737 (1987).
Haber et al., J. Cardiovascular Pharmacology, 10 (Suppl 7); 554–558 (1987).
Burger A., Medicinal Chemistry, 2nd Ed. 565–571, 578–581, 600–601 (1960).
Denkewalter et al., Progress in Drug Research, vol. 10, 510–512 (1966).

*Primary Examiner*—Mary C. Lee
*Assistant Examiner*—Joseph K. McKane
*Attorney, Agent, or Firm*—Oblon, Spivak, McClelland, Maier & Neustadt

[57] ABSTRACT

The present invention provides an N-substituted acylamino acid compound of the formula:

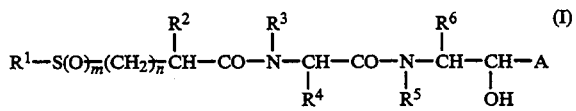

a process for their production and pharmaceutical uses, and intermediates useful for their production.

5 Claims, 1 Drawing Sheet

N-SUBSTITUTED ACYLAMINO ACID COMPOUNDS, PROCESS FOR THEIR PRODUCTION AND THEIR USE

This application is a Continuation of application Ser. No. 07/818,474, filed on, Jan. 6, 1992, now abandoned, which is a Continuation of Ser. No. 07/446,113, filed on Dec. 5, 1989, now abandoned.

The present invention relates to N-substituted acylamino acid compounds or their salts useful in the pharmaceutical field. More particularly, the present invention relates to N-substituted acylamino acid compounds or their salts which have renin inhibiting activities and which are thus expected to be useful as hypotensive drugs.

A renin-angiotensin system is one of hypertensive systems in the living body, and it is an important system for regulating the blood pressure-body fluid electrolyte. Renin is secreted from renal juxtaglomerular cells and enters into the whole body circulation system via the renal vein. In the blood, there exists angiotensinogen which is a glycoprotein produced in the liver. Renin reacts on angiotensinogen to form angiotensin I. Most of angiotensin I will be converted to angiotensin II by angiotensin I-converting enzyme which is present in the pulmonary vascular endothelial cells in one cycle of pulmonary circulation. Angiotensin II thus formed directly induces contraction of smooth muscles of peripheral blood vessels and thus shows a strong hypertensive activity. It further acts on the adrenal cortex to induce secretion of aldosterone, which in turn acts on the renal to facilitate reabsorption of sodium, whereby the effective circulatory blood flow increases, the cardiac output increases and the peripheral vascular resistance increases so that the blood pressure increases.

It is known that hypertension will be brought about if this renin-angiotensin system was enhanced abnormally. Typical examples are renal vascular hypertension and malignant hypertension. Further, as a rare case, hypertension caused by a renin producing tumor is known.

For the treatment of the hypertension due to the enhancement of the renin-angiotensin system, inhibitors against the angiotensin I-converting enzyme have been studied, developed and subjected to clinical tests. However, such inhibitors are suspected to have side effects, since the substrate specificity of the angiotensin I-converting enzyme is broad to some extent and there exist some enzymes similar to the angiotensin I-converting enzyme in the living body. On the other hand, it is known that renin has a strict substrate specificity. Accordingly, an inhibitor against renin has a strong specificity and can be a superior hypotensive drug. For this reason, the research on renin inhibitors has been very active, and a number of renin inhibitors have been proposed.

However, most of these inhibitors are polypeptides, which are hardly absorbable by oral administration and which are susceptible to decomposition by a protease in vivo. Besides, they have high lipophilicity and are likely to be readily excreted to bile, whereby the retention of the hypotensive effects can not be expected.

On the other hand, Japanese Unexamined Patent Publication No. 275258/1986 discloses dipeptides represented by the formula:

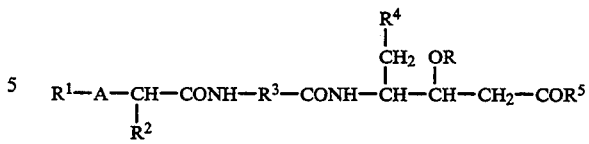

wherein each of $R^1$ and $R^2$ which may be the same or different is a $—B—R^6$ group wherein B is a single bond or a straight chain or branched chain lower alkylene group which may have a double bond in the chain, and $R^6$ is an aryl group or a heteroaryl group, a $C_{1-10}$ alkyl group or a $—E—R^7$ group wherein E is a lower alkylene group which may be interrupted by one oxygen atom, and $R^7$ is a lower alkoxy group, an aryloxy group, an arylthio group, an aralkyloxy group or a nitrogen-containing heterocyclyl group; $R^3$ is an ethylene, trimethylene or tetramethylene group which may be substituted by a lower alkyl, phenyl or hydroxyl group, a

group wherein $R^8$ is a nitrogen-containing heterocyclyl-substituted lower alkyl group, a $C_{5-18}$ alkyl group, a $C_{2-5}$ alkenyl or $C_{2-5}$ alkynyl group which may be substituted by halogen, or a

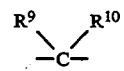

wherein each of $R^9$ and $R^{10}$ which may be the same or different is a lower alkyl group, or $R^9$ and $R^{10}$ form together with the adjacent carbon atom a $C_{3-8}$ cycloalkyl group; $R^4$ is an isopropyl group, a $C_{3-8}$ cycloalkyl group or a phenyl group; $R^5$ is a hydroxyl group, a $C_{1-10}$ alkoxy group, an aryloxy group, an amino group, a mono-or di-($C_{1-10}$ alkyl) amino group (wherein the alkyl group may have one or two substituents which may be the same or different and which are selected from the group consisting of a hydroxyl group, a lower alkoxy group, a halogen atom, an unsubstituted or substituted phenyl group, a pyridyl group, a $C_{3-8}$ cycloalkyl group, a di(lower alkyl)amino group, a di(hydroxy lower alkyl)amino group or a nitrogen-containing heterocyclyl group), a mono or di($C_{3-4}$ alkenyl)amino group, a $C_{3-8}$ cycloalkylamino group, an arylamino group, a nitro-containing heterocyclylamino group wherein the amino and heterocyclyl are linked by N—C, a nitrogen-containing heterocyclyl group wherein the heterocyclyl group is linked to a carbonyl group by a nitrogen atom contained in the group, or a $—NHR^{11}$ group wherein $R^{11}$ is an amino group, a $C_{1-10}$ aliphatic acylamino group which may be substituted by a halogen atom, a lower alkoxy group, an aryloxy group, an arylacyl group, an aryl group or a $C_{3-8}$ cycloalkyl group, an arylacylamino group, a cinnamoylamino group, a heteroarylacylamino group, a lower alkylamino group which may be substituted by a hydroxyl group, a lower alkoxy group, a $C_{1-5}$ aliphatic acyloxy group, an arylacyloxy group or an aryl group, an arylamino group or a nitrogen-containing heterocyclyl group wherein the heterocyclyl group is linked to —NH— by a nitrogen atom; R is a hydrogen atom, a $C_{1-6}$ aliphatic acyl group or an arylacyl group; and A is a single bond, an oxygen atom or sulfur atom. Further, Japanese Unexamined Patent Publication No. 120370/1987 discloses dipeptide derivatives represented by the formula:

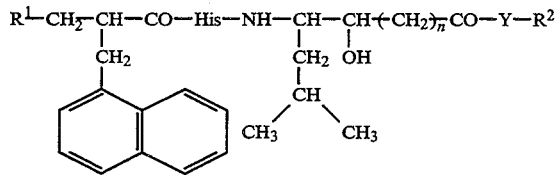

wherein $R^1$ is a carbamoyl group or a lower alkoxycarbonyl group, His is a L-histidine group, n is 0 or 1, Y is —O— or —NH—; and $R^2$ is a $C_{1-7}$ straight chain or branched alkyl group.

The compounds disclosed in the above publications have relatively short peptide chains and are therefore expected to have improved absorbability by oral administration. However, because of the short peptide chains, their renin-inhibiting activities are poor.

To reduce the molecular size is the most effective means to improve the absorbability by oral administration, to be stable against a protease in vivo and to avoid the rapid excretion to bile. However, such a means is likely to lead to a substantial decrease of the renin-inhibiting activities as shown by the above publications.

As a result of years of extensive researches on the peptide derivatives and on the renin-inhibitors, the present inventors have found that the following N-substituted acylamino acid compounds (I) having a novel structure exhibit strong renin-inhibiting activities in spite of their short peptide-chains, and yet they have excellent absorbability by oral administration. The present, invention is based on this discovery.

The present invention provides an N-substituted acylamino acid compound of the formula:

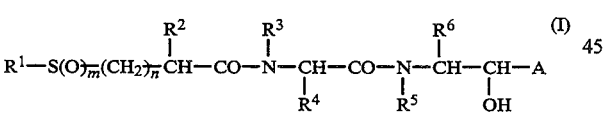

wherein $R^1$ is $C_{1-6}$ alkyl substituted by 1 to 3 substituents selected from the group consisting of $C_{1-5}$ alkanoyloxy and $C_{2-5}$ alkoxycarbonyloxy (wherein said alkyl may further be substituted by 1 to 3 substituents selected from the group consisting of hydroxyl and $C_{1-3}$ alkoxy, =N—$OY^1$ (wherein $Y^1$ is hydrogen, $C_{1-4}$ alkyl which may be substituted by carboxyl, or $C_{1-4}$ alkyl substituted by $C_{2-5}$ alkoxycarbonyl),

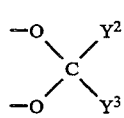

(wherein each of $Y^2$ and $Y^3$ which may be the same or different is hydrogen, $C_{1-4}$ alkyl or phenyl, or $Y^2$ and $Y^3$ together with the adjacent carbon atom form cyclohexylidene or oxo) or

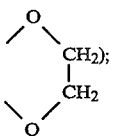

$C_{3-7}$ cycloalkyl substituted by 1 to 3 substituents selected from the group consisting of $C_{1-5}$ alkanoyloxy and $C_{2-5}$ alkoxycarbonyloxy (wherein said cycloalkyl may further be substituted by 1 to 3 substituents selected from the group consisting of hydroxyl and $C_{1-3}$ alkoxy, =N—$OY^1$ (wherein $Y^1$ is as defined above),

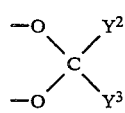

(wherein $Y^2$ and $Y^3$ are as defined above) or

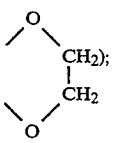

$C_{4-10}$ cycloalkylalkyl substituted by 1 to 3 substituents selected from the group consisting of $C_{1-5}$ alkanoyloxy and $C_{2-5}$ alkoxycarbonyloxy (wherein said cycloalkylalkyl may further be substituted by 1 to 3 substituents selected from the group consisting of hydroxyl and $C_{1-3}$ alkoxy, =N—$OY^1$ (wherein $Y^1$ is as defined above),

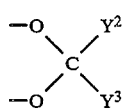

(wherein $Y^2$ and $Y^3$ are as defined above) or

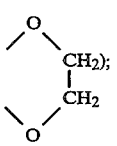

$C_{6-10}$ aryl substituted by 1 to 3 substituents selected from the group consisting of $C_{1-5}$ alkanoyloxy and $C_{2-5}$ alkoxycarbonyloxy (wherein said aryl may further be substituted by 1 to 3 substituents selected from the group consisting of $C_{1-3}$ alkyl which may be substituted by 1 or 2 substituents selected from the group consisting of $C_{1-5}$ alkanoyloxy and $C_{2-5}$ alkoxycarbonyloxy, hydroxyl and $C_{1-3}$ alkoxy,

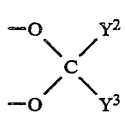

(wherein $Y^2$ and $Y^3$ are as defined above) or

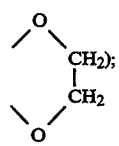

C$_{7-15}$ aralkyl substituted by 1 to 3 substituents selected from the group consisting of C$_{1-5}$ alkanoyloxy and C$_{2-5}$ alkoxycarbonyloxy (wherein said aralkyl may further be substituted by 1 to 3 substituents selected from the group consisting of C$_{1-3}$ alkyl which may be substituted by 1 or 2 substituents selected from the group consisting of C$_{1-5}$ alkanoyloxy and C$_{2-5}$ alkoxycarbonyloxy, hydroxyl and C$_{1-3}$ alkoxy, =N—OY$^1$ (wherein Y$^1$ is as defined above), provided that =N—OY$^1$ is substituted only on a carbon atom of the alkylene of said aralkyl,

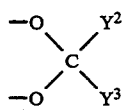

(wherein Y$^2$ and Y$^3$ are as defined above) or

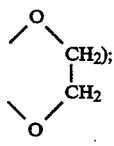

heterocyclic substituted by 1 to 6 substituents selected from the group consisting of C$_{1-5}$ alkanoyloxy and C$_{2-5}$ alkoxycarbonyloxy (wherein said heterocyclic is monocyclic or bicyclic containing 1 to 4 hereto-atoms selected from the group consisting of nitrogen, and oxygen, and said heterocyclic may further be substituted by spirohexyl, oxo, phenyl or 1 to 3 substituents selected from the group consisting alkyl which may be substituted by 1 or 2 substituents selected from the group consisting of C$_{1-5}$ alkanoyloxy and C$_{2-5}$ alkoxycarbonyloxy, hydroxyl and C$_{1-5}$ alkoxy); hetrocycle C$_{1-6}$ alkyl substituted by 1 to 6 substituents selected from the group consisting of C$_{1-5}$ alkanoyloxy and C$_{2-5}$ alkoxycarbonyloxy (wherein said heterocyclic is monocyclic or bicyclic containing 1 to 4 hereto-atoms selected from the group consisting of nitrogen, sulfur and oxygen, and said heterocycle C$_{1-6}$ alkyl may further be substituted by spirohexyl, oxo, phenyl or 1 to 3 substituents selected from the group consisting of C$_{1-3}$ alkyl which may be substituted by 1 to 2 substituents selected from the group consisting of C$_{1-5}$ alkanoyloxy and C$_{2-5}$ alkoxycarbonyloxy, hydroxyl and C$_{1-3}$ each of R$^2$, R$^4$ and R$^6$ which may be the same or different is hydrogen, unsubstituted or substituted C$_{1-6}$ unsubstituted or substituted C$_{3-7}$ cycloalkyl, unsubstituted or substituted C$_{4-10}$ cycloalkylalkyl, unsubstituted or substituted C$_{6-10}$ aryl, unsubstituted or substituted C$_{7-15}$ aralkyl or unsubstituted or substituted monocyclic or bicyclic heterocyclic containing 1 to 4 hetero-atoms selected from the group consisting of nitrogen, sulfur and oxygen; each of R$^3$ and R$^5$ which may be the same or different is hydrogen or C$_{1-6}$ alkyl; A is —CH(OH)—(CH$_2$)$_q$—R$^7$ (wherein R$^7$ is hydrogen, unsubstituted or substituted C$_{1-6}$ alkyl, unsubstituted or substituted C$_{3-7}$ cycloalkyl, unsubstituted or substituted C$_{4-10}$ cycloalkylalkyl, unsubstituted or substituted C$_{6-10}$ aryl, unsubstituted or substituted C$_{7-15}$ aralkyl, unsubstituted or substituted monocyclic or-bicyclic heterocyclic containing 1 to 4 hetero-atoms selected from the group consisting of nitrogen, sulfur and oxygen or —E—R$^{10}$ (wherein E is —S(O)$_i$— (wherein i is 0, 1 or 2), oxygen or —NR$^{11}$— (wherein R$^{11}$ is hydrogen, unsubstituted or substituted C$_{1-6}$ alkyl, unsubstituted or substituted C$_{3-7}$ cycloalkyl, unsubstituted or substituted C$_{4-10}$ cycloalkylalkyl, unsubstituted or substituted C$_{6-10}$ aryl or unsubstituted or substituted C$_{7-15}$ aralkyl), and R$^{10}$ is hydrogen, unsubstituted or substituted C$_{1-6}$ alkyl, unsubstituted or substituted C$_{3-7}$ cycloalkyl, unsubstituted or substituted C$_{4-10}$ cycloalkylalkyl, unsubstituted or substituted C$_{6-10}$ aryl, unsubstituted or substituted C$_{7-15}$ aralkyl or unsubstituted or substituted monocyclic or bicyclic heterocyclic containing 1 to 4 hetero-atoms selected from the group consisting of nitrogen, sulfur and oxygen, provided that when R$^{10}$ is hydrogen, i is 0) and q is an integer of 0 to 5) or —CH$_2$—CHR$^8$—CO—R$^9$ wherein R$^8$ is hydrogen, unsubstituted or substituted C$_{1-6}$ alkyl, unsubstituted or substituted C$_{3-7}$ cycloalkyl, unsubstituted or substituted C$_{4-10}$ cycloalkylalkyl, unsubstituted or substituted C$_{6-10}$ aryl, unsubstituted or substituted C$_{7-15}$ aralkyl or unsubstituted or substituted monocyclic or bicyclic heterocyclic containing 1 to 4 hetero-atoms selected from the group consisting of nitrogen, sulfur and oxygen, and R$^9$ is hydroxyl, —OX (wherein X is unsubstituted or substituted C$_{1-6}$ alkyl, unsubstituted or substituted C$_{6-10}$ aryl, unsubstituted or substituted C$_{7-15}$ aralkyl, C$_{3-9}$ alkoxycarbonyloxyalkyl or phthalidyl) or —N(Y$^4$)(Y$^5$) wherein each of Y$^4$ and Y$^5$ which may be the same or different is hydrogen, unsubstituted or substituted C$_{1-6}$ alkyl, unsubstituted or substituted C$_{6-10}$ aryl, unsubstituted or substituted C$_{7-15}$ aralkyl or unsubstituted or substituted C$_{3-7}$ cycloalkyl, or Y$^4$ and Y$^5$ together with the adjacent nitrogen atom form 5- or 6-membered heterocyclic which may further contain other hetero-atoms selected from the group consisting of nitrogen, oxygen or sulfur)); m is 0, 1 or 2; and n is an integer of from 1 to 5; or a salt thereof.

Further, the present invention provides a process for producing an N-substituted acylamino acid compound of the formula I or its salt.

The present invention also provides a hypotensive drug comprising an effective amount of an N-substituted acylamino acid compound of the formula I or its pharmaceutically acceptable salt, and a pharmaceutically acceptable carrier.

Furthermore, the present invention provides an intermediate compound useful for the production of the compound of the present invention, which has the formula:

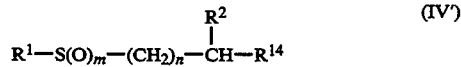

wherein R$^1$ is C$_{1-6}$ alkyl substituted by 1 to 3 substituents selected from the group consisting of C$_{1-5}$ alkanoyloxy and C$_{2-5}$ alkoxycarbonyloxy (wherein said alkyl may further be substituted by 1 to 3 substituents selected from the group consisting of hydroxyl and C$_{1-3}$ alkoxy, =N—OY$^1$ (wherein Y$^1$ is as defined above),

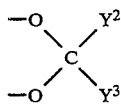

(wherein $Y^2$ and $Y^3$ are as defined above) or

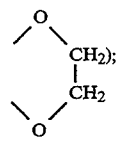

$C_{3-7}$ cycloalkyl substituted by 1 to 3 substituents selected from the group consisting of $C_{1-5}$ alkanoyloxy and $C_{2-5}$ alkoxycarbonyloxy (wherein said cycloalkyl may further be substituted by 1 to 3 substituents selected from the group consisting of hydroxyl and $C_{1-3}$ alkoxy, $=N-OY^1$ (wherein $Y^1$ is as defined above),

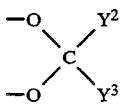

(wherein $Y^2$ and $Y^3$ are as defined above) or

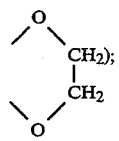

$C_{4-10}$ cycloalkylalkyl substituted by 1 to 3 substituents selected from the group consisting of $C_{1-5}$ alkanoyloxy and $C_{2-5}$ alkoxycarbonyloxy (wherein said cycloalkylalkyl may further be substituted by 1 to 3 substituents selected from the group consisting of hydroxyl and $C_{1-3}$ alkoxy, $=N-OY^1$ (wherein $Y^1$ is as defined above),

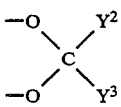

(wherein $Y^2$ and $Y^3$ are as defined above) or

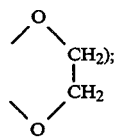

$C_{6-10}$ aryl substituted by 1 to 3 substituents selected from the group consisting of $C_{1-5}$ alkanoyloxy and $C_{2-5}$ alkoxycarbonyloxy (wherein said aryl may further be substituted by 1 to 3 substituents selected from the group consisting of $C_{1-3}$ alkyl which may be substituted by 1 or 2 substituents selected from the group consisting of $C_{1-5}$ alkanoyloxy and $C_{2-5}$ alkoxycarbonyloxy, hydroxyl and $C_{1-3}$ alkoxy,

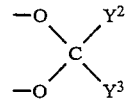

(wherein $Y^2$ and $Y^3$ are as defined above) or

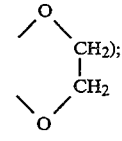

$C_{7-15}$ aralkyl substituted by 1 to 3 substituents selected from the group consisting of $C_{1-5}$ alkanoyloxy and $C_{2-5}$ alkoxycarbonyloxy (wherein said aralkyl may further be substituted by 1 to 3 substituents selected from the group consisting of $C_{1-3}$ alkyl which may be substituted by 1 or 2 substituents selected from the group consisting of $C_{1-5}$ alkanoyloxy and $C_{2-5}$ alkoxycarbonyloxy, hydroxyl and $C_{1-3}$ alkoxy, $=N-OY^1$ (wherein $Y^1$ is as defined above), provided that $=N-OY^1$ is substituted only on a carbon atom of the alkylene of said aralkyl,

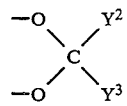

(wherein $Y^2$ and $Y^3$ are as defined above) or

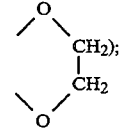

heterocyclic substituted by 1 to 6 substituents selected from the group consisting of $C_{1-5}$ alkanoyloxy and $C_{2-5}$ alkoxycarbonyloxy (wherein said heterocyclic is monocyclic or bicyclic containing 1 to 4 hetero-atoms selected from the group consisting of nitrogen, sulfur and oxygen, and said heterocyclic may further be substituted by spirohexyl, oxo, phenyl or 1 to 3 substituents selected from the group consisting of $C_{1-3}$ alkyl which may be substituted by 1 or 2 substituents selected from the group consisting of $C_{1-5}$ alkanoyloxy and $C_{2-5}$ alkoxycarbonyloxy, hydroxyl and $C_{1-3}$ alkoxy); or heterocycle $C_{1-6}$ alkyl substituted by 1 to 6 substituents selected from the group consisting of $C_{1-5}$ alkanoyloxy and $C_{2-5}$ alkoxycarbonyloxy (said heterocyclic is monocyclic or bicyclic containing 1 to 4 hetero-atoms selected from the group consisting of nitrogen, sulfur and oxygen, and said heterocycle $C_{1-6}$ alkyl may further be substituted by spirohexyl, oxo, phenyl or 1 to 3 substituents selected from the group consisting of $C_{1-3}$ alkyl which may be substituted by 1 or 2 substituents selected from the group consisting of $C_{1-5}$ alkanoyloxy and $C_{2-5}$ alkoxycarbonyloxy, hydroxyl and $C_{1-3}$ alkoxy); $R^2$ is hydrogen, unsubstituted or substituted $C_{1-6}$ alkyl, unsubstituted or substituted $C_{3-7}$ cycloalkyl, unsubstituted or substituted $C_{4-10}$ cycloalkylalkyl, unsubstituted or substituted $C_{6-10}$ aryl, unsubstituted or substituted $C_{7-15}$ aralkyl or unsubstituted or substituted monocyclic or bicyclic heterocyclic containing 1 to 4 hetero-atoms selected from the group consisting of nitrogen, sulfur and oxygen; $R^{14}$ is carboxyl, a reactive derivative of carboxyl or protected carboxyl; m is 0, 1 or 2; and n is an integer of from 1 to 5.

In the accompanying drawing, FIG. 1 is a graph showing the hypotensive activities of a compound of the present invention in monkeys, as measured in Test Example 2 given hereinafter.

Now, the definitions of various terms of referred to in this specification and some specific examples falling within such terms will be given.

The $C_{1-6}$ alkyl substituted by 1 to 3 substituents selected from the group consisting of $C_{1-5}$ alkanoyloxy and $C_{2-5}$ alkoxycarbonyloxy (wherein said alkyl may further be substituted by 1 to 3 substituents selected from the group consisting of hydroxyl and $C_{1-3}$ alkoxy, =N—$OY^1$ (wherein $Y^1$ is as defined above),

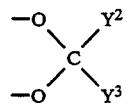

(wherein $Y^2$ and $Y^3$ are as defined above),

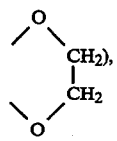

includes $C_{1-6}$alkyl such as methyl, ethyl, propyl, isopropyl, butyl, isobutyl, sec-butyl, tert-butyl, pentyl, isopentyl, hexyl or isohexyl, which is substituted by 1 to 3 substituents selected from the group consisting of $C_{1-5}$ alkanoyloxy such as formyloxy, acetoxy, propionyloxy, butyryloxy, isobutyryloxy, valeryloxy, 2-methylbutyryloxy, isovaleryloxy or pivaloyloxy, and $C_{2-5}$ alkoxycarbonyloxy such as methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy or tert-butoxycarbonyloxy, or, as the case requires may further be substituted by 1 to 3 substituents selected from the group consisting of hydroxyl, and $C_{1-3}$ alkoxy such as methoxy, ethoxy, propoxy or isopropoxy, =N—$OY^1$ (wherein $Y^1$ is as defined above) such as hydroxyimino, methoxyimino, ethoxyimino, propoxyimino, isopropoxyimino, butoxyimino, isobutoxyimino, sec-butoxyimino, tert-butoxyimino, carboxymethoxyimino, 1-carboxyethoxyimino, 2-carboxyethoxyimino, 3-carboxypropoxyimino, 1-carboxy-1-methylethoxyimino, methoxycarbonylmethoxyimino, ethoxycarbonylmethoxyimino, propoxycarbonylmethoxyimino, isopropoxycarbonylmethoxyimino, butoxycarbonylmethoxyimino, isobutoxycarbonylmethoxyimino, tert-butoxycarbonylmethoxyimino, 1-methoxycarbonylethoxyimino, 1-tert-butoxycarbonylethoxyimino, 1-methoxycarbonyl-1-methylethoxyimino, 1-sec-butoxycarbonyl-1-methylethoxyimino or 1-tert-butoxycarbonyl-1-methylethoxyimino,

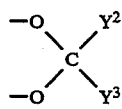

(wherein $Y^2$ and $Y^3$ are as defined above) such as

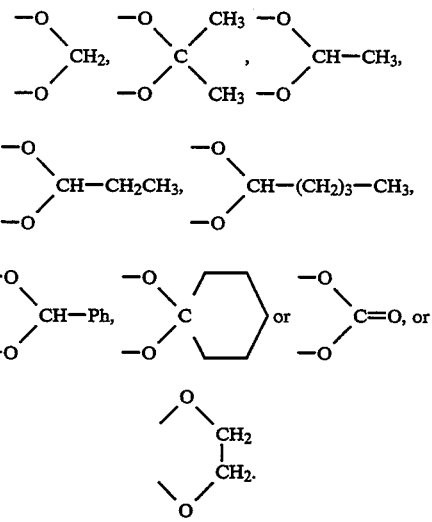

The $C_{1-3}$ alkyl substituted by 1 or 2 substituents selected from the group consisting of $C_{1-5}$ alkanoyloxy and $C_{2-5}$ alkoxycarbonyloxy, includes, for example, methyl, ethyl, propyl and isopropyl substituted by 1 to 3 substituents selected from the group consisting of $C_{1-5}$ alkanoyloxy such as formyloxy, acetoxy, propionyloxy, butyryloxy, isobutyryloxy, valeryloxy, 2-methylbutyryloxy, isovaleryloxy or pivaloyloxy, and $C_{2-5}$ alkyloxycarbonyloxy such as methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy or tert-butoxycarbonyloxy.

The $C_{3-7}$ cycloalkyl substituted by 1 to 3 substituents selected from the group consisting of $C_{1-5}$ alkanoyloxy and $C_{2-5}$ alkoxycarbonyloxy (wherein said cycloalkyl may further be substituted by 1 to 3 substituents selected from the group consisting of hydroxyl and $C_{1-3}$ alkoxy, =N—$OY^1$ (wherein $Y^1$ is as defined above),

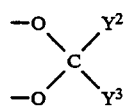

(wherein $Y^2$ and $Y^3$ are as defined above) or

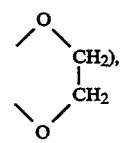

includes $C_{3-7}$ cycloalkyl such as cyclopropyl, cyclobutyl, cyclopentyl, cyclohexyl or cycloheptyl, which is substituted by 1 to 3 substituents selected from the group consisting of $C_{1-5}$ alkanoyloxy such as formyloxy, acetoxy, propionyloxy, butyryloxy, isobutyryloxy, valeryloxy, 2-methylbutyryloxy, isovaleryloxy or pivaloyloxy, and $C_{2-5}$ alkoxycarbonyloxy such as methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy or tert-butoxycarbonyloxy, or as the case requires, may further be substituted by 1 to 3 substituents selected from the group consisting of hydroxy and C$_{1-3}$ alkoxy such as methoxy, ethoxy, propoxy or isopropoxy, =N—OY$^1$ (wherein Y$^1$ is as defined above) such as hydroxyimino, methoxyimino, ethoxyimino, propoxyimino, isopropoxyimino, butoxyimino, isobutoxyimino, sec-butoxyimino, tert-butoxyimino, carboxymethoxyimino, 1-carboxyethoxyimino, 2-carboxyethoxyimino, 3-carboxypropoxyimino, 1-carboxy-1-methylethoxyimino, methoxycarbonylmethoxyimino, ethoxycarbonylmethoxyimino,-propoxycarbonylmethoxyimino, isopropoxycarbonylmethoxyimino, butoxycarbonylmethoxyimino, isobutoxycarbonylmethoxyimino, tert-butoxycarbonylmethoxyimino, 1-methoxycarbonylethoxyimino, 1-tert-butoxycarbonylethoxyimino, 1-methoxycarbonyl-1-methylethoxyimino, 1-sec-butoxycarbonyl-1-methylethoxyimino or 1-tert-butoxycarbonyl-1-methylethoxyimino,

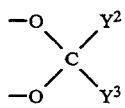

(wherein Y$^2$ and Y$^3$ are as defined above) such as

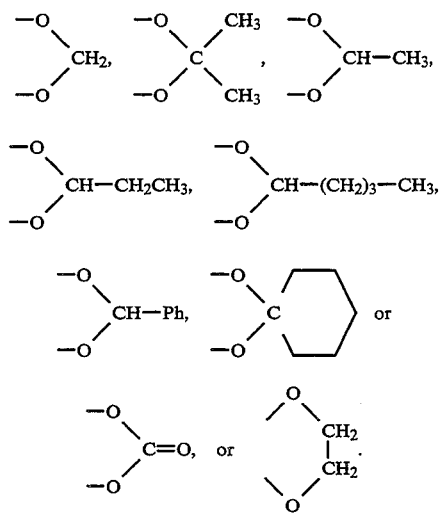

The C$_{4-10}$ cycloalkylalkyl substituted by 1 to 3 substituents selected from the group consisting of C$_{1-5}$ alkanoyloxy and C$_{2-5}$ alkoxycarbonyloxy (wherein said cycloalkylalkyl may further be substituted by 1 to 3 substituents selected from the group consisting of hydroxyl and C$_{1-3}$ alkoxy, =N—OY$^1$ (wherein Y$^1$ is as defined above

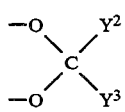

(wherein Y$^2$ and Y$^3$ are as defined above ) or

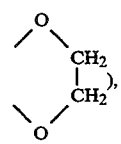

includes C$_{4-10}$ cycloalkylalkyl such as cyclopropylmethyl, cyclobutylmethyl, cyclopentylmethyl, cyclohexylmethyl, cycloheptylmethyl, 1-cyclopropylethyl, 1-cyclobutylethyl, 1-cyclopentylethyl, 1-cyclohexylethyl, 1-cycloheptylethyl, 2-cyclopropylethyl, 2-cyclobutylethyl, 2-cyclopentylethyl, 2-cyclohexylethyl, 2-cycloheptylethyl, 1-cyclopropylpropyl, 1-cyclobutylpropyl, 1-cyclopentylpropyl, 1-cyclohexylpropyl, 1-cycloheptylpropyl, 2-cyclopropylpropyl, 2-cyclobutylpropyl, 2-cyclopentylpropyl, 2-cyclohexylpropyl, 2-cycloheptylpropyl, 3-cyclopropylpropyl, 3-cyclobutylpropyl, 3-cyclopentylpropyl, 3-cyclohexylpropyl, 3-cycloheptylpropyl, 1-methyl-1-cyclopropylethyl, 1-methyl-1-cyclobutylethyl, 1-methyl-1-cyclopentylethyl, 1-methyl-1cyclohexylethyl, 1-methyl-1-cyclopropylethyl, 1-methyl-2-cycloheptylethyl, 1-methyl-2-cyclopentylethyl, 1-methyl-2-cyclobutylethyl, or 1-methyl-2-cycloheptylethyl, which is substituted by 1 to 3 is substituents selected from the group consisting of C$_{1-5}$ alkanoyloxy such as formyloxy, acetoxy, propionyloxy, butyryloxy, isobutyryloxy, valeryloxy, 2-methylbutyryloxy, isovaleryloxy or pivaloyloxy, and C$_{2-5}$ alkyloxycarbonyloxy such as methoxycarbonyloxy, ethoxycarbonyloxy, isopropoxycarbonyloxy, isopropoxycarbonyloxy, butoxycarbonyloxy, isobutoxycarbonyloxy, sec-butoxycarbonyloxy or tert-butoxycarbonyloxy, or, as the case requires, may further be substituted by 1 to 3 substituents selected from the group consisting of hydroxyl and C$_{1-3}$ alkoxy such as methoxy, ethoxy, propoxy or isopropoxy, =N—OY$^1$ (wherein Y$^1$ is as defined above) such as hydroxyimino, methoxyimino, ethoxyimino, propoxyimino, isopropoxyimino, butoxyimino, isobutoxyimino, sec-butoxyimino, tert-butoxyimino, carboxymethoxyimino, 1-carboxyethoxyimino, 2-carboxyethoxyimino, 3-carboxypropoxyimino, 1-carboxy-1-methylethoxyimino, methoxycarbonylmethoxyimino, ethoxycarbonylmethoxyimino, propoxycarbonylmethoxyimino, isopropoxycarbonylmethoxyimino, butoxycarbonylmethoxyimino, isobutoxycarbonylmethoxyimino, tert-butoxycarbonylmethoxyimino, 1-methoxycarbonylethoxyimino, 1-tert-butoxycarbonylethoxyimino, 1-methoxycarbonyl-1-methylethoxyimino, 1-sec-butoxycarbonyl-1-methylethoxyimino or 1-tert-butoxycarbonyl-1-methylethoxyimino,

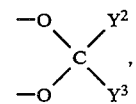

(wherein Y$^2$ and Y$^3$ are as defined above) such as

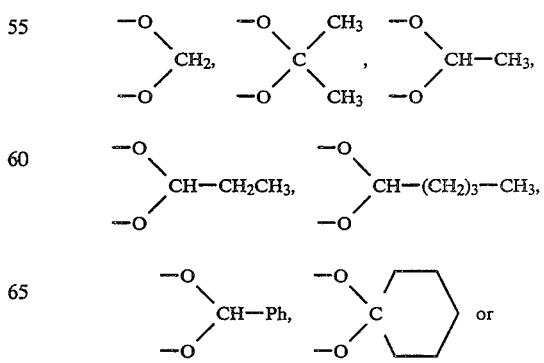

-continued

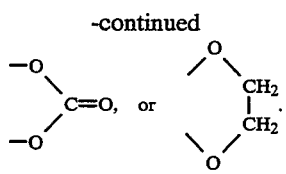

The C$_{6-10}$ aryl substituted by 1 to 3 substituents selected from the group consisting of C$_{1-5}$ alkanoyloxy and C$_{2-5}$ alkoxycarbonyloxy (wherein said aryl may further be substituted by 1 to 3 substituents selected from the group consisting of C$_{1-3}$ alkyl which may be substituted by 1 or 2 substituents selected from the group consisting of C$_{1-5}$ alkanoyloxy and C$_{2-5}$ alkoxycarbonyloxy, hydroxyl and C$_{1-3}$ alkoxy,

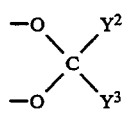

(wherein Y$^2$ and Y$^3$ are as defined above) or

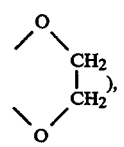

includes C$_{6-10}$ aryl such as phenyl, 1-naphthyl or 2-naphthyl, which is substituted by 1 to 3 substituents selected from the group consisting of C$_{1-5}$ alkanoyloxy such as formyloxy, acetoxy, propionyloxy, butyryloxy, isobutyryloxy, valeryloxy, 2-methylbutyryloxy, isovaleryloxy or pivaloyloxy, and C$_{2-5}$ alkoxycarbonyloxy such as methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy or tert-butoxycarbonyloxy, or, as the case requires, may further be substituted by 1 to 3 substituents selected from the group consisting of C$_{1-3}$ alkyl such as methyl, ethyl, propyl or isopropyl which may be substituted by 1 or 2 substituents selected from the group consisting of said alkanoyloxy and said alkyloxycarbonyloxy, hydroxyl and C$_{1-3}$ alkoxy such as methoxy, ethoxy, propoxy or isopropoxy,

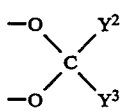

(wherein Y$^2$ and Y$^3$ are as defined, above) such as

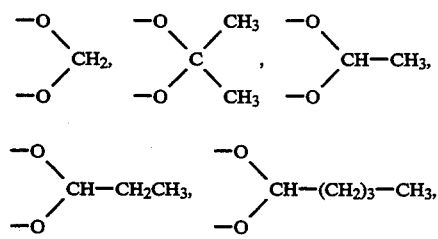

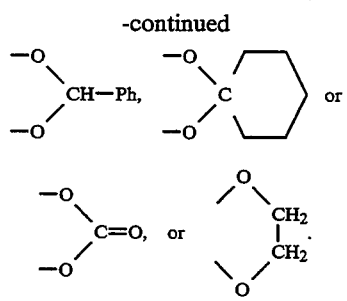

The C$_{7-15}$ aralkyl substituted by 1 to 3 substituents selected from the group consisting of C$_{1-5}$ alkanoyloxy and C$_{2-5}$ alkoxycarbonyloxy (wherein said aralkyl may further be substituted by 1 to 3 substituents selected from the group consisting of C$_{1-3}$ alkyl which may be substituted by 1 or 2 substituents selected from the group consisting of C$_{1-5}$ alkanoyloxy and C$_{2-5}$ alkoxycarbonyloxy, hydroxyl and C$_{1-3}$ alkoxy, =N—OY$^1$ (wherein Y$^1$ is as defined above), provided that =N—OY$^1$ is substituted only on a carbon atom of the alkylene of said aralkyl,

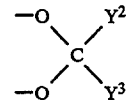

(wherein Y$^2$ and Y$^3$ are as defined above) or

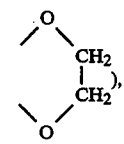

includes C$_{7-15}$ aralkyl such as benzyl, phenethyl, 1-phenylethyl, 3-phenylpropyl, 2-phenylpropyl, 1-phenylpropyl, 1-naphthylmethyl, 2-naphthylmethyl, 1-(1-naphthyl)ethyl, 1-(2-naphthyl)ethyl, 2-(2-naphthyl)ethyl, 2-(1-naphthyl)ethyl, 1-(1-naphthyl)propyl, 1-(2-naphthyl)propyl, 2-(1-naphthyl)propyl, 2-(2-naphthyl)propyl, 3-(1-naphthyl)propyl, 3-(2-naphthyl)propyl, 1-(1-naphthyl)-1-methylethyl, 1-(2-naphthyl)-2-methylethyl, 1-phenyl-1-methylethyl, 1-methyl-2-phenylethyl, 1-methyl-2-(1-naphthyl)ethyl or 1-methyl-2-(2-naphthyl)ethyl, which is substituted by 1 to 3 substituents selected from the group consisting of C$_{1-5}$ alkanoyloxy such as formyloxy, acetoxy, propionyloxy, butyryloxy, isobutyryloxy, valeryloxy, 2-methylbutyryloxy, isovaleryloxy or pivaloyloxy, and C$_{2-5}$ alkoxycarbonyloxy such as methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy or tert-butoxycarbonyloxy, or, as the case requires may further be substituted by 1 to 3 substituents selected from the group consisting of C$_{1-3}$ alkyl such as methyl, ethyl, propyl or isopropyl which may be substituted by 1 or 2 substituents selected from the group consisting of said C$_{1-5}$ alkanoyloxy, and said C$_{2-5}$ alkoxycarbonyloxy, hydroxyl and C$_{1-3}$ alkoxy such as methoxy, ethoxy, propoxy or isopropoxy, =N—OY$^1$ (Y$^1$ is as defined above) such as hydroxyimino, methoxyimino, ethoxyimino, propoxyimino, isopropoxyimino, butoxyimino, isobutoxyimino, sec-butoxyimino, tert-butoxyimino, carboxymethoxyimino, 1-carboxyethoxyimino, 2-carboxyethoxyimino, 3-carboxypropoxyimino, 1-carboxy-1-methylethoxyimino, methoxycarbonylmethoxyimino, ethoxycarbonylmethoxyimino, propoxycarbonylmethoxyimino, isopropoxycarbonylmethoxyimino, butoxycarbonylmethoxyimino, isobutoxycarbonylmethoxyimino, tert-butoxycarbonylmethoxyimino, 1-methoxycarbonylethoxyimino, 1-tert-butoxycarbonylethoxyimino, 1-methoxycarbonyl-1-methylethoxyimino, 1-sec-butoxycarbonyl-1-methylethoxyimino or 1-tert-butoxycarbonyl-1-methylethoxyimino,

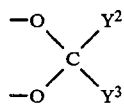

(wherein $Y^2$ and $Y^3$ are as defined above) such as

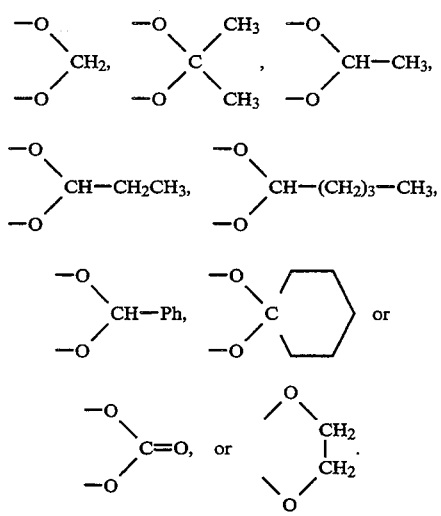

The heterocyclic substituted by 1 to 6 substituents selected from the group consisting of $C_{1-5}$ alkanoyloxy and $C_{2-5}$ alkoxycarbonyloxy (wherein said heterocyclic is monocyclic or bicyclic containing 1 to 4 hetero-atoms selected from the group consisting of nitrogen, sulfur and oxygen, and said heterocyclic may further be substituted by spirohexyl, oxo, phenyl or 1 to 3 substituents selected from the group consisting of $C_{1-3}$ alkyl which may be substituted by 1 or 2 substituents selected from the group consisting of $C_{1-5}$ alkanoyloxy and $C_{2-5}$ alkoxycarbonyloxy, hydroxyl and $C_{1-3}$ alkoxy), includes monocyclic or bicyclic heterocyclic such as pyrolyl, furyl, thienyl, pyridyl, imidazolyl, pyrazolyl, thiazolyl, isothiazolyl, isoxazolyl, oxazolyl, pyrazinyl, pyrimidinyl, pyridazinyl, indolyl, quinolyl, isoquinolyl, phthalazinyl, naphthidinyl, quinoxalinyl, quinazolinyl, 1,4-benzodioxanyl, 1,3-benzodioxanyl, 1,2,3-triazolyl, 1,3,4-triazolyl, 1,3,4-thiadiazolyl, 1,2,3-thiadiazolyl, tetrazolyl, tetrahydropyranyl, tetrahydrofuranyl, 2,4,6-trioxabicyclo[4,3,0]nonane, 2,4,8-trioxabicyclo[4,3,0]nonane, 2,4,7-trioxabicyclo[4,3,0]nonane, 2,4,7-trioxabicyclo[3,3,01]octane, 2,4,6-trioxabicyclo[3,3,01]octane, 2,5,8-trioxabicyclo[4,3,0]nonane, 2,5,7-trioxabicyclo[4,3,0]nonane, 2,5,7-trioxabicyclo[4,4,0]decane, 2,5,8-trioxabicyclo[4,4,0]decane, 2,5,9-trioxabicyclo[4,4,0]decane, tetrahydrothienyl, pyrolidinyl, imidazolidinyl, 2-imidazolinyl, morpholinyl, morpholino, piperazinyl, piperidino, piperazin-N-oxide, piperidinyl, piperidine-N-oxide, thiomorpholino, thiomorpholinyl, morpholine-N-oxide or N-alkylmorpholino such as N-methylmorpholino, N-ethylmorpholino or N-propylmorpholino, which is substituted by 1 to 6 substituents selected from the group consisting of $C_{1-5}$ alkanoyloxy such as formyloxy, acetoxy, propionyloxy, butyryloxy, isobutyryloxy, valeryloxy, 2-methylbutyryloxy, isovaleryloxy or pivaloyloxy, and $C_{2-5}$ alkoxycarbonyloxy such as methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy or tert-butoxycarbonyloxy, or, as the case requires, may further be substituted by spirohexyl, oxo, phenyl or 1 to 3 substituents selected from the group consisting of $C_{1-3}$ alkyl such as methyl, ethyl, propyl or isopropyl which may be substituted by 1 or 2 substituents selected from the group consisting of said alkanoyloxy and said alkoxycarbonyloxy, hydroxyl and $C_{1-3}$ alkoxy such as methoxy, ethoxy, propoxy or isopropoxy.

The heterocycle $C_{1-6}$ alkyl substituted by 1 to 6 substituents selected from the group consisting of $C_{1-5}$ alkanoyloxy and $C_{2-5}$ alkoxycarbonyloxy (wherein said heterocyclic is monocyclic or bicyclic containing 1 to 4 hetero-atoms selected from the group consisting of nitrogen, sulfur and oxygen, and said heterocycle $C_{1-6}$ alkyl may further be substituted by spirohexyl, oxo, phenyl or 1 to 3 substituents selected from the group consisting of $C_{1-3}$ alkyl which may be substituted by 1 to 2 substituents selected from the group consisting of $C_{1-5}$ alkanoyloxy and $C_{2-5}$ alkoxycarbonyloxy, hydroxyl and $C_{1-3}$ alkoxy), includes methyl, ethyl, propyl, isopropyl, butyl, isobutyl, sec-butyl, tert-butyl, pentyl, isopentyl, hexyl or isohexyl substituted by monocyclic or bicyclic heterocyclic, such as pyrolyl, furyl, thienyl, pyridyl, imidazolyl, pyrazolyl, thiazolyl, isothiazolyl, isoxazolyl, oxazolyl, pyrazinyl, pyrimidinyl, pyridazinyl, indolyl, quinolyl, isoquinolyl, phthalazinyl, naphthidinyl, quinoxalinyl, quinazolinyl, 1,4-benzodioxanyl, 1,3-benzodioxanyl, 1,2,3-triazolyl, 1,3,4-triazolyl, 1,3,4-thiadiazolyl, 1,2,3-thiadiazolyl, tetrazolyl, tetrahydropyranyl, tetrahydrofuranyl, 2,4,6-trioxabicyclo[4,3,0]nonane, 2,4,8-trioxabicyclo[4,3,0]nonane, 2,4,7-trioxabicyclo[4,3,0]nonane, 2,4,7-trioxabicyclo[3,3,01]octane, 2,4,6-trioxabicyclo[3,3,01]octane, 2,5,8-trioxabicyclo[4,3,0]nonane, 2,5,7-trioxabicyclo[4,3,0]nonane, 2,5,7-trioxabicyclo[4,4,0]decane, 2,5,8-trioxabicyclo[4,4,0]decane, 2,5,9-trioxabicyclo[4,4,0]decane, tetrahydrothienyl, pyrolidinyl, imidazolidinyl, 2-imidazolinyl, morpholinyl, morpholino, piperazinyl, piperidino, piperazine-N-oxide, piperidinyl, piperidine-N-oxide, thiomorpholino, thiomorpholinyl, morpholine-N-oxide or N-alkylmorpholino such as N-methylmorpholino, N-ethylmorpholino or N-propylmorpholino, which is substituted by 1 to 6 substituents selected from the group consisting of $C_{1-5}$ alkanoyloxy such as formyloxy, acetoxy, propionyloxy, butyryloxy, isobutyryloxy, valeryloxy, 2-methylbutyryloxy, isovaleryloxy or pivaloyloxy and $C_{2-5}$alkoxycarbonyloxy such as methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy or tert-butoxycarbonyloxy, or as the case requires, may further be substituted by spirohexyl, oxo, phenyl or 1 to 3 substituents selected from the group consisting of $C_{1-3}$ alkyl such as methyl, ethyl, propyl or isopropyl which may be substituted by 1 or 2 substituents selected from the group consisting of said alkanoyloxy and said alkoxycarbonyloxy, hydroxyl and $C_{1-3}$ alkoxy such as methoxy, ethoxy, propoxy or isopropoxy.

The unsubstituted or substituted $C_{1-6}$ alkyl includes straight chain or branched chain $C_{1-6}$ alkyl such as methyl, ethyl, propyl, isopropyl, butyl, isobutyl, sec-butyl, tert-butyl, pentyl, neopentyl, isopentyl, hexyl or isohexyl which may be substituted by halogen such as chlorine, fluorine or bromine, hydroxyl, $C_{1-4}$ alkoxy such as methoxy, ethoxy, propoxy, isopropoxy, butoxy, isobutoxy, sec-butoxy or tert-butoxy, $C_{6-10}$ aryloxy such as phenoxy, 1-naphthyloxy or 2-naphthyloxy, $C_{7-15}$ aralkyloxy such as benzyloxy, phenethyloxy, 1-naphthylmethyloxy or 2-naphthylmethyloxy, amino, mono- or di-$C_{1-4}$ alkylamino such as methylamino, ethylamino, propylamino, isopropylamino, butylamino, sec-butylamino, isobutylamino, tert-butylamino, dimethylamino or diethylamino, $C_{6-10}$ arylamino such as phenylamino, 1-naphthylamino or 2-naphthylamino, $C_{7-15}$ aralkylamino such as benzylamino, phenethylamino, 1-naphthylmethylamino or 2-naphthylmethylamino, carboxyl, formyl, $C_{2-6}$ alkoxycarbonyl such as methoxycarbonyl, ethoxycarbonyl, propoxycarbonyl, isopropoxycarbonyl, butoxycarbonyl, sec-butoxycarbonyl, isobutoxycarbonyl or tert-butoxycarbonyl, $C_{7-15}$ aryloxycarbonyl such as phenoxycarbonyl, 1-naphthyloxycarbonyl or 2-naphthyloxycarbonyl, $C_{8-15}$ aralkyloxycarbonyl such as benzyloxycarbonyl, phenethyloxycarbonyl, 1-naphthylmethyloxycarbonyl or 2-naphthylmethyloxycarbonyl, mercapto, $C_{1-4}$ alkylthio such as methylthio, ethylthio, propylthio, isopropylthio, butylthio, sec-butylthio, isobutylthio or tert-butylthio, $C_{6-10}$ arylthio such as phenylthio, 1-naphthylthio or 2-naphthylthio, $C_{7-15}$ aralkylthio such as benzylthio, phenethylthio, 1-naphthylmethylthio or 2-naphthylmethylthio, $C_{1-4}$ alkylsulfinyl such as methylsulfinyl, ethylsulfinyl, propylsulfinyl, isopropylsulfinyl, butylsulfinyl, isobutylsulfinyl or tert-butylsulfinyl, $C_{6-10}$ arylsulfinyl such as phenylsulfinyl, 1-naphthylsulfinyl or 2-naphthylsulfinyl, $C_{7-15}$ aralkylsulfinyl such as benzylsulfinyl, phenethylsulfinyl, 1-naphthylmethylsulfinyl or 2-naphthylmethylsulfinyl, $C_{1-4}$ alkylsulfonyl such as mesyl, ethylsulfonyl, propylsulfonyl, isopropylsulfonyl, butylsulfonyl, isobutylsulfonyl, sec-butylsulfonyl or tert-butylsulfonyl, $C_{6-10}$ arylsulfonyl such as phenylsulfonyl, 1-naphthylsulfonyl or 2-naphthylsulfonyl, $C_{7-15}$ aralkylsulfonyl such as benzylsulfonyl, phenethylsulfonyl, 1-naphthylmethylsulfonyl or 2-naphthylmethylsulfonyl, or heterocyclic such as pyrolyl, furyl, thienyl, pyridyl, imidazolyl, pyrazolyl, thiazolyl, isothiazolyl, isoxazolyl, oxazolyl, pyrazinyl, pyrimidinyl, pyridazinyl, indolyl, quinolyl, isoquinolyl, phthalazinyl, naphthidinyl, quinoxalinyl, quinazolinyl, 1,4-benzodioxanyl, 1,3-benzodioxanyl, 1,2,3-triazolyl, 1,3,4-triazolyl, 1,3,4-thiadiazolyl, 1,2,3-thiadiazolyl, tetrazolyl, tetrahydrofuranyl, tetrahydrothienyl, pyrolidinyl, imidazolidinyl, 2-imidazolinyl, morpholinyl, morpholino, piperazinyl, piperidino, piperidinyl, thiomorpholino, thiomorpholinyl, morpholine-N-oxide or N-alkylmorpholino such as N-methylmorpholino, ethylmorpholino or N-propylmorpholino.

The unsubstituted or substituted $C_{4-10}$ cycloalkylalkyl includes $C_{4-10}$ cycloalkylalkyl such as cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl, cyclohexylpropyl, 3-cyclopentylpropyl, 4-cyclohexylbutyl or 4-cyclopentylbutyl, which may be substituted by $C_{1-4}$ alkyl such as methyl, ethyl, propyl, isopropyl, butyl, isobutyl, sec-butyl or tert-butyl, halogen such as chlorine, fluorine or bromine, hydroxyl, $C_{1-4}$ alkoxy such as methoxy, ethoxy, propoxy, isopropoxy, butoxy, isobutoxy, sec-butoxy or tert-butoxy, $C_{6-10}$ aryloxy such as phenoxy, 1-naphthyloxy or 2-naphthyloxy, $C_{7-15}$ aralkyloxy such as benzyloxy, phenethyloxy, 1-naphthylmethyloxy or 2-naphthylmethyloxy, amino, mono- or di-$C_{1-4}$ alkylamino such as methylamino, ethylamino, propylamino, isopropylamino, butylamino, sec-butylamino, isobutylamino, tert-butylamino, dimethylamino or diethylamino, $C_{6-10}$ arylamino such as phenylamino, 1-naphthylamino or 2-naphthylamino, $C_{7-15}$ aralkylamino such as benzylamino, phenethylamino, 1-naphthylmethylamino or 2-naphthylmethylamino, carboxyl, formyl, $C_{2-6}$ alkoxycarbonyl such as methoxycarbonyl, ethoxycarbonyl, propoxycarbonyl, isopropoxycarbonyl, butoxycarbonyl, sec-butoxycarbonyl, isobutoxycarbonyl or tert-butoxycarbonyl, $C_{7-15}$ aryloxycarbonyl such as phenoxycarbonyl, 1-naphthyloxycarbonyl or 2-naphthyloxycarbonyl, $C_{8-15}$ aralkyloxycarbonyl such as benzyloxycarbonyl, phenethyloxycarbonyl, 1-naphthylmethyloxycarbonyl or 2-naphthylmethyloxycarbonyl, mercapto, $C_{1-4}$ alkylthio such as methylthio, ethylthio, propylthio, isopropylthio, butylthio, sec-butylthio, isobutylthio or tert-butylthio, $C_{6-10}$ arylthio such as phenylthio, 1-naphthylthio or 2 -naphthylthio, $C_{7-15}$ aralkylthio such as benzylthio, phenethylthio, 1-naphthylmethylthio or 2-naphthylmethylthio, $C_{1-4}$ alkylsulfinyl such as methylsulfinyl, ethylsulfinyl, propylsulfinyl, isopropylsulfinyl, butylsulfinyl, isobutylsulfinyl or tert-butylsulfinyl, $C_{6-10}$ arylsulfinyl such as phenylsulfinyl, 1-naphthylsulfinyl or 2-naphthylsulfinyl, $C_{7-15}$ aralkylsulfinyl such as benzylsulfinyl, phenethylsulfinyl, 1-naphthylmethylsulfinyl or 2-naphthylmethylsulfinyl, $C_{1-4}$ alkylsulfonyl such as mesyl, ethylsulfonyl, propylsulfonyl, isopropylsulfonyl, butylsulfonyl, isobutylsulfonyl, sec-butylsulfonyl or tert-butylsulfonyl, $C_{6-10}$ arylsulfonyl such as phenylsulfonyl, 1-naphthylsulfonyl or 2-naphthylsulfonyl, $C_{7-15}$ aralkylsulfonyl such as benzylsulfonyl, phenethylsulfonyl, 1-naphthylmethylsulfonyl or 2-naphthylmethylsulfonyl, or heterocyclic such as pyrolyl, furyl, thienyl, pyridyl, imidazolyl, pyrazolyl, thiazolyl, isothiazolyl, isoxazolyl, oxazolyl, pyrazinyl, pyrimidinyl, pyridazinyl, indolyl, quinolyl, isoquinolyl, phthalazinyl, naphthidinyl, quinoxalinyl, quinazolinyl, 1,4-benzodioxanyl, 1,3-benzodioxanyl, 1,2,3-triazolyl, 1,3,4-triazolyl, 1,3,4-thiadiazolyl, 1,2,3-thiadiazolyl, tetrazolyl, tetrahydrofuranyl, tetrahydrothienyl, pyrolidinyl, imidazolidinyl, 2-imidazolinyl, morpholinyl, morpholino, piperazinyl, piperidino, piperidinyl, thiomorpholino, thiomorpholinyl, morpholine-N-oxide or N-alkylmorpholino such as N-methylmorpholino, N-ethylmorpholino or N-propylmorpholino.

The unsubstituted or substituted $C_{3-7}$ cycloalkyl includes $C_{3-7}$ cycloalkyl such as cyclopropyl, cyclobutyl, cyclopentyl or cyclohexyl, which may be substituted by $C_{1-4}$ alkyl such as methyl, ethyl, propyl, isopropyl, butyl, isobutyl, sec-butyl 6 or tert-butyl, halogen such as chlorine, fluorine or bromine, hydroxyl, $C_{1-4}$ alkoxy such as methoxy, ethoxy, propoxy, isopropoxy, butoxy, isobutoxy, sec-butoxy or tert-butoxy, $C_{6-10}$ aryloxy such as phenoxy, 1-naphthyloxy or 2-naphthyloxy, $C_{7-15}$ aralkyloxy such as benzyloxy, phenethyloxy, 1-naphthylmethyloxy or 2-naphthylmethyloxy, amino, mono- or di-$C_{1-4}$ alkylamino such as methylamino, ethylamino, propylamino, isopropylamino, butylamino, sec-butylamino, isobutylamino, tert-butylamino, dimethylamino or diethylamino, $C_{6-10}$ arylamino such as phenylamino, 1-naphthylamino or 2-naphthylamino, $C_{7-15}$ aralkylamino such as benzylamino, phenethylamino, 1-naphthylmethylamino or 2-naphthylmethylamino, carboxyl, formyl, $C_{2-6}$ alkoxycarbonyl such as methoxycarbonyl, ethoxycarbonyl, propoxycarbonyl, isopropoxycarbonyl, butoxycarbonyl, sec-butoxycarbonyl, isobutoxycarbonyl or tert-butoxycarbonyl, $C_{7-15}$ aryloxycarbonyl such as phenoxycarbonyl, 1-naphthyloxycarbonyl or 2-naphthyloxycarbonyl, $C_{8-15}$ aralkyloxycarbonyl such as benzyloxycarbonyl, phenethyloxycarbonyl, 1-naphthylmethyloxycarbonyl or 2-naphthylmethyloxycarbonyl, mercapto, $C_{1-4}$ alkylthio such as methylthio, ethylthio, propoylthio, isopropylthio, butylthio, sec-butylthio, isobutylthio or tert-butylthio, $C_{6-10}$ arylthio such as phenylthio, 1-naphthylthio or 2-naphthylthio, $C_{7-15}$ aralkylthio such as benzylthio, phenethylthio, 1-naphthylmethylthio or 2-naphthylmethylthio, $C_{1-4}$ alkylsulfinyl such as methylsulfinyl, ethylsulfinyl, propylsulfinyl, isopropylsulfinyl, butylsulfinyl, isobutylsulfinyl or tert-butylsulfinyl, $C_{6-10}$ arylsulfinyl such as phenylsulfinyl, 1-naphthylsulfinyl or 2-naphthylsulfinyl, $C_{7-15}$ aralkylsulfinyl such as benzylsulfinyl, phenethylsulfinyl, 1-naphthylmethylsulfinyl or 2-naphthylmethylsulfinyl, $C_{1-4}$ alkylsulfonyl such as mesyl, ethylsulfonyl, propylsulfonyl, isopropylsulfonyl, butylsulfonyl, isobutylsulfonyl, sec-butylsulfonyl or tert-butylsulfonyl, $C_{6-10}$ arylsulfonyl such as phenylsulfonyl, 1-naphthylsulfonyl or 2-naphthylsulfonyl, $C_{7-15}$ aralkylsulfonyl such as benzylsulfonyl, phenethylsulfonyl, 1-naphthylmethylsulfonyl or 2-naphthylmethylsulfonyl, or heterocyclic such as pyrolyl, furyl, thienyl, pyridyl, imidazolyl, pyrazolyl, thiazolyl, isothiazolyl, isoxazolyl, oxazolyl, pyrazinyl, pyrimidinyl, pyridazinyl, indolyl, quinolyl, isoquinolyl, phthalazinyl, naphthidinyl, quinoxalinyl, quinazolinyl, 1,4-benzodioxanyl, 1,3-benzodioxanyl, 1,2,3-triazolyl, 1,3,4-triazolyl, 1,3,4-thiadiazolyl, 1,2,3-thiadiazolyl, tetrazolyl, tetrahydrofuranyl, tetrahydrothienyl, pyrolidinyl, imidazolidinyl, 2-imidazolinyl, morpholinyl, morpholino, piperazinyl, piperidino, piperidinyl, thiomorpholino, thiomorpholinyl, morpholine-N-oxide or N-alkylmorpholino such as N-methylmorpholino, N-ethylmorpholino or N-propylmorpholino.

The unsubstituted or substituted $C_{6-10}$ aryl includes $C_{6-10}$ aryl such as phenyl, 1-naphthyl or 2-naphthyl, which may be substituted by $C_{1-4}$ alkyl such as methyl, ethyl, propyl, isopropyl, butyl, isobutyl, sec-butyl or tert-butyl, halogen such as chlorine, fluorine or bromine, nitro, hydroxyl, $C_{1-4}$ alkoxy such as methoxy, ethoxy, propoxy, isopropoxy, butoxy, isobutoxy, sec-butoxy or tert-butoxy, $C_{6-10}$ aryloxy such as phenoxy, 1-naphthyloxy or 2-naphthyloxy, $C_{7-15}$ aralkyloxy such as benzyloxy, phenethyloxy, 1-naphthylmethyloxy or 2-naphthylmethyloxy, amino, mono- or di-$C_{1-4}$ alkylamino such as methylamino, ethylamino, propylamino, isopropylamino, butylamino, sec-butylamino, isobutylamino, tert-butylamino, dimethylamino or diethylamino, $C_{6-10}$ arylamino such as phenylamino,-1-naphthylamino or 2-naphthylamino, $C_{7-15}$ aralkylamino such as benzylamino, phenethylamino, 1-naphthylmethylamino or 2-naphthylmethylamino, carboxyl, formyl, $C_{2-6}$ alkoxycarbonyl such as methoxycarbonyl, ethoxycarbonyl, propoxycarbonyl, isopropoxycarbonyl, butoxycarbonyl, sec-butoxycarbonyl, isobutoxycarbonyl or tert-butoxycarbonyl, $C_{7-15}$ aryloxycarbonyl such as phenoxycarbonyl, 1-naphthyloxycarbonyl or 2-naphthyloxycarbonyl, $C_{8-15}$ aralkyloxycarbonyl such as benzyloxycarbonyl, phenethyloxycarbonyl, 1-naphthylmethyloxycarbonyl or 2-naphthylmethyloxycarbonyl, mercapto, $C_{1-4}$ alkylthio such as methylthio, ethylthio, propylthio, isopropylthio, butylthio, sec-butylthio, isobutylthio or tert-butylthio, $C_{6-10}$ arylthio such as phenylthio, 1-naphthylthio or 2-naphthylthio, $C_{7-15}$ aralkylthio such as benzylthio, phenethylthio, 1-naphthylmethylthio or 2-naphthylmethylthio, $C_{1-4}$ alkylsulfinyl such as methylsulfinyl, ethylsulfinyl, propylsulfinyl, isopropylsulfinyl, butylsulfinyl, isobutylsulfinyl or tert-butylsulfinyl, $C_{6-10}$ arylsulfinyl such as phenylsulfinyl, 1-naphthylsulfinyl or 2-naphthylsulfinyl, $C_{7-15}$ aralkylsulfinyl such as benzylsulfinyl, phenethylsulfinyl, 1-naphthylmethylsulfinyl or 2-naphthylmethylsulfinyl, $C_{1-4}$ alkylsulfonyl such as mesyl, ethylsulfonyl, propylsulfonyl, isopropylsulfonyl, butylsulfonyl, isobutylsulfonyl, sec-butylsulfonyl or tert-butylsulfonyl, $C_{6-10}$ arylsulfonyl such as phenylsulfonyl, 1-naphthylsulfonyl or 2-naphthylsulfonyl, $C_{7-15}$ aralkylsulfonyl such as benzylsulfonyl, phenethylsulfonyl, 1-naphthylmethylsulfonyl or 2-naphthylmethylsulfonyl, or heterocyclic such as pyrolyl, furyl, thienyl, pyridyl, imidazolyl, pyrazolyl, thiazolyl, isothiazolyl, isoxazolyl, oxazolyl, pyrazinyl, pyrimidinyl, pyridazinyl, indolyl, quinolyl, isoquinolyl, phthalazinyl, naphthidinyl, quinoxalinyl, quinazolinyl, 1,4-benzodioxanyl, 1,3-benzodioxanyl, 1,2,3-triazolyl, 1,3,4-triazolyl, 1,3,4-thiadiazolyl, 1,2,3-thiadiazolyl, tetrazolyl, tetrahydrofuranyl, tetrahydrothienyl, pyrolidinyl, imidazolidinyl, 2-imidazolinyl, morpholinyl, morpholino, piperazinyl, piperidino, piperidinyl, thiomorpholino, thiomorpholinyl, morpholine-N-oxide or N-alkylmorpholino such as N-methylmorpholino, N-ethylmorpholino or N-propylmorpholino.

The unsubstituted or substituted $C_{7-15}$ aralkyl includes $C_{7-15}$ aralkyl such as benzyl, 1-naphthylmethyl, 2-naphthylmethyl, 5,6,7,8-tetrahydro-1-naphthylmethyl, 5,6,7,8-tetrahydro-2-naphthylmethyl, phenethyl, 3-phenylpropyl or 4-phenylbutyl, which may be substituted by $C_{1-4}$ alkyl such as methyl, ethyl, propyl, isopropyl, butyl, isobutyl, sec-butyl or tert-butyl, halogen such as chlorine, fluorine or bromine, nitro, hydroxyl, $C_{1-4}$ alkoxy such as methoxy, ethoxy, propoxy, isopropoxy, butoxy, isobutoxy, sec-butoxy or tert-butoxy, $C_{6-10}$ aryloxy such as phenoxy, 1-naphthyloxy or 2-naphthyloxy, $C_{7-15}$ aralkyloxy such as benzyloxy, phenethyloxy, 1-naphthylmethyloxy or 2-naphthylmethyloxy, amino, mono- or di-$C_{1-4}$ alkylamino such as methylamino, ethylamino, propylamino, isopropylamino, butylamino, sec-butylamino, isobutylamino, tert-butylamino, dimethylamino or diethylamino, $C_{6-10}$ arylamino such as phenylamino, 1-naphthylamino or 2-naphthylamino, $C_{7-10}$ aralkylamino such as benzylamino, phenethylamino, 1-naphthylmethylamino or 2-naphthylmethylamino, carboxy, formyl, $C_{2-6}$ alkoxycarbonyl such as methoxycarbonyl, ethoxycarbonyl, propoxycarbonyl, isopropoxycarbonyl, butoxycarbonyl, sec-butoxycarbonyl, isobutoxycarbonyl or tert-butoxycarbonyl, $C_{7-15}$ aryloxycarbonyl such as phenoxycarbonyl, 1-naphthyloxycarbonyl or 2-naphthyloxycarbonyl, $C_{8-15}$ aralkyloxycarbonyl such as benzyloxycarbonyl, phenethyloxycarbonyl, 1-naphthylmethyloxycarbonyl or 2-naphthylmethyloxycarbonyl, mercapto, $C_{1-4}$ alkylthio such as methylthio, ethylthio, propylthio, isopropylthio, butylthio, sec-butylthio, isobutylthio or tert-butylthio, $C_{6-10}$ arylthio such as phenylthio, naphthylthio or 2-naphthylthio, $C_{7-15}$ aralkylthio such as benzylthio, phenethylthio, 1-naphthylthio or 2-naphthylmethylthio, $C_{1-4}$ alkylsulfinyl such as methylsulfinyl, ethylsulfinyl, propylsulfinyl, isopropylsulfinyl, butylsulfinyl, isobutylsulfinyl or tert-butylsulfinyl, $C_{6-10}$ arylsulfinyl such as phenylsulfinyl, 1-naphthylsulfinyl or 2-naphthylsulfinyl, $C_{7-15}$ aralkylsulfinyl such as benzylsulfinyl, phenethylsulfinyl, 1-naphthylmethylsulfinyl or 2-naphthylmethylsulfinyl, $C_{1-4}$ alkylsulfonyl such as mesyl, ethylsulfonyl, propylsulfonyl, isopropylsulfonyl, butylsulfonyl, isobutylsulfonyl, sec-butylsulfonyl or tert-butylsulfonyl, $C_{6-10}$ arylsulfonyl such as phenylsulfonyl, 1-naphthylsulfonyl or 2-naphthylsulfonyl, $C_{7-15}$ aralkylsulfonyl such as benzylsulfonyl, phenethylsulfonyl, 1-naphthylmethylsulfonyl or 2-naphthylmethylsulfonyl, or heterocyclic such as pyrolyl, furyl, thienyl, pyridyl, imidazolyl, pyrazolyl, thiazolyl, isothiazolyl, isoxazolyl, oxazolyl, pyrazinyl, pyrimidinyl, pyridazinyl, indolyl, quinolyl, isoquinolyl, phthalazinyl, naphthidinyl, quinoxalinyl, quinazolinyl, 1,4-benzodioxanyl, 1,3-benzodioxanyl, 1,2,3-triazolyl, 1,3,4-triazolyl, 1,3,4-thiadiazolyl, 1,2,3-thiadiazolyl, tetrazolyl, tetrahydrofuranyl, tetrahydrothienyl, pyrolidinyl, imidazolidinyl, 2-imidazolinyl, morpholinyl, morpholino, piperazinyl, piperidino, piperidinyl, thiomorpholino, thiomorpholinyl, morpholine-N-oxide or N-alkylmorpholino such as N-methylmorpholino, N-ethylmorpholino or N-propylmorpholino.

The unsubstituted or substituted monocyclic or bicyclic heterocyclic containing 1 to 4 hetero-atoms selected from the group consisting of nitrogen, sulfur or oxygen includes heterocyclic such as pyrolyl, furyl, thienyl, pyridyl, imidazolyl, pyrazolyl, thiazolyl, isothiazolyl, isoxazolyl, oxazolyl, pyrazinyl, pyrimidinyl, pyridazinyl, indolyl, quinolyl, isoquinolyl, phthalazinyl, naphthidinyl, quinoxalinyl, quinazolinyl, 1,4-benzodioxanyl, 1,3-benzodioxanyl, 1,2,3-triazolyl, 1,3,4-triazolyl, 1,3,4-thiadiazoyl, 1,2,3-thiadiazolyl, tetrazolyl, tetrahydrofuranyl, tetrahydrothienyl, pyrolidinyl, imidazolidinyl, 2-imidazolinyl, morpholinyl, morpholino, piperazinyl, piperidino, piperidinyl-N-oxide, piperidinyl, piperidine-N-oxide, thiomorpholino, thiomorpholinyl, morpholine-N-oxide or N-alkylmorpholino such as N-methylmorpholino, N-ethylmorpholino or N-propylmorpholino, which may be substituted by $C_{1-4}$ alkyl such as methyl, ethyl, propyl, isopropyl, butyl, isobutyl, sec-butyl or tert-butyl, halogen such as chlorine, fluorine or bromine, nitro, hydroxyl, $C_{1-4}$ alkoxy such as methoxy, ethoxy, propoxy, isopropoxy, butoxy, isobutoxy, sec-butoxy or tert-butoxy, $C_{6-10}$ aryloxy such as phenoxy, 1-naphthyloxy or 2-naphthyloxy, $C_{7-15}$ aralkyloxy such as benzyloxy, phenethyloxy, 1-naphthylmethyloxy or 2-naphthylmethyloxy, amino, mono- or di- $C_{1-4}$ alkylamino such as methylamino, ethylamino, propylamino, isopropylamino, butylamino, sec-butylamino, isobutylamino, tert-butylamino, dimethylamino or diethylamino, $C_{6-10}$ arylamino such as phenylamino, 1-naphthylamino or 2-naphthylamino, $C_{7-15}$ aralkylamino such as benzylamino, phenethylamino, 1-naphthylmethylamino or 2-naphthylmethylamino, carboxyl, formyl, $C_{2-6}$ alkoxycarbonyl such as methoxycarbonyl, ethoxycarbonyl, propoxycarbonyl, isopropoxycarbonyl, butoxycarbonyl, sec-butoxycarbonyl, isobutoxycarbonyl or tert-butoxycarbonyl, $C_{7-15}$ aryloxycarbonyl such as phenoxycarbonyl, 1-naphthyloxycarbonyl or 2-naphthyloxycarbonyl, $C_{8-15}$ aralkyloxycarbonyl such as benzyloxycarbonyl, phenethyloxycarbonyl, 1-naphthylmethyloxycarbonyl or 2-naphthylmethyloxycarbonyl, mercapto, $C_{1-4}$ alkylthio such as methylthio, ethylthio, propylthio, isopropylthio, butylthio, sec-butylthio, isobutylthio or tert-butylthio, $C_{6-10}$ arylthio such as phenylthio, 1-naphthylthio or 2-naphthylthio, $C_{7-15}$ aralkylthio such as benzylthio, phenethylthio, 1-naphthylmethylthio or 2-naphthylmethylthio, $C_{1-4}$ alkylsulfinyl such as methylsulfinyl, ethylsulfinyl, propylsulfinyl, isopropylsulfinyl, butylsulfinyl, isobutylsulfinyl or tert-butylsulfinyl, $C_{6-10}$ arylsulfinyl such as phenylsulfinyl, 1-naphthylsulfinyl or 2-naphthylsulfinyl, $C_{7-15}$ aralkylsulfinyl such as benzylsulfinyl, phenethylsulfinyl, 1-naphthylmethylsulfinyl or 2-naphthylmethylsulfinyl, $C_{1-4}$ alkylsulfonyl such as mesyl, ethylsulfonyl, propylsulfonyl, isopropylsulfonyl, butylsulfonyl, isobutylsulfonyl, sec-butylsulfonyl or tert-butylsulfonyl, $C_{6-10}$ arylsulfonyl such as phenylsulfonyl, 1-naphthylsulfonyl or 2-naphthylsulfonyl, or $C_{7-15}$ aralkylsulfonyl such as benzylsulfonyl, phenethylsulfonyl, 1-naphthylmethylsulfonyl or 2-naphthylmethylsulfonyl.

In $—N(Y^4)(Y^5)$ (wherein $Y^4$ and $Y^5$ are as defined above), the 5-or 6-membered heterocyclic which is formed by $Y^4$ and $Y^5$ together with the adjacent nitrogen atom and may further contain other hetero-atoms selected from the group consisting of nitrogen, oxygen and sulfur, includes heterocyclic such as morpholino, thiomorpholino, piperidino, pyrolidinyl, piperazinyl.

The $C_{3-9}$ alkoxycarbonyloxyalkyl includes $C_{3-9}$ alkyloxycarbonylalkyl such as methoxycarbonyloxymethyl, ethoxycarbonyloxymethyl, propoxycarbonyloxymethyl, isopropoxycarbonyloxymethyl, butoxycarbonyloxymethyl, tert-butoxycarbonyloxymethyl, 1-methoxycarbonylmethyl, 2-methoxycarbonyloxyethyl, 1-ethoxycarbonyloxyethyl, 2-ethoxycarbonyloxyethyl, 1-tert-butoxycarbonyloxyethyl, 2-tert-butoxycarbonyloxyethyl, 1-butoxycarbonyloxyethyl, 1-pentylcarbonyloxyethyl or 1-hexylcarbonyloxyethyl.

In the compound of the formula I of the present invention, the asymmetric carbon atoms may have R-configuration, S-configuration or RS-configuration.

The salt of the compound of the present invention may be any pharmaceutically acceptable non-toxic salt. For example, it may be a salt with anion such as $F^\ominus$, $Cl^\ominus$, $Br^\ominus$ or $I^\ominus$ with an inorganic acid such as hydrochloric acid, sulfuric acid, hydriodic acid, hydrobromic acid or phosphoric acid, or a salt with an organic acid such as oxalic acid, maleic acid, acetic acid, formic acid or tartaric acid.

Representative compounds of the present invention are listed in Table, wherein Me means methyl, Et ethyl, i-Pr isopropyl, n-Bu n-butyl, i-Bu isobutyl, t-Bu tert-butyl, Ac acetyl, Ph phenyl and Naph-CH$_2$-1-naphthylmethyl, and E' indicates the steric configuration (R, S or RS).

$$R^{1'}-\underset{\underset{(O)_{m'}}{\|}}{S}-CH_2-\underset{(S)}{\overset{\overset{R^{2'}}{|}}{CH}}-CONH-\underset{(S)}{\overset{\overset{R^{4'}}{|}}{CH}}-CONH-\underset{(S)}{\overset{\overset{R^{6'}}{|}}{CH}}-\underset{(R)}{\overset{\overset{OH}{|}}{CH}}-\underset{(E')}{\overset{\overset{OH}{|}}{CH}}-CH_2-R^{7'}$$

| R[1'] | R[2'] | R[4'] | R[6'] | R[7'] | m' | E' |
|---|---|---|---|---|---|---|
| AcOCH₂CH(OAc)CH₂— | Naph-CH₂— | n-Bu | Cyclohexyl-CH₂— | Morpholino-N— | 2 | S |
| t-Bu-COOCH₂CH(OH)CH₂— | " | " | " | " | " | " |
| AcO(CH₂)₂— | " | " | " | " | " | " |
| t-Bu-COO(CH₂)₂— | " | " | " | " | " | " |
| EtOCOO(CH₂)₂— | " | " | " | " | " | " |
| AcOCH₂CH(OAc)CH₂— | " | " | " | " | 1 | " |
| " | " | " | " | " | 0 | " |
| AcOCH₂CH(OH)CH₂— | " | " | " | " | 2 | " |
| EtCOOCH₂CH(OH)CH₂— | " | " | " | " | " | " |
| EtCOOCH₂CH(OCOEt)CH₂— | " | " | " | " | " | " |
| EtCOOCH₂CH(OMe)CH₂— | " | " | " | " | " | " |
| AcOCH₂CH(OMe)CH₂— | " | " | " | " | " | " |
| EtCOOCH₂CH(OAc)CH₂— | " | " | " | " | " | " |
| AcOCH₂CH(OH)CH₂— | " | " | " | " | 0 | " |
| EtCOOCH₂CH(OH)CH₂— | " | " | " | " | " | " |
| EtCOOCH₂CH(OCOEt)CH₂— | Naph-CH₂— | n-Bu | Cyclohexyl-CH₂— | Morpholino-N— | 0 | S |
| EtCOOCH₂CH(OMe)CH₂— | " | " | " | " | " | " |
| AcOCH₂CH(OMe)CH₂— | " | " | " | " | " | " |
| EtCOOCH₂CH(OAc)CH₂— | " | " | " | " | " | " |
| HO-cyclopentyl(OAc)- | " | " | " | " | 2 | " |
| AcO-cyclopentyl(OH)- | " | " | " | " | " | " |
| HO-cyclopentyl(OCOEt)- | " | " | " | " | " | " |
| EtCOO-cyclopentyl(OH)- | " | " | " | " | " | " |
| AcO-cyclopentyl(OAc)- | " | " | " | " | " | " |
| EtCOO-cyclopentyl(OCOEt)- | " | " | " | " | " | " |
| EtCOO-cyclopentyl(OMe)- | Naph-CH₂— | n-Bu | Cyclohexyl-CH₂— | Morpholino-N— | 2 | S |

-continued $$R^{1'}-\underset{\underset{(O)_{m'}}{\|}}{S}-CH_2-\underset{(S)}{\overset{R^{2'}}{CH}}-CONH-\underset{(S)}{\overset{R^{4'}}{CH}}-CONH-\underset{(S)}{\overset{R^{6'}}{CH}}-\underset{(R)}{\overset{OH}{CH}}-\underset{(E')}{\overset{OH}{CH}}-CH_2-R^{7'}$$

| R¹' | R²' | R⁴' | R⁶' | R⁷' | m' | E' |
|---|---|---|---|---|---|---|
| AcO—[cyclopentane with OMe]— | " | " | " | " | " | " |
| MeO—[cyclopentane with OCOEt]— | " | " | " | " | " | " |
| MeO—[cyclopentane with OAc]— | " | " | " | " | " | " |
| AcOCH₂CH(OAc)CH₂— | " | HN—[imidazole]—CH₂— | " | " | " | " |
| t-Bu-COOCH₂CH(OH)CH₂— | " | " | " | " | " | " |
| AcO(CH₂)₂— | " | " | " | " | " | " |
| t-Bu-COO(CH₂)₂— | " | " | " | " | " | " |
| EtOCOO(CH₂)₂— | " | " | " | " | 1 | " |
| " | " | " | " | " | 0 | " |
| AcOCH₂CH(OH)CH₂— | " | " | " | " | 2 | " |
| EtCOOCH₂CH(OH)CH₂— | " | " | " | " | " | " |
| EtCOOCH₂CH(OCOEt)CH₂— | " | " | " | " | " | " |
| EtCOOCH₂CH(OMe)CH₂— | " | " | " | " | " | " |
| AcO—[cyclopentane]— | Naph-CH₂— | n-Bu | i-Bu | O[morpholine]N— | 2 | S |
| " | " | " | " | cyclohexyl-CH₂— | 0 | " |
| [cyclopentane with OAc]— | " | " | " | " | 2 | " |
| [cyclopentane with OAc, OAc]— | " | " | " | " | " | " |
| AcO—[furanose sugar with acetonide]— | PhCH₂— | " | " | " | " | " |
| AcOCH₂C(=NOMe)CH₂— | Naph-CH₂ | " | " | " | " | " |
| AcOCH₂C(=NOH)CH₂— | " | " | " | " | " | " |
| AcOCH₂CH(OEt)CH₂— | " | " | " | " | " | " |

-continued $$R^{1'}-\underset{\underset{(O)_{m'}}{\|}}{S}-CH_2-\underset{(S)}{\overset{R^{2'}}{C}H}-CONH-\underset{(S)}{\overset{R^{4'}}{C}H}-CONH-\underset{(S)}{\overset{R^{6'}}{C}H}-\underset{(R)}{\overset{OH}{C}H}-\underset{(E')}{\overset{OH}{C}H}-CH_2-R^{7'}$$

| $R^{1'}$ | $R^{2'}$ | $R^{4'}$ | $R^{6'}$ | $R^{7'}$ | m' | E' |
|---|---|---|---|---|---|---|
| AcOCH₂CH(OMe)CH₂— | " | thiazole-CH₂— | " | " | " | " |
| MeO-sugar(OAc,OAc) | PhCH₂— | n-Bu | cyclohexyl-CH₂— | morpholino-N— | 0 | S |
| " | " | " | " | " | 1 | " |
| " | " | imidazole-CH₂— | " | " | 2 | " |
| " | " | " | " | " | 0 | " |
| " | " | " | " | " | 1 | " |
| " | Naph-CH₂— | n-Bu | " | " | 2 | " |
| " | " | " | " | " | 0 | " |
| " | " | " | " | " | 1 | " |
| AcOCH₂CH(OMe)CH₂— | " | " | i-Bu | " | 0 | " |
| MeOCH₂CH(OAc)CH₂— | " | " | " | " | 2 | " |
| AcOCH₂CH(OMe)CH₂— | " | " | " | " | " | " |
| AcO(CH₂)₂— | " | imidazole-CH₂— | " | " | " | " |
| " | " | " | " | " | 0 | " |
| MeO-sugar(OAc,OAc,OAc) | Naph-CH₂— | n-Bu | cyclohexyl-CH₂— | morpholino-N— | 2 | S |
| " | " | " | " | " | 0 | " |
| " | " | " | " | " | 1 | " |
| MeO-sugar(OAc,OAc) | PhCH₂— | " | " | " | 2 | " |
| " | " | " | " | " | 0 | " |
| " | " | " | " | " | 1 | " |
| " | " | imidazole-CH₂— | " | " | 2 | " |
| " | " | " | " | " | 0 | " |
| " | " | " | " | " | 1 | " |
| " | Naph-CH₂— | n-Bu | " | " | 2 | " |
| " | " | " | " | " | 0 | " |
| " | " | " | " | " | 1 | " |

-continued $$R^{1'}-\underset{\underset{(O)_{m'}}{\|}}{S}-CH_2-\underset{(S)}{\overset{R^{2'}}{CH}}-CONH-\underset{(S)}{\overset{R^{4'}}{CH}}-CONH-\underset{(S)}{\overset{R^{6'}}{CH}}-\underset{(R)}{\overset{OH}{CH}}-\underset{(E')}{\overset{OH}{CH}}-CH_2-R^{7'}$$

| $R^{1'}$ | $R^{2'}$ | $R^{4'}$ | $R^{6'}$ | $R^{7'}$ | m' | E' |
|---|---|---|---|---|---|---|
| MeO-furanose(OAc)(OAc) | PhCH₂— | " | " | " | 2 | " |
| HO-furanose(OAc)(OAc) | PhCH₂— | HN-imidazolyl-CH₂— | cyclohexyl-CH₂— | morpholino-N— | 0 | R |
| " | " | " | " | " | 1 | " |
| " | Naph-CH₂— | n-Bu | " | " | 2 | " |
| " | " | " | " | " | 0 | " |
| " | " | " | " | " | 1 | " |
| MeO-furanose(OAc)(OAc) | PhCH₂— | " | " | " | 2 | " |
| " | " | " | " | " | 0 | " |
| " | " | " | " | " | 1 | " |
| " | " | HN-imidazolyl-CH₂— | " | " | 2 | " |
| " | " | " | " | " | 0 | " |
| " | " | " | " | " | 1 | " |
| HO-furanose(OAc)(AcO) | PhCH₂— | n-Bu | cyclohexyl-CH₂— | morpholino-N— | 2 | S |
| " | " | " | " | " | 0 | " |
| " | " | " | " | " | 1 | " |
| " | " | HN-imidazolyl-CH₂— | " | " | 2 | O |
| " | " | " | " | " | 0 | " |
| " | " | " | " | " | 1 | " |
| " | Naph-CH₂— | n-Bu | " | " | 2 | " |
| " | " | " | " | " | 0 | " |
| " | " | " | " | " | 1 | " |
| HO-furanose(OAc)(OAc) | PhCH₂— | " | " | " | 2 | " |
| " | " | " | " | " | 0 | " |
| " | " | " | " | " | 1 | " |

-continued $$R^{1'}-\underset{(O)_{m'}}{S}-CH_2-\underset{(S)}{\overset{R^{2'}}{CH}}-CONH-\underset{(S)}{\overset{R^{4'}}{CH}}-CONH-\underset{(S)}{\overset{R^{6'}}{CH}}-\underset{(R)}{\overset{OH}{CH}}-\underset{(E')}{\overset{OH}{CH}}-CH_2-R^{7'}$$

| R¹' | R²' | R⁴' | R⁶' | R⁷' | m' | E' |
|---|---|---|---|---|---|---|
| " | " | imidazol-4-yl-CH₂— | " | " | 2 | " |
| triacetyl-furanose (OAc, OAc, AcO) | PhCH₂— | imidazol-4-yl-CH₂— | cyclohexyl-CH₂— | morpholino | 0 | S |
| " | " | " | " | " | 1 | " |
| " | Naph-CH₂— | n-Bu | " | " | 2 | " |
| " | " | " | " | " | 0 | " |
| " | " | " | " | " | 1 | " |
| HO-furanose (OAc, AcO) | PhCH₂— | " | " | " | 0 | " |
| " | " | " | " | " | 1 | " |
| " | " | imidazol-4-yl-CH₂— | " | " | 2 | " |
| " | " | " | " | " | 0 | " |
| " | " | " | " | " | 1 | " |
| " | Naph-CH₂— | n-Bu | " | " | 2 | " |
| " | " | " | " | " | 0 | " |
| " | " | " | " | " | 1 | " |
| AcO-furanose (OAc, OAc) | PhCH₂— | n-Bu | cyclohexyl-CH₂— | morpholino | 2 | S |
| " | " | " | " | " | 0 | " |
| " | " | " | " | " | 1 | " |
| " | Naph-CH₂— | " | " | " | 2 | " |
| " | " | " | " | " | 0 | " |
| " | " | " | " | " | 1 | " |
| " | " | imidazol-4-yl-CH₂— | " | " | 2 | " |
| " | " | " | " | " | 0 | " |
| " | " | " | " | " | 1 | " |
| triacetyl-furanose (OAc, OAc, AcO) | PhCH₂— | n-Bu | " | " | 2 | " |
| " | " | " | " | " | 0 | " |
| " | " | " | " | " | 1 | " |

-continued $$R^{1'}-\underset{\underset{(O)_{m'}}{\|}}{S}-CH_2-\underset{(S)}{\overset{R^{2'}}{C}H}-CONH-\underset{(S)}{\overset{R^{4'}}{C}H}-CONH-\underset{(S)}{\overset{R^{6'}}{C}H}-\underset{(R)}{\overset{OH}{C}H}-\underset{(E')}{\overset{OH}{C}H}-CH_2-R^{7'}$$

| $R^{1'}$ | $R^{2'}$ | $R^{4'}$ | $R^{6'}$ | $R^{7'}$ | m' | E' |
|---|---|---|---|---|---|---|
| " | " | HN–CH=C(CH$_2$–)–N= (imidazolyl-CH$_2$–) | " | " | 2 | " |
| AcO-ribose(OAc)$_3$ | Naph-CH$_2$– | n-Bu | cyclohexyl-CH$_2$– | morpholino-N– | 1 | S |
| " | " | imidazolyl-CH$_2$– | " | " | 2 | " |
| " | " | " | " | " | 0 | " |
| " | " | " | " | " | 1 | " |
| AcO-deoxyribose(OAc)$_2$ | " | n-Bu | " | " | 2 | " |
| " | " | " | " | " | 0 | " |
| " | PhCH$_2$– | " | " | " | 1 | " |
| " | " | " | " | " | 2 | " |
| " | " | " | " | " | 0 | " |
| " | " | " | " | " | 1 | " |
| " | " | imidazolyl-CH$_2$– | " | " | 2 | " |
| " | " | " | " | " | 0 | " |
| " | " | " | " | " | 1 | " |
| EtCOOCH$_2$CH(OAc)CH$_2$– | Naph-CH$_2$– | imidazolyl-CH$_2$– | cyclohexyl-CH$_2$– | i-Pr–S(O)$_2$– | 2 | R |
| AcO-C$_6$H$_4$– | " | n-Bu | " | morpholino-N– | 0 | S |
| " | " | " | " | " | 2 | " |
| " | " | " | " | " | 1 | " |
| AcOCH$_2$CH(OAc)CH$_2$ | " | imidazolyl-CH$_2$– | " | " | 2 | " |
| " | " | n-Bu | i-Bu | i-Pr–S– | " | R |
| " | " | " | " | i-Pr–S(O)$_2$– | " | " |

-continued $$R^{1'}-S(O)_{m'}-CH_2-\underset{(S)}{\underset{|}{CH}}-CONH-\underset{(S)}{\underset{|}{CH}}-CONH-\underset{(S)}{\underset{|}{CH}}-\underset{(R)}{\underset{|}{CH}}-\underset{(E')}{\underset{|}{CH}}-CH_2-R^{7'}$$

| $R^{1'}$ | $R^{2'}$ | $R^{4'}$ | $R^{6'}$ | $R^{7'}$ | m' | E' |
|---|---|---|---|---|---|---|
| 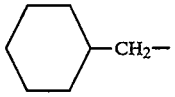 | PhCH₂— | " | 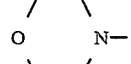CH₂— | 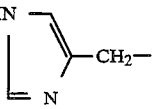 | " | S |
| " | " | " | " | " | 0 | " |
| " | " | " | " | " | 1 | " |
| " | Naph-CH₂— | " | " | " | 2 | " |
| " | " | " | " | " | 0 | " |
| EtCOOCH₂CH(OMe)CH₂— | Naph-CH₂— | 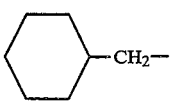CH₂— | 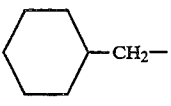CH₂— | i-Pr—S— | 2 | R |
| AcOCH₂CH(OMe)CH₂— | " | " | " | " | " | " |
| EtCOOCH₂CH(OAc)CH₂— | " | " | " | " | " | " |
| AcOCH₂CH(OAc)CH₂— | " | " | " | i-Pr—S(O)₂— | " | " |
| t-Bu-COOCH₂CH(OH)CH₂— | " | " | " | " | " | " |
| AcO(CH₂)₂— | " | " | " | " | " | " |
| t-Bu-COO(CH₂)₂— | " | " | " | " | " | " |
| EtOCOO(CH₂)₂— | " | " | " | " | " | " |
| AcOCH₂CH(OAc)CH₂— | " | " | " | " | 1 | " |
| " | " | " | " | " | 2 | " |
| AcOCH₂CH(OH)CH₂— | " | " | " | " | " | " |
| EtCOOCH₂CH(OH)CH₂— | " | " | " | " | " | " |
| EtCOOCH₂CH(OCOEt)CH₂— | " | " | " | " | " | " |
| EtCOOCH₂CH(OMe)CH₂— | " | " | " | " | " | " |
| AcOCH₂CH(OMe)CH₂ | " | " | " | " | " | " |
| AcOCH₂CH(OAc)CH₂— | Naph-CH₂— | t-Bu | 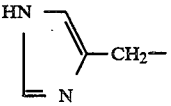CH₂— | i-Pr—S— | 0 | R |
| AcOCH₂CH(OH)CH₂— | " | " | " | " | 2 | " |
| EtCOOCH₂CH(OH)CH₂— | " | " | " | " | " | " |
| EtCOOCH₂CH(OCOEt)CH₂— | " | " | " | " | " | " |
| EtCOOCH₂CH(OMe)CH₂— | " | " | " | " | " | " |
| AcOCH₂CH(OMe)CH₂— | " | " | " | " | " | " |
| EtCOOCH₂CH(OAc)CH₂— | " | " | " | " | " | " |
| AcOCH₂CH(OAc)CH₂— | " | 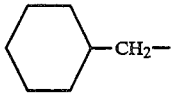CH₂— | " | " | " | " |
| t-Bu-COOCH₂CH(OH)CH₂— | " | " | " | " | " | " |
| AcO(CH₂)₂— | " | " | " | " | " | " |
| t-Bu-COO(CH₂)₂— | " | " | " | " | " | " |
| EtOCOO(CH₂)₂— | " | " | " | " | " | " |
| AcOCH₂CH(OAc)CH₂— | " | " | " | " | 1 | " |
| " | " | " | " | " | 0 | " |
| AcOCH₂CH(OH)CH₂— | " | " | " | " | 2 | " |
| EtCOOCH₂CH(OH)CH₂— | " | " | " | " | " | " |
| EtCOOCH₂CH(OCOEt)CH₂— | " | " | " | " | " | " |
| AcO(CH₂)₂— | Naph-CH₂— | t-Bu | 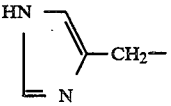CH₂— | i-Pr—S— | 2 | R |
| t-Bu-COO(CH₂)₂— | " | " | " | " | " | " |

-continued $$R^{1'}-\underset{\underset{(O)_{m'}}{\|}}{S}-CH_2-\underset{\underset{(S)}{|}}{\overset{R^{2'}}{C}H}-CONH-\underset{(S)}{CH}-CONH-\underset{(S)}{\overset{R^{6'}}{C}H}-\underset{(R)}{\overset{OH}{C}H}-\underset{(E')}{\overset{OH}{C}H}-CH_2-R^{7'}$$

| $R^{1'}$ | $R^{2'}$ | $R^{4'}$ | $R^{6'}$ | $R^{7'}$ | $m'$ | $E'$ |
|---|---|---|---|---|---|---|
| EtOCOO(CH$_2$)$_2$— | " | " | " | " | " | " |
| AcOCH$_2$CH(OAc)CH$_2$— | " | " | " | " | 1 | " |
| " | " | " | " | " | 0 | " |
| AcOCH$_2$CH(OH)CH$_2$— | " | " | " | " | 2 | " |
| EtCOOCH$_2$CH(OH)CH$_2$— | " | " | " | " | " | " |
| EtCOOCH$_2$CH(OCOEt)CH$_2$— | " | t-Bu | " | " | " | " |
| EtCOOCH$_2$CH(OMe)CH$_2$— | " | " | " | " | " | " |
| AcOCH$_2$CH(OMe)CH$_2$— | " | " | " | " | " | " |
| EtCOOCH$_2$CH(OAc)CH$_2$— | " | " | " | " | " | " |
| AcOCH$_2$CH(OAc)CH$_2$— | Naph-CH$_2$— | " | " | " | " | " |
| t-Bu-COOCH$_2$CH(OH)CH$_2$— | " | " | " | " | " | " |
| AcO(CH$_2$)$_2$— | " | " | " | " | " | " |
| t-Bu-COO(CH$_2$)$_2$— | " | " | " | " | " | " |
| EtOCOO(CH$_2$)$_2$— | " | " | " | " | " | " |
| AcOCH$_2$CH(OAc)CH$_2$— | " | " | " | " | 1 | " |
| HO–[cyclopentyl-OCOEt-Me] | PhCH$_2$— | HN=CH–C(=N)–CH$_2$– (imidazolyl-CH$_2$) | cyclohexyl-CH$_2$— | morpholino-N— | 2 | S |
| EtCOO–[cyclopentyl-OH-Me] | " | " | " | " | " | " |
| AcO–[cyclopentyl-OAc-Me] | " | " | " | " | " | " |
| EtCOO–[cyclopentyl-OCOEt-Me] | " | " | " | " | " | " |
| EtCOO–[cyclopentyl-OMe-Me] | " | " | " | " | " | " |
| AcO–[cyclopentyl-OMe-Me] | " | " | " | " | " | " |
| MeO–[cyclopentyl-OCOEt-Me] | " | " | " | " | " | " |
| MeO–[cyclopentyl-OAc-Me] | " | " | " | " | " | " |
| AcOCH$_2$CH(OAc)CH$_2$— | " | n-Bu | " | i-Pr—S— | " | R |
| t-Bu-COOCH$_2$CH(OH)CH$_2$— | " | " | " | " | " | " |
| AcOCH$_2$CH(OAc)CH$_2$— | PhCH$_2$— | HN=CH–C(=N)–CH$_2$– (imidazolyl-CH$_2$) | cyclohexyl-CH$_2$— | morpholino-N— | 1 | S |

-continued $$R^{1'}-\underset{(O)_{m'}}{\overset{\|}{S}}-CH_2-\underset{(S)}{\overset{R^{2'}}{\underset{|}{CH}}}-CONH-\underset{(S)}{\overset{R^{4'}}{\underset{|}{CH}}}-CONH-\underset{(S)}{\overset{R^{6'}}{\underset{|}{CH}}}-\underset{(R)}{\overset{OH}{\underset{|}{CH}}}-\underset{(E')}{\overset{OH}{\underset{|}{CH}}}-CH_2-R^{7'}$$

| R$^{1'}$ | R$^{2'}$ | R$^{4'}$ | R$^{6'}$ | R$^{7'}$ | m' | E' |
|---|---|---|---|---|---|---|
| " | " | " | " | " | 0 | " |
| AcOCH$_2$CH(OH)CH$_2$— | " | " | " | " | 2 | " |
| EtCOOCH$_2$CH(OH)CH$_2$— | " | " | " | " | " | " |
| EtCOOCH$_2$CH(OCOEt)CH$_2$— | " | " | " | " | " | " |
| EtCOOCH$_2$CH(OMe)CH$_2$— | " | " | " | " | " | " |
| AcOCH$_2$CH(OMe)CH$_2$— | " | " | " | " | " | " |
| EtCOOCH$_2$CH(OAc)CH$_2$— | " | " | " | " | " | " |
| AcOCH$_2$CH(OH)CH$_2$— | " | " | " | " | 0 | " |
| EtCOOCH$_2$CH(OH)CH$_2$— | " | " | " | " | " | " |
| EtCOOCH$_2$CH(OCOEt)CH$_2$— | " | " | " | " | " | " |
| EtCOOCH$_2$CH(OMe)CH$_2$— | " | " | " | " | " | " |
| AcOCH$_2$CH(OMe)CH$_2$— | " | " | " | " | " | " |
| EtCOOCH$_2$CH(OAc)CH$_2$— | " | " | " | " | " | " |
| HO-cyclopentyl(OAc)- | " | " | " | " | 2 | " |
| AcO-cyclopentyl(OH)- | " | " | " | " | " | " |
| HO-cyclopentyl(OCOEt)- | PhCH$_2$— | n-Bu | cyclohexyl-CH$_2$— | morpholino-N— | 2 | S |
| EtCOO-cyclopentyl(OH)- | " | t-bu | " | " | " | " |
| AcO-cyclopentyl(OAc)- | " | " | " | " | " | " |
| EtCOO-cyclopentyl(OCOEt)- | " | " | " | " | " | " |
| EtCOO-cyclopentyl(OMe)- | " | " | " | " | " | " |
| AcO-cyclopentyl(OMe)- | " | " | " | " | " | " |
| MeO-cyclopentyl(OCOEt)- | " | " | " | " | " | " |

-continued $$R^{1'}-\underset{\underset{(O)_{m'}}{\|}}{S}-CH_2-\underset{(S)}{\overset{R^{2'}}{CH}}-CONH-\underset{(S)}{\overset{R^{4'}}{CH}}-CONH-\underset{(S)}{\overset{R^{6'}}{CH}}-\underset{(R)}{\overset{OH}{CH}}-\underset{(E')}{\overset{OH}{CH}}-CH_2-R^{7'}$$

| R¹' | R²' | R⁴' | R⁶' | R⁷' | m' | E' |
|---|---|---|---|---|---|---|
| MeO—[cyclopentane with OAc] | " | " | " | " | " | " |
| AcOCH₂CH(OAc)CH₂— | " | HN—[imidazole]—CH₂— | " | " | " | " |
| t-Bu-COOCH₂CH(OH)CH₂— | " | " | " | " | " | " |
| AcO(CH₂)₂— | " | " | " | " | " | " |
| t-Bu-COO(CH₂)₂— | " | " | " | " | " | " |
| EtOCOO(CH₂)₂— | " | " | " | " | " | " |
| AcOCH₂CH(OAc)CH₂— | PhCH₂— | n-Bu | [cyclohexyl]-CH₂— | [morpholino]N— | 0 | S |
| AcOCH₂CH(OH)CH₂— | " | " | " | " | 2 | " |
| EtCOOCH₂CH(OH)CH₂— | " | " | " | " | " | " |
| EtCOOCH₂CH(OCOEt)CH₂— | " | " | " | " | " | " |
| EtCOOCH₂CH(OMe)CH₂— | " | " | " | " | " | " |
| AcOCH₂CH(OMe)CH₂— | " | " | " | " | " | " |
| EtCOOCH₂CH(OAc)CH₂— | " | " | " | " | " | " |
| AcOCH₂CH(OH)CH₂— | " | " | " | " | 0 | " |
| EtCOOCH₂CH(OH)CH₂— | " | " | " | " | " | " |
| EtCOOCH₂CH(OCOEt)CH₂— | " | " | " | " | " | " |
| EtCOOCH₂CH(OMe)CH₂— | " | " | " | " | " | " |
| AcOCH₂CH(OMe)CH₂— | " | " | " | " | " | " |
| EtCOOCH₂CH(OAc)CH₂— | " | " | " | " | " | " |
| HO—[cyclopentane with OAc]— | " | " | " | " | 2 | " |
| AcO—[cyclopentane with OH]— | " | " | " | " | " | " |
| AcO—[cyclopentane with OAc]— | Naph-CH₂— | HN—[imidazole]—CH₂— | [cyclohexyl]-CH₂— | [morpholino]N— | 2 | S |
| EtCOO—[cyclopentane with OCOEt]— | " | " | " | " | " | " |
| EtCOO—[cyclopentane with OMe]— | " | " | " | " | " | " |
| AcO—[cyclopentane with OMe]— | " | " | " | " | " | " |

-continued $$R^{1'}-\underset{\underset{(O)_{m'}}{\|}}{S}-CH_2-\underset{\underset{(S)}{|}}{\overset{R^{2'}}{CH}}-CONH-\underset{(S)}{\overset{R^{4'}}{\underset{|}{CH}}}-CONH-\underset{(S)}{\overset{R^{6'}}{\underset{|}{CH}}}-\underset{(R)}{\overset{OH}{\underset{|}{CH}}}-\underset{(E')}{\overset{OH}{\underset{|}{CH}}}-CH_2-R^{7'}$$

| R¹' | R²' | R⁴' | R⁶' | R⁷' | m' | E' |
|---|---|---|---|---|---|---|
| MeO⟨OCOEt⟩ (cyclopentane) | " | " | " | " | " | " |
| MeO⟨OAc⟩ (cyclopentane) | " | " | " | " | " | " |
| AcOCH₂CH(OAc)CH₂— | PhCH₂— | n-Bu | " | " | " | " |
| t-Bu-COOCH₂CH(OH)CH₂— | " | " | " | " | " | " |
| AcO(CH₂)₂— | " | " | " | " | " | " |
| t-Bu-COO(CH₂)₂— | " | " | " | " | " | " |
| EtOCOO(CH₂)₂— | " | " | " | " | " | " |
| AcOCH₂CH(OAc)CH₂— | " | " | " | " | 1 | " |
| AcOCH₂CH(OMe)CH₂— | Naph-CH₂— | HN—CH=N imidazolyl-CH₂— | cyclohexyl-CH₂— | morpholino-N— | 2 | S |
| EtCOOCH₂CH(OAc)CH₂— | " | " | " | " | " | " |
| AcOCH₂CH(OH)CH₂— | " | " | " | " | 0 | " |
| EtCOOCH₂CH(OH)CH₂— | " | " | " | " | " | " |
| EtCOOCH₂CH(OCOEt)CH₂— | " | " | " | " | " | " |
| EtCOOCH₂CH(OMe)CH₂— | " | " | " | " | " | " |
| AcOCH₂CH(OMe)CH₂— | " | " | " | " | " | " |
| EtCOOCH₂CH(OAc)CH₂— | " | " | " | " | " | " |
| HO⟨OAc⟩ (cyclopentane) | " | " | " | " | 2 | " |
| AcO⟨OH⟩ (cyclopentane) | " | " | " | " | " | " |
| HO⟨OCOEt⟩ (cyclopentane) | " | " | " | " | " | " |
| EtCOO⟨OH⟩ (cyclopentane) | " | " | " | " | " | " |

Now, the process for the preparation of the compound of the formula I of the present invention will be described.

In the following formulas, R¹, R², R³, R⁴, R⁵, R⁶, m, n and A are as defined above, and T is a leaving group.

Basically, the N-substituted acylamino acid compound of the formula I of the present invention can be prepared by condensing an N-acylamino acid of the formula:

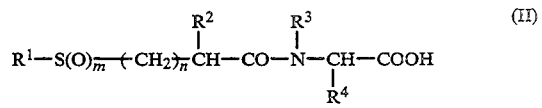

or a reactive derivative at the carboxyl group thereof with an amine of the formula:

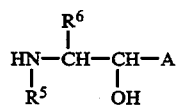
(III)

or condensing a carboxylic acid of the formula:

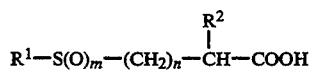
(IV)

or a reactive derivative at the carboxyl group thereof with an amino acid amide of the formula:

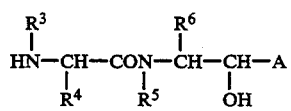
(V)

The condensation of the compounds of the formulas II and III or the condensation of the compounds of the formulas IV and V can be conducted by a usual method for the synthesis of a peptide, such as an azide method, an active ester method, a mixed acid anhydride method, a carbodiimide method, an imidazole method, a diphenylphosphoryl azide method, a Woodward method or condensation method in an oxidation and reduction system.

When a functional group which may adversely affect the condensation reaction, such as an amino group, or a carboxyl group, is present, such a functional group may be protected and then condensed, and the protecting group is then removed to obtain the compound of the present invention. Such a condensation method, protection of a functional group and removal of the functional group are disclosed in detail, for example, in "Basic for the Peptide Synthesis and Experiments" edited by Nobuo Izumiya et al, Maruzen (1985), "Protein Chemistry" edited by Shiro Akabori et al, Kyoritsu Shuppan (1969), or "Chemistry of the Amino Acids" edited by J. P. Greenstein and M. Winitz, John Wiley & Sons, Inc. (1961).

The compound of the formula II can be prepared by the process shown by reaction scheme I.

Reaction scheme 1

1. Step of alkylation or arylation $$CH_2(CO_2R)_2 \quad (1)$$

$$R^2-CH(CO_2R)_2 \quad (2)$$

2. Step of saponification

(3)

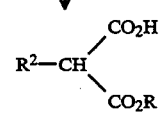

3. Step of condensation

-continued
Reaction scheme 1

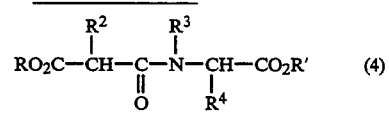
(4)

4. Step of increasing carbon atoms

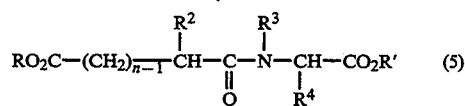
(5)

5. Step of reduction

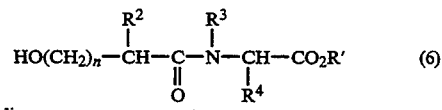
(6)

6. Step of bonding a leaving group

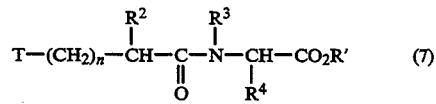
(7)

7. Step of thioetherification $\quad R^1-SH$

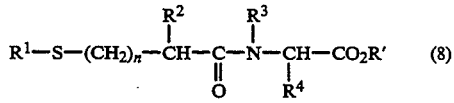
(8)

8. Step of oxidation

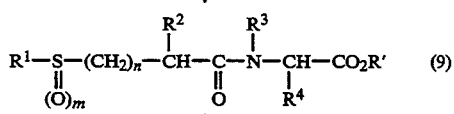
(9)

9. Step of removing a protecting group (II)

To a dialkyl malonate, a halide such as 1-(chloromethyl)naphthalene is reacted at room temperature in a solvent such as tetrahydrofuran in the presence of a base such as sodium hydride to obtain a compound of the formula 2, which is then subjected to a saponification reaction at room temperature in ethanol by means of e.g. potassium hydroxide or sodium hydroxide to obtain a half ester of the formula 3. If this hydrolytic reaction is conducted by means of an enzyme such as esterase or lipase, or an insolubilized enzyme thereof, it is possible to obtain an optically active half ester of the formula 3.

The compound of the formula 3 is condensed with an amino acid having a protected carboxyl group by the above-mentioned usual method for the peptide synthesis, to obtain a compound of the formula 4. As a preferred embodiment, a tert-butyl ester of an amino acid and the compound of the formula 3 are condensed at room temperature in dimethylformamide by means of N,N'-dicyclohexylcarbodiimide in the presence of 1-hydroxybenzotriazole. Depending upon the purpose, the compound of the formula 4 is subjected to an extension of the carbon chain, for example, by the method shown by reaction scheme 2.

Reaction scheme 2

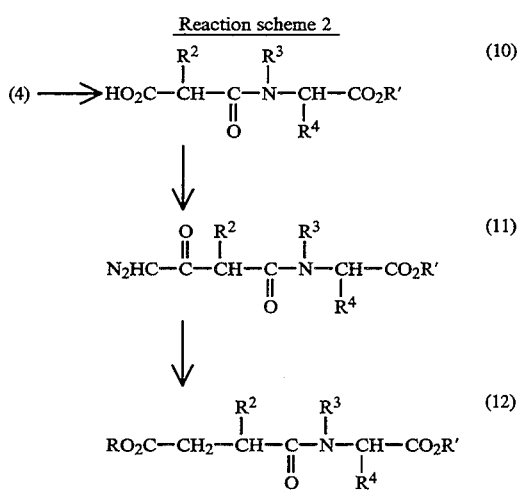

The compound of the formula 4 has two ester moieties. By differenciating the types of the ester moieties, it is possible to convert only one of the ester moieties to a carboxylic acid group. For example, by selecting an ethyl group for R and a tert-butyl group for R', it is possible to hydrolyze only the ethyl ester moiety by saponification with an alkali. The resulting carboxylic acid compound of the formula 10 may be converted to an acid anhydride or to an acid halide by a usual method and then reacted with a diazomethane to obtain a diazoketone compound of the formula 11, which is then reacted with a silver compound such as silver benzoate or silver oxide dissolved in triethyamine, in a lower alkanol such as methanol or ethanol to obtain a compound of the formula 12 having the carbon number increased by one. By repeating this reaction, it is possible to obtain a compound of the formula 5 having various carbon numbers. The compound of the formula 5 has two ester moieties. By differenciating the types of the ester moieties, it is possible to reduce only one of the ester moieties. For example, by using an ethyl group for R and a tert-butyl group for R', it is possible to obtain the desired compound of the formula 6 by the reduction with sodium borohydride in ethanol at room temperature. To facilitate the thioetherification, the hydroxyl group formed by the reduction of the ester of the compound of the formula 5 is converted to an excellent leaving group shown by T such as a tosyloxy group, a mesyloxy group or a halogen. This step can readily be conducted by reacting p-toluenesulfonyl chloride to the compound of the formula 6 at room temperature in the presence of a base such as pyridine. Then, the compound of the formula 7 and a thiol compound are reacted usually at room temperature in the presence of a base such as sodium hydride in a solvent such as dimethylformamide to obtain a compound of the formula 8. The oxidation of the compound of the formula 8 can be conducted by a usual method, for example, with a manganese compound, chromic acid, a lead compound, a halogen, hydrogen peroxide, an organic per acid, an inorganic nitrogen compound or an organic compound such as dimethylsulfoxide. By selecting the oxidizing agent or reaction conditions, a sulfoxide compound (compound wherein m=1) and a sulfone compound (compound wherein m=2) can be prepared, respectively. For example, when a compound of the formula 8 is oxidized at room temperature by means of an aqueous hydrogen peroxide solution in a solvent such as methanol by using sodium tungstate as a catalyst, a sulfonic compound (compound wherein m=2) can be obtained. By removing the protecting group from the compound of the formula 9 by a method suitable for the removal of the particular protecting group, compound of the formula II can be obtained.

Further, the steric chemistry on the carbon to which $R^2$ is bonded, can be freely controlled by utilizing the Sharpless oxidation reaction, for example, by a method represented by Reaction scheme 3.

Reaction scheme 3

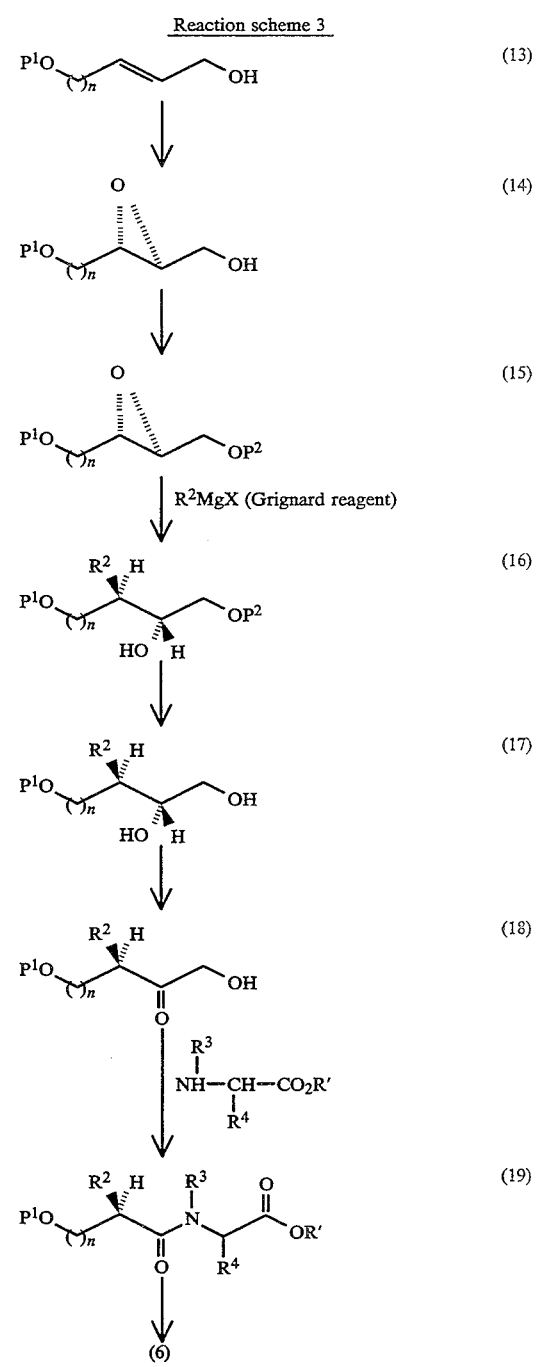

In the above formulas, $R^2$, $R^3$, $R^4$, R', and n are as defined above, and $P^1$ and $P^2$ represent hydroxyl-protecting groups.

An allylic alcohol of the formula 13 is subjected to asymmetric epoxidation in accordance with the method disclosed by A. Pfenninger in "Synthesis" p89–116 (1986). Then, the hydroxyl group is protected by a hydroxyl-protecting group $P^2$ and then the epoxy ring is selectively opened by a Grignard reagent. Then, $P^2$ is removed. Then, oxidation is conducted by e.g. sodium periodate to obtain a carboxylic acid, which is then condensed with an amino acid having a protected carboxylic acid by a usual method for peptide synthesis such as a dicyclohexylcarbodiimide method. Then, the hydroxyl-protecting group $P^1$ is removed to obtain the compound of the formula 6 having the desired steric coordination. The hydroxyl-protecting group $P^1$ is preferably a benzyl group, and $P^2$ is preferably a tert-butyldimethylsilyl group.

Further, the synthesis can be conducted stereoselectivity also by the following Reaction scheme 4.

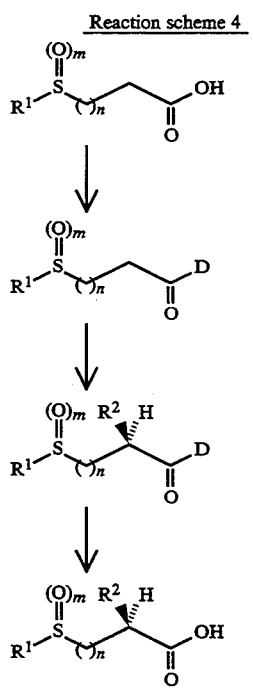

Reaction scheme 4 wherein $R^1$, $R^2$, m and n are as defined above, and D is an optically active amine.

A compound of the formula 20 obtained by reacting a fatty acid having a mercapto group at the terminal with $R^1$—X wherein X is a halogen such as bromine, is converted to a mixed acid anhydride by using e.g. pivaloyl chloride and then condensed with an optically active compound such as (4R,5S)-4-methyl-5-phenyl-2-oxazolidinone in the presence of e.g. n-butyl lithium. Then, $R^2$—X wherein X is a halogen such as bromine is reacted thereto by using a base such as lithium diisopropylamide to stereospecifically introduce the $R^2$ group. Then, if necessary, after an addition of hydrogen peroxide, the product is hydrolyzed with an alkali to obtain a compound of the formula 23. If necessary, by using a suitable oxidizing agent such as hydrogen peroxide, a sulfoxide compound (compound wherein m is 1) or sulfonic compound (compound wherein m is 2) can be obtained. The optically active compound of the formula D may be recovered and again used for the reaction.

Some of the compounds of the formula II can also be prepared by a process shown by Reaction scheme 5.

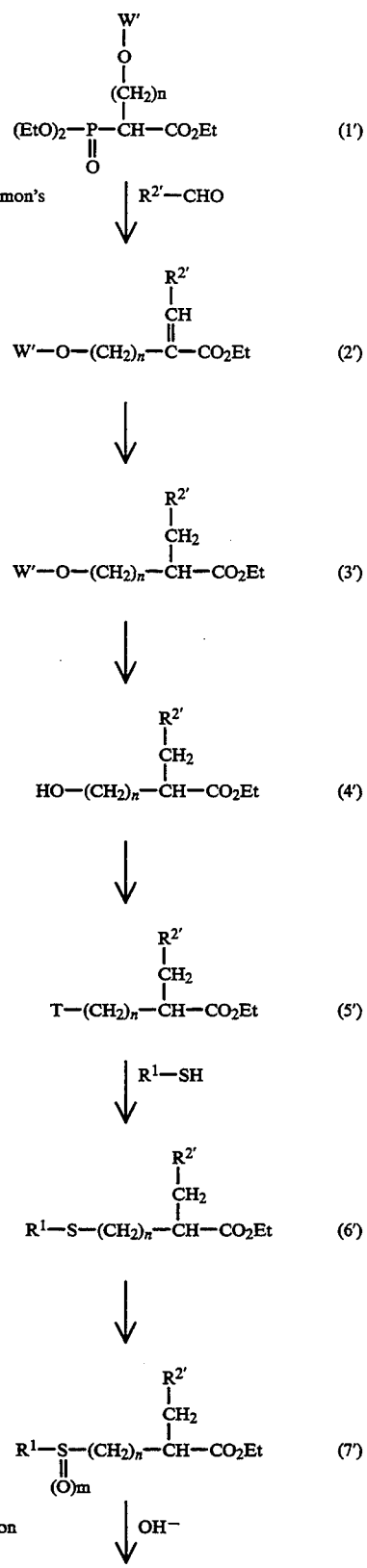

-continued
Reaction scheme 5

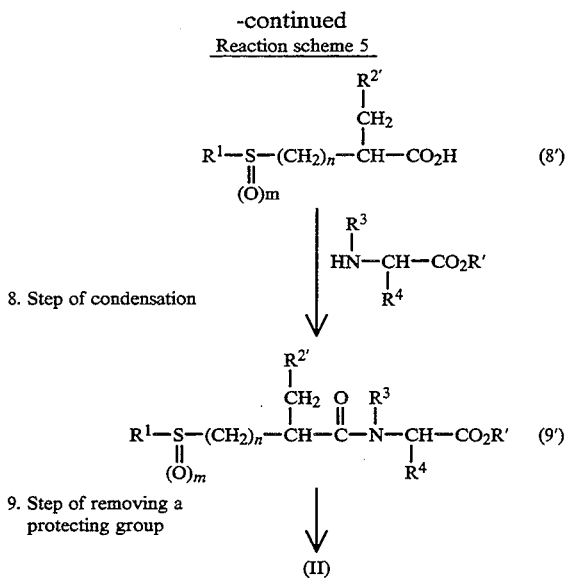

9. Step of removing a
protecting group (II)

In the above formulas, $R^{2'}$ is a substituent of $R^2$ wherein the 1-position is methylene group, such as a naphthylmethyl group. A Horner-Emmon's reagent of the formula 1' and an aldehyde are reacted usually at room temperature preferably under an inert gas stream such as argon or nitrogen in a solvent which does not adversely affect the reaction, such as tetrahydrofuran or dimethylformamide, if necessary, by an addition of an alkali metal or alkaline earth metal halide such as lithium chloride, lithium bromide or magnesium bromide and by a further addition of a base e.g. a tertiary amine such as diazabicycloundecene, triethylamine or diisopropylethylamine or an alkali metal halide, hydroxide, alcoholate or alkyl compound such as sodium hydride, sodium hydroxide, sodium ethoxide or butyl lithium, to obtain a compound Of the formula 2'. The hydroxyl-protecting group W' may be a commonly employed hydroxyl-protecting group such as a tetrahydropyranyl group, a trityl group or a benzyl group, but preferably is a tetrahydropyranyl group. As the Horner-Emmon's reagent, any reagent equivalent to the compound of the formula 1' may be employed. The compound of the formula 2' is catalytically reduced under atmospheric pressure or elevated pressure in the presence of a metal catalyst such as palladium black, palladium-carbon or platinum oxide to obtain a compound of the formula 3', followed by the removal of the protective group to obtain a compound of the formula 4'. Steps 4, 5 and 6 can be conducted in the same manner as Steps 6, 7 and 8, respectively, of Reaction scheme 1. The saponification of Step 7 can be conducted in a usual manner, for example, saponification with an alkali such as sodium hydroxide in a solvent mixture of water and a lower alkanol, to obtain a compound of the formula 8'. The condensation of Step 8 can be conducted in the same manner as Step 3 in Reaction scheme 1. Then, the removal of the protective group is conducted to obtain a compound of the formula II. The compound of the formula III can be prepared by a process shown by Reaction scheme 6 in the case of a compound wherein A is

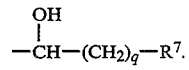

Reaction scheme 6

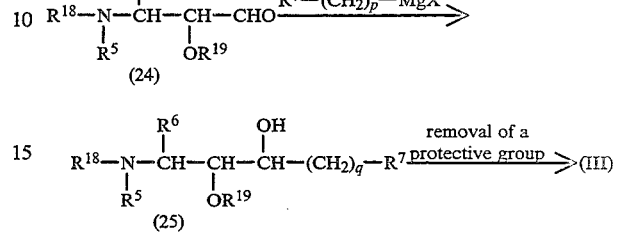

In the above formulas, $R^{18}$ is an amino-protecting group, and $R^{19}$ is a hydroxyl-protecting group. The compound of the formula 24 can be prepared by a method disclosed in Japanese Patent Application No. 173564/1986 by the present inventors, J. Med. Chem., Vol. 30, p.976–982 (1987) or the like. The compound of the formula 24 is reacted with $R^7$—$(CH_2)_q$—MgX wherein X is chlorine or bromine, and $R^7$ is as defined above in a solvent such as dry tetrahydrofuran at a temperature of from $-78°$ C. to room temperature, to obtain a compound of the formula 25. By removing the protective group, a compound of the formula III can be obtained.

Some of the compounds can also be prepared by a process shown by Reaction scheme 7.

Reaction scheme 7

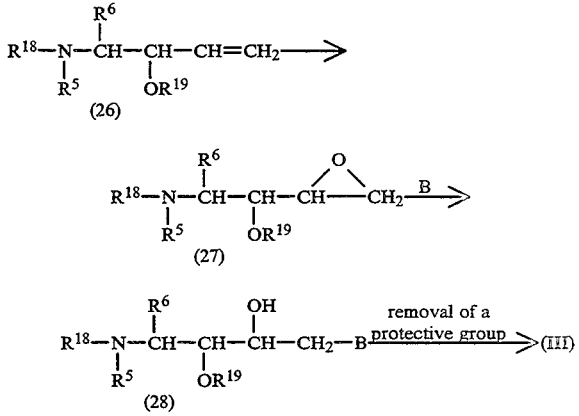

The compound of the formula 26 is a starting material for the preparation of the compound of the formula 24, the method for the preparation thereof is also disclosed in J. Med. Chem., Vol. 30, p.976–982 (1987). The compound of the formula 26 is reacted with an oxidizing agent such as m-chloro perbenzoic acid at room temperature in a solvent such as methylene chloride to obtain a compound of the formula 27, which is then reacted with a nucleophilic reagent B such as a thiol compound to obtain a compound of the formula 28. By the removal of a protecting group, a compound of the formula III can be obtained.

Some of the compounds of the formula III can be prepared stereospecifically by utilizing the asymmetric center of a saccharide by a process as shown by Reaction scheme 8.

Reaction scheme 8

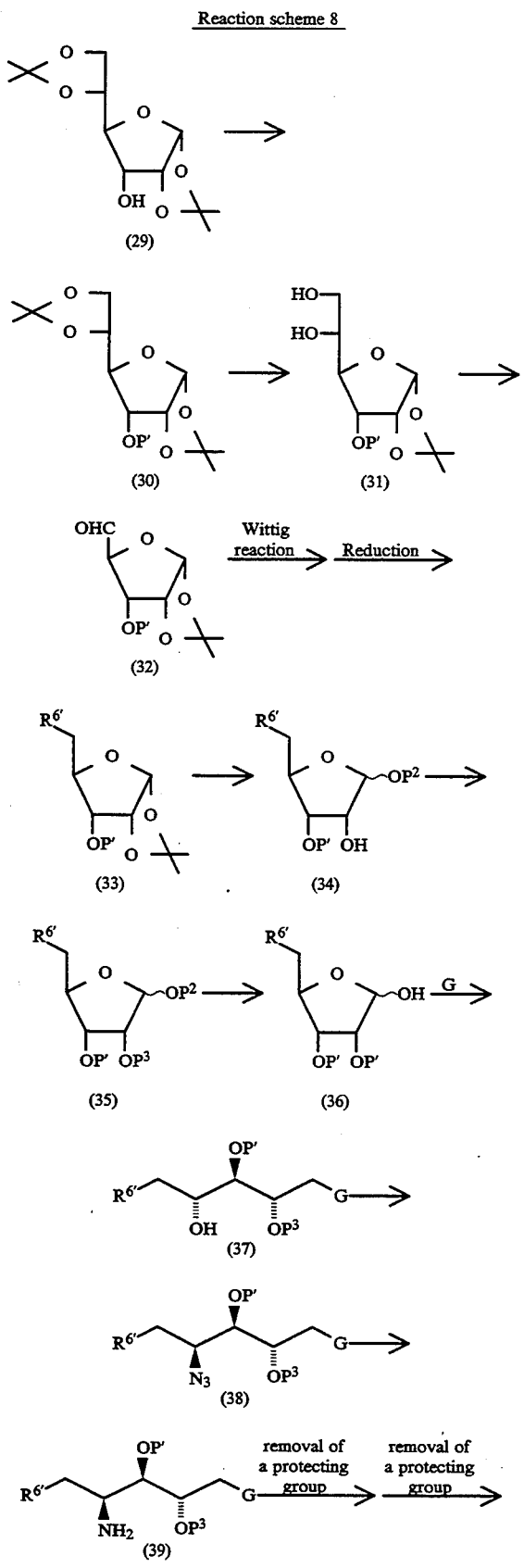

-continued
Reaction scheme 8

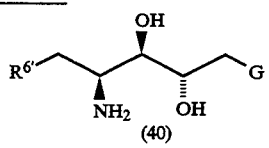

In the above formulas, $R^{6'}$ corresponds to $R^6$ except that it is shorter than $R^6$ by one methylene, and $P^1$, $P^2$ and $P^3$ are hydroxyl-protecting groups, and G represents an amine compound.

The starting material 1,2:5,6-diisopropylidene-α-D-allofuranose can readily be prepared from a D-glucose by a method disclosed by J. D. Stevens in "Methods in Carbohydrate Chemistry", Vol VI p.123 (1972) After protecting the hydroxyl group at the 3-position by $P^1$, only the 5,6-isopropylidene was selectively removed by means of e.g. acetic acid. Then, by means of a suitable oxidizing agent such as sodium periodate, the product is converted to an aldehyde. Then, a desired side chain is introduced by Witting reaction. If necessary, the olefin is reduced by means of e.g. Raney nickel. The 1,2-isopropylidene is removed by treatment with an acid in a lower alcohol, and at the same time, the hydroxyl group at the 1-position is protected by $P^2$. Further, the hydroxyl group at the 2-position is protected by $P^3$, and then the hydroxyl-protecting group $P^2$ at the 1-position is removed. An amine compound G such as morpholine is added, and the amino alkylation reaction is conducted by means of a metal hydride complex compound such as sodium cyano borohydride. Then, the free hydroxyl group at the 4-position is stereoinversibly converted to an azide group by means of diphenylphospholyl azide in the presence of suitable azide-forming agents, preferably triphenylphosphine and diethyl azodicarboxylate. This azide group is reduced to an amino group in a usual manner. Then, the hydroxyl-protecting groups $P^1$ and $P^3$ are removed. Thus, some of the compounds of the formula III can be stereospecifically prepared. A benzyl group may be mentioned as a preferred example for the hydroxyl-protecting group $P^1$ or $P^3$, and a methyl group may be mentioned as a preferred example for the hydroxyl-protecting group $P^2$.

Further, as shown by a typical example in Reaction scheme 9, such a stereospecific synthesis can be conducted by the above Sharpless asymmetric epoxidation reaction by using an optically inactive compound as the starting material.

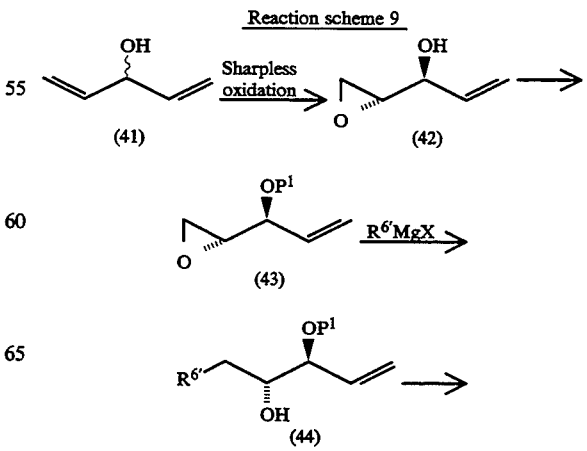

-continued
Reaction scheme 9

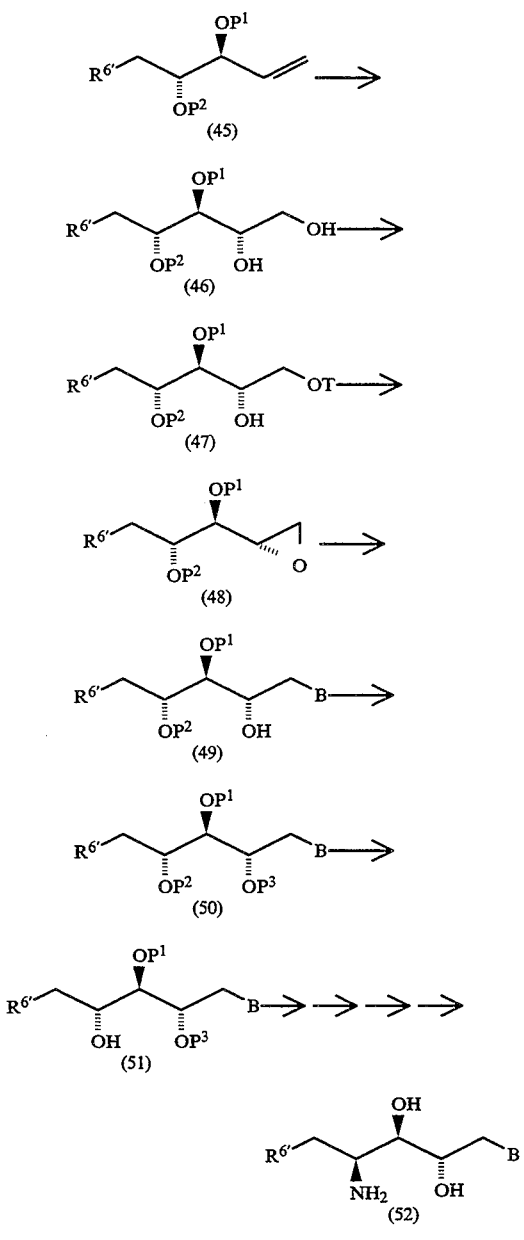

In the above formulas, $R^{6'}$, T, B, $P^1$, $P^2$ and $P^3$ are as defined above.

1,4-Pentadien-3-ol of the formula 41 prepared from vinyl magnesium bromide and methyl formate, is subjected to the above-mentioned Sharpless asymmetric epoxidation reaction to obtain an epoxy compound of the formula 42. After protecting the hydroxyl group by $P^1$, the epoxy ring is selectively opened by means of a Grignard reagent $R^{6'}MgX$, and the side chain is introduced. After protecting the formed hydroxyl group by $P^2$, a hydroxyl group is stereoselectively introduced by an oxidizing agent such as osmium tetraoxide to obtain a compound of the formula 46. A leaving group such as a tosyl group or a mesyl group is bonded to the primary hydroxyl group, followed by treatment with an alkali such as potassium carbonate, whereby an epoxy compound of the formula 48 can be stereospecifically obtained. This compound of the formula 48 can also be prepared by removing the hydroxyl-protecting group $P^1$ of the compound of the formula 45, followed by the above sharpless asymmetric epoxidation reaction and against protecting the hydroxyl group by $P^1$. A nucleophilic reagent B such as a thiol compound or an amine compound is reacted to the compound of the formula 48, and the formed hydroxyl group is protected by $P^3$, and the hydroxyl-protecting group $P^2$ is removed to obtain a compound of the formula 51. A compound of the formula III can be stereospecifically prepared from the compound of the formula 51 in the same manner as shown by the process steps 37→38→39→40 as shown in Reaction scheme 8.

Further, the compound of the formula III wherein A is $$-CH_2-\underset{\underset{R^5}{|}}{CH}-\underset{\underset{O}{\|}}{C}-R^3$$

can be prepared by the process shown by Reaction scheme 10.

Reaction scheme 10

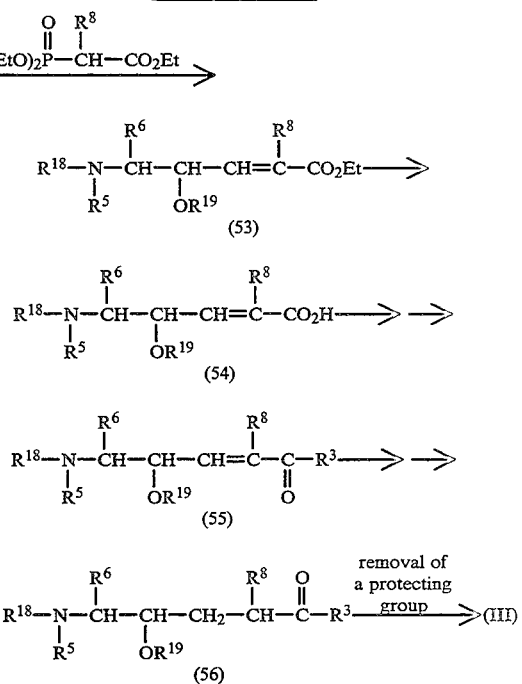

The compound of the formula 24 is reacted with the Horner-Emmon's reagent

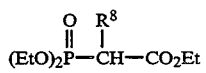

preferably in an inert gas stream such as argon or nitrogen in a solvent which does not adversely affect the reaction, such as tetrahydrofuran or dimethylformamide, if necessary by an addition of an alkali metal or alkaline earth metal halide such as lithium chloride, lithium bromide or magnesium bromide and further by an addition of a base, for example, a tertiary amine such as diazabicycloundecene, triethylamine or diisopropylethylamine or an alkali metal hydride, hydroxide, alcoholate or alkyl compound such as sodium hydride, sodium hydroxide, sodium ethoxide or butyl lithium, usually at room temperature, to obtain a compound of the formula 53. The Horner-Emmon's reagent may be any reagent so long as it is equivalent to

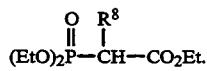

The ester of the compound of the formula 53 is hydrolyzed at room temperature with sodium hydroxide or potassium hydroxide in e.g. a solvent mixture of a lower alkanol and water to obtain a carboxylic acid of the formula 54. Then, this carboxylic acid is converted to a reactive derivative such as a halide, an acid anhydride, am active ester or an azide by a usual method and then reacted with an amide compound or an alcohol compound to obtain a compound of the formula 55. In this condensation step, any one of the above peptide syntheses can be employed. In a preferred embodiment, the compound of the formula 54 is dissolved in an anhydrous solvent such as dimethylformamide, and triethylamine, diphenylphospholyl azide and an alkylamine were added at a low temperature at a level of $-20°$ C. to conduct a reaction at room temperature to obtain a compound of the formula 55. The compound of the formula 55 is catalytically reduced in the presence of e.g. palladium black, palladium-carbon or platinum oxide under atmospheric pressure or elevated pressure to obtain a compound of the formula 56. Then, the protecting group is removed to obtain a compound of the formula III. Depending upon the type of the protecting group, the step of this catalytic reduction and the step of removal of the protecting group can be conducted simultaneously.

The compound of the formula IV can be prepared in the same manner as in Reaction scheme 1 except that the condensation step 3 is omitted. Namely, the compound of the formula 3 is converted to

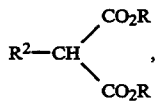

and the subsequent steps are the same as the steps 4→5→6→7→8→9 to obtain a compound of the formula IV.

The compound of the formula V can readily be obtained by condensing an amino-protecting amino acid and the compound of the formula III in accordance with a usual method for the peptide synthesis, followed by removal of the protecting group.

When the compound of the present invention is to be used as a medicine, it may be administered by itself, but it is usually administered as a mixture with a carrier suitably selected depending upon the route for administration and standard formulations. For example, for oral administration, the compound of the present invention may be administered in the form of tablets which may be prepared by adding to a powder of the active ingredient of the present invention an excipient such as starch, lactose, sucrose, glucose, crystalline cellulose, calcium carbonate or kaolin, a binder such as a starch solution, a gelatin solution a hydroxypropylcellulose, a glucose solution, a sucrose solution, water or ethanol, a disintegrator such as starch, agar, gelatin powder, carboxymethylcellulose calcium (CMC-Ca), carboxymethylcellulose sodium (CMC-Na), crystalline cellulose, calcium carbonate or sodium hydrogencarbonate, or a lubricant such as magnesium stearate, calcium stearate, talc, macrogoal 4,000, macrogoal 6,000 or stearic acid, subjecting the mixture to compression molding by a conventional tabletting method, and if necessary, applying a sugar coating by means of a concentrated sugar solution containing e.g. gum arabic, talc, polyvinylpyrolidone, polyethyleneglycol and/or titanium oxide, applying a film coating by means of a film-forming agent composed of e.g. polyvinyl acetal diethylaminoacetate, hydroxypropylmethylcellulose, hydroxypropylcellulose, ethylcellulose or polyvinylpyrrolidone, or applying an enteric coating by means of a film-forming agent composed of e.g. ethylcellulose phthalate cerac, cellulose acetate phthalate or hydroxypropylmethylcellulose phthalate; granules or fine granules which may be prepared by adding to the active ingredient of the present invention a binder such as starch, gelatin, gum arabic, methylcellulose, sodium carboxymethylcellulose, heavy silicic anhydride or light silicic anhydride, followed by kneading and granulation by usual methods; a powder of the active ingredient of the present invention by itself; or capsules which may be prepared by adding to the active ingredient of the present invention an excipient such as lactose, starch or crystalline cellulose and/or a lubricant such as magnesium stearate, calcium stearate or talc, and filling the mixture into capsules. For non-oral administration, an injection formulation may be used wherein an emulsifying agent such as propyleneglycol, polyethyleneglycol or a vegetable oil such as olive oil, or a solubilization agent such as sodium benzoate, sodium salicylate, N-hydrooxyethyllactamide, calcium α-saccharide, mannitol, nicotic acid amide or cyclodextrin, is suitably used.

Further, to such formulations, other medicinal substances may be incorporated. Such medicinal substances include, for example, acetazolamide, amiloride, chlorothiazide, furosemide, timolol, propranolol, cetamolol, clonidine, methyldopa, minoxydil, hydralazine, captopril, pivalopril, enalapril, lidinopril, verapamil, nifedipine, nicardipine, felodipine, nimodipine and diltiazem.

An advantageous formulation contains from about 0.1 mg to 500 mg of the compound of the present invention. A preferred range of a daily dose for oral administration is from about 0.1 mg/kg to 500 mg/kg, and such a daily dose may be administered at once or in three times a day. For non-oral administration, it is preferred to administer the compound of the present invention in an amount of from about 0.1 mg/kg to 10 mg/kg per day at once. The dose may be increased or reduced by a doctor's prescription depending upon e.g. the sex and diseased condition of the patient.

Now, the present invention will be described in further detail with reference to Test Examples for renin inhibiting activities of the compounds of the present invention and Working Examples.

TEST EXAMPLE 1

Renin inhibiting activities

To 156 μl of a 0.2M sodium phosphate buffer solution (pH7.4), 40 μl of a solution mixture of 34 mM 8-hydroxyquinoline and 100 mM disodium ethylenediamine tetraacetate, 4 μl of dimethyl sulfoxide or a dimethyl sulfoxide solution of test compound and 200 μl of human plasma were added and reacted at 37° C. for one hour.

Then, pepstatin was added thereto to terminate the reaction, and the amount of the resulting angiotension I was measured by radio immunoassay whereby the inhibiting activity was determined. The 50 % inhibition concentrations ($IC_{50}$ values) of the compounds of the present invention are shown below.

TABLE 1

| Test Compounds | $IC_{50}$ (M) |
|---|---|
| Compound of Example 1 | $2.5 \times 10^{-9}$ |
| Compound of Example 2 | $7.2 \times 10^{-9}$ |
| Compound of Example 3 | $3.1 \times 10^{-9}$ |
| Compound of Example 4 | $7.7 \times 10^{-9}$ |
| Compound of Example 5 | $5.0 \times 10^{-9}$ |
| Compound of Example 6 (having a high Rf value) | $6.0 \times 10^{-9}$ |
| Compound of Example 6 (having a low Rf value) | $4.1 \times 10^{-9}$ |
| Compound of Example 7 | $2.8 \times 10^{-9}$ |
| Compound of Example 8 | $3.3 \times 10^{-9}$ |
| Compound of Example 11 | $6.3 \times 10^{-9}$ |
| Compound of Example 12 | $4.3 \times 10^{-9}$ |
| Compound of Example 13 | $2.0 \times 10^{-9}$ |
| Compound of Example 14 | $2.0 \times 10^{-9}$ |
| Compound of Example 15 | $7.3 \times 10^{-9}$ |
| Compound of Example 16 | $6.0 \times 10^{-9}$ |
| Compound of Example 17 | $8.3 \times 10^{-9}$ |
| Compound of Example 18 | $9.2 \times 10^{-9}$ |
| Compound of Example 20 (having a low Rf value) | $4.0 \times 10^{-9}$ |
| Compound of Example 23 | $4.8 \times 10^{-9}$ |
| Compound of Example 27 | $2.2 \times 10^{-9}$ |
| Compound of Example 28 | $1.9 \times 10^{-9}$ |
| Compound of Example 29 | $7.6 \times 10^{-10}$ |
| Compound of Example 30 | $1.9 \times 10^{-9}$ |
| Compound of Example 33 (having a high Rf value) | $2.2 \times 10^{-9}$ |
| Compound of Example 33 (having a low Rf value) | $1.1 \times 10^{-9}$ |
| Compound of Example 34 | $5.6 \times 10^{-9}$ |
| Compound of Example 35 | $3.1 \times 10^{-9}$ |
| Compound of Example 36 | $1.9 \times 10^{-9}$ |
| Compound of Example 37 | $2.9 \times 10^{-9}$ |
| Compound of Example 39 | $1.3 \times 10^{-9}$ |
| Compound of Example 40 | $1.0 \times 10^{-9}$ |
| Compound of Example 41 | $7.9 \times 10^{-10}$ |
| Compound of Example 42 | $6.1 \times 10^{-9}$ |
| Compound of Example 43 | $2.4 \times 10^{-9}$ |
| Compound of Example 44 | $1.8 \times 10^{-9}$ |
| Compound of Example 48 | $3.9 \times 10^{-9}$ |

From the above results, it is evident that the compounds of the present invention have remarkably strong inhibiting activities against human plasma renin.

TEST EXAMPLE 2

Hypotensive activities in monkeys

The hypotensive activities were measured in accordance with a method disclosed in J. Cardiovascular Pharmacology, Vol. 7, (Suppl. 4) S58–61 (1985). Namely, 30 mg/kg of furosemide (diuretic) was intracutaneously injected to three marmosets i.e. small size monkeys to produce a high renin active state. To these marmosets, 30 mg/kg of the compound of Example 1 was orally administered, whereupon the hypotensive activities were measured. The results are shown in FIG. 1.

It is evident from FIG. 1 that the compound of the present invention exhibits hypotensive activities by the oral administration. Thus, the compound of the present invention has properties useful as a medicine.

Now, the present invention will be described in further detail with reference to Examples. However, it should be understood that the present invention is by no means restricted to such specific Examples.

EXAMPLE 1

(2S, 3R, 4S)-4-{L-N-[(2S)-3-[(2RS)-2,3-diacetoxypropyl]sulfonyl-2-(1-naphthylmethyl) propionyl]norleucyl}amino-5-cyclohexyl-1-morpholino-2,3-pentanediol (1) (E)-4-benzyloxy-2-buten-1-ol (a) 14.6 g of sodium hydride (60 % in oil) was washed with n-pentane under an argon gas. After drying, 150 ml of dry dimethylformamide (hereinafter referred to simply as DMF) was added thereto to form a suspension. 75 g of (Z)-2-buten-1,4-diol was dropwise added thereto at 0° C. under stirring over a period of 30 minutes. The mixture was stirred at room temperature for 1.5 hours, and 44 g of benzyl bromide was added at 0° C. under stirring. The mixture was stirred at the same temperature for 30 minutes, and then the temperature was returned to room temperature. The mixture was stirred at 50° C. overnight. The reaction solution was poured into ice water and extracted with diethyl ether. The ether solution was washed sequentially with water and with a saturated sodium chloride aqueous solution and then dried over anhydrous magnesium sulfate. The solvent was distilled off under reduced pressure, and the residue was subjected to distillation under reduced pressure (2.5 mmHg, 134°–138° C.) to obtain 29 g of (Z)-4-benzyloxy-2-buten-1-ol as colorless oily substance.

Rf value: 0.49 (n-hexane/ethyl acetate=1/1)

(b) 11.1 g of pyridinium chlorochromate and 12 g of Celite were suspended in 100 ml of dry dichloromethane, and 6 g of (Z)-4-benzyloxy-2-buten-1-ol was added thereto at 0° C. under stirring. The mixture was stirred at room temperature for 3 hours. Diethyl ether was added thereto, and insolubles were removed by filtration. The filtrate was distilled under reduced pressure to remove the solvent, and the residue was purified by silica gel column chromatography (diethyl ether) to obtain 3.9 g of (Z)-4-benzyloxy-2-butenal as slightly yellow oily substance.

Rf value: 0.59 (n-hexane/ethyl acetate=1/1)

(c) 3.9 g of (Z)-4-benzyloxy-2-butenal was dissolved in 60 ml of ethanol, and 850 mg of sodium borohydride was added thereto at 0° C. under stirring. The mixture was stirred at 0° C. for 1.5 hours. The reaction solution was poured into ice water and extracted with ethyl acetate. The ethyl acetate solution was washed sequentially with water and with a saturated sodium chloride aqueous solution and dried over anhydrous sodium sulfate. Then, the solvent was distilled off under reduced pressure, and the residue was subjected to distillation under reduced pressure (2.0 mmHg, 142° C.) to obtain 2.2 g of (E)-4-benzyloxy-2-buten-1-ol as colorless oily substance.

Rf value: 0.49 (n-hexane/ethyl acetate=1/1)

(2) (2R,3R)-4-benzyloxy-1-tert-butyldimethysilyloxy-3 (1-naphthylmethyl)-2-butanol (a) 3.3 g of molecular sieve (powder, 3A) was suspended in 190 ml of dry dichloromethane, and 4.2 ml of isopropyl orthotitanate and 2.9 ml of diethyl L(+)-tartrate were added thereto at −23° C. under stirring. The mixture was stirred at the same temperature for 15 minutes. Then, 3 ml of a dry dichloromethane solution of 4.7 g of (E)-4-benzyloxy-2-buten-1-ol was added thereto, and the mixture was stirred at the same temperature for 5 minutes. 11 ml of tert-butylhydroperoxide (a 5.17M dichloromethane solution) was added thereto, and the mixture was stirred for further 7 hours. Then, the reaction mixture was left to stand at −23° C. overnight. 190 ml of diethyl ether and 4.2 ml of a saturated sodium sulfate aqueous solution were added to the reaction solution, and the mixture was stirred at room temperature for 4 hours. Insolubles were removed by filtration, and then the solvent was distilled off under reduced pressure. The residue was dissolved in 240 ml of diethyl ether. 42 ml of a 1N sodium hydroxide aqueous solution was added thereto at 0° C. under stirring, and the mixture was stirred at 0° C. for 30 minutes. The ether layer was washed sequentially with a saturated sodium hydrogencarbonate aqueous solution and with a saturated sodium chloride aqueous solution and then dried over anhydrous sodium sulfate. The solvent was distilled off under reduced pressure, and then the residue was purified by silica gel column chromatography (n-hexane/ethyl acetate=1/1) to obtain 2.9 g of (2S, 3S)-4-benzyloxy-2,3-epoxy-1-butanol as colorless oily substance.

Rf value: 0.28 (n-hexane/ethyl acetate=1/1) Angle of rotation: $[\alpha]_D^{20}=-22.7°$ (C 0.988, CHCl$_3$) Mass spectrum (FAB) m/z 195(M+1)+

(b) 2.15 g of the compound obtained in Example 1(2a) was dissolved in 13 ml of dry DMF, and 1.83 g of imidazole and 2 g of tert-butyldimethylchlorosilane were added thereto. The mixture was stirred at room temperature overnight. The reaction solution was diluted with ethyl acetate and washed sequentially with cold 1N hydrochloric acid, with water and with a-saturated sodium chloride aqueous solution. The reaction solution was dried over anhydrous sodium sulfate, and then the solvent was distilled off under reduced pressure. The residue was purified by silica gel column chromatography (n-hexane/ethyl acetate =10/1) to obtain 2.3 g of (2S,3S)-4-benzyloxy-2,3-epoxy-1-butanol tert-butyldimethylsilyl ether as colorless oily substance.

Rf value: 0.59 (n-hexane/ethyl acetate=5/1) Angle of rotation: $[\alpha]_D^{20}-9.0°$ (C 1.140, CHCl$_3$) Mass spectrum (FAB) m/z 441(M+Cs)+

(c) 123 mg of copper iodide was suspended in 2.3 ml of dry tetrahydrofuran (hereinafter referred to simply as THF), and 8 ml of naphthylmethyl magnesium chloride (a 0.8M diethyl ether solution) was added thereto under stirring. The mixture was stirred at the same temperature for 5 minutes. Then, 1.0 ml of a dry THF solution of 1 g of the compound obtained in Example 1(2b) was added thereto, and the mixture was stirred at room temperature for 1 hour. The reaction solution was poured into a saturated ammonium chloride aqueous solution, extracted with diethyl ether and washed sequentially with water and with a saturated sodium chloride aqueous solution. The ether layer was dried over anhydrous sodium sulfate, and then the solvent was distilled off under reduced pressure. The residue was purified by silica gel column chromatography (n-hexane/ethyl acetate=20/1) to obtain 938 mg of the above-identified compound as colorless oily substance.

Rf value: 0.53 (n-hexane/ethyl acetate=5/1) Angle of rotation: $[\alpha]_D^{20}=-21.8°$ (C 1.120, CHCl$_3$) Mass spectrum (FAB) m/z 451(M+1)+

(3) (2R,3R )-4-benzyloxy-3-(-naphthylmethyl)-butane-1,2-diol 910 mg of the compound obtained in Example 1(2c) was treated with 7 ml of tetra-n-butylammonium fluoride (a 1N THF solution), and stirred at 0° C. for 10 minutes and then at room temperature for 50 minutes. The reaction solution was diluted with diethyl ether, then washed sequentially with a saturated sodium hydrogencarbonate aqueous solution and with a saturated sodium chloride aqueous solution and dried over anhydrous sodium sulfate. The solvent was distilled off under reduced pressure, and the residue was purified by silica gel column chromatography (n-hexane/ethyl acetate=1/1) to obtain 642 mg of the above-identified compound as colorless oily substance.

Rf value: 0.29 (n-hexane/ethyl acetate=1/1) Angle of rotation: $[\alpha]_D^{20}=-42.6°$ (C 1.187, CHCl$_3$) Mass spectrum m/z 337(M+1)+

(4) (2R)-3-benzyloxy-2-(1-naphthylmethyl)propionic acid 740 mg of the compound obtained in Example 1(3) was dissolved in 50 ml of methanol, and 19 ml of an aqueous solution of 568 mg of sodium metaperiodate was added thereto under cooling with ice and stirring. The mixture was stirred at room temperature for 4 hours. Insolubles were removed by filtration, and then the solvent was concentrated under reduced pressure. The concentrate was diluted with a saturated sodium hydrogencarbonate aqueous solution, extracted with diethyl ether, then washed with a saturated sodium chloride aqueous solution and dried over anhydrous sodium sulfate. The solvent was distilled off under reduced pressure. 620 mg of (2R)-3-benzyloxy-2-(1-naphthylmethyl)-1-propanal thereby obtained as oily substance was dissolved in 50 ml of acetone, and John's reagent was added at 0° C. under stirring. The mixture was stirred at the same temperature for 1.5 hours. Isopropanol was added to the reaction solution to decompose the reagent. Then, insolubles were removed by filtration, and the filtrate was concentrated under reduced pressure. The concentrate was diluted with ethyl acetate, washed sequentially with water and with a saturated sodium chloride aqueous solution and dried over anhydrous sodium sulfate. Then, the solvent was distilled off under reduced pressure, and the residue was purified by silica gel column chromatography (n-hexane/ethyl acetate=2/1) to obtain 457 mg of the above-identified compound as colorless oily substance.

Rf value: 0.47 (n-hexane/ethyl acetate/acetic acid=1/1/0.5) Angle of rotation: $[\alpha]_D^{20}=-13.2°$ (C 1.04, CHCl$_3$) Mass spectrum m/z 321(M+1)+ NMR (300 MHz, CDCl$_3$) δ ppm : 3.11~3.21(1H,m),3.33(1H,dd,J=15.2,8.0 Hz),3.57(1H,dd,J=15.2, 7.6 Hz),3.66(2H,d,J=7.2 Hz),4.51(1H,d,J=16.0 Hz),4.55(1H,d,J=16.0 Hz ), 7.24~7.38(7H, m ),7.45~7.55(2H,m), 7.75(1H,d,J=8.0 Hz),7.86(1H,d, J=8.0 Hz),8.05(1H,d,J=8.0 Hz)

(5) (2R)-3-hydroxy-2-(1-naphthylmethyl)propionic acid 394 mg of the compound obtained in Example 1(4) was dissolved in 6 ml of THF, and 3 ml of cyclohexene, 2.5 ml of 1N hydrochloric acid and 400 mg of 10% palladium-carbon were added thereto. The mixture was refluxed under heating for 48 hours. After the filtration, the solvent was distilled off under reduced pressure, and the residue was partitioned between ethyl acetate and a 4% sodium hydrogencarbonate aqueous solution. The aqueous layer was adjusted to pH2 with 1N hydrochloric acid under cooling with ice and extracted with ethyl acetate. The ethyl acetate layer was washed sequentially with water and with a saturated sodium chloride aqueous solution and then dried over anhydrous sodium sulfate to obtain 212 mg of (2R)-3-hydroxy-2-(1-naphthylmethyl)propionic acid as colorless oily substance.

Rf value: 0.40 (n-hexane/ethyl acetate/acetic acid=6/6/0.2)

(6) L-N-[(2R)-3-hydroxy-2-(1-naphthylmethyl) propionyl]norleucine tert-butyl ester 79 mg of the compound obtained in Example 1(5) was dissolved in 0.5 ml of DMF, and 1.0 ml of a DMF solution of 84 mg of L-norleucine tert-butyl ester, 82 mg of 1-hydroxybenzotriazole monohydrate and 79 mg of N,N'-dicyclohexylcarbodiimide (hereinafter referred to simply as DCC) were added thereto at −15° C. under stirring. The mixture was stirred at −15° C. for 1 hour and then at room temperature overnight. Then, dicyclohexyl urea was removed by filtration. The filtrate was diluted with ethyl acetate, washed sequentially with a 4% sodium hydrogencarbonate aqueous solution and with a saturated sodium chloride aqueous solution and dried over anhydrous magnesium sulfate. Inorganic salts were removed by filtration, and then the filtrate was concentrated under reduced pressure. The residue was purified by silica gel column chromatography (n-hexane/ethyl acetate=2/1) to obtain 79 mg of L-N-[(2R)-3-hydroxy-2-(1-naphthylmethyl)propionyl]norleucine tert-butyl ester as white solid.

Rf value: 0.26 (n-hexane/ethyl acetate=2/1)

(7) L-N-[(2S)-3-[(2RS)-2,3-diacetoxypropyl]thio-2-(1-naphthylmethyl)propionyl]norleucine tert-butyl ester dissolved in 0.8 ml of dry pyridine, and 80 mg of p-toluenesulfonyl chloride was added thereto. The mixture was stirred at room temperature overnight. The reaction solution was poured into ice water and extracted with ethyl acetate. The ethyl acetate layer was washed sequentially with 1N hydrochloric acid, with water, with a saturated sodium hydrogencarbonate aqueous solution and with a saturated sodium chloride aqueous solution and dried over anhydrous sodium sulfate. Then, the solvent was distilled off under reduced pressure, and the residue was purified by silica gel column chromatography (n-hexane/ethyl acetate=3/1) to obtain 86 mg of L-N-[(2R)-2-(1-naphthylmethyl)-3-p-toluenesulfonyloxypropionyl]norleucine tert-butyl ester as colorless oily substance.

Rf value: 0.54 (n-hexane/ethyl acetate=2/1)

(b) 37.7 mg of potassium tert-butoxide was suspended in 0.3 ml of dry DMF, and 40 μl of a-thioglycerol was added thereto under cooling with ice and stirring. The mixture was stirred at room temperature for 30 minutes. Then, 0.7 ml of a dry DMF solution of 84 mg of the compound obtained in Example 1(7a) was added thereto under cooling with ice, and the mixture was stirred at room temperature for 2 hours. To the reaction solution, ethyl acetate was added, and washed sequentially with water and with a saturated sodium chloride aqueous solution. The ethyl acetate layer was dried over anhydrous sodium sulfate. The solvent was distilled off under reduced pressure, and then the residue was purified by silica gel column chromatography (n-hexane/ethyl acetate=1/3) to obtain 57.3 mg of L-N-[(2S)-3-[(2RS)-2,3-dihydroxypropyl]thio-2-(1-naphthylmethyl)propionyl]norleucine tert-butyl ester as colorless oily substance.

Rf value: 0.52 (n-hexane/ethyl acetate=1/3)

(c) 57.3 mg of the compounds obtained in Example 1(7 b) was dissolved in 0.4 ml of dry pyridine, and 0.2 ml of acetic anhydride was added thereto. The mixture was stirred at room temperature for 5 hours. A small amount of water was added to the reaction solution, and the mixture was diluted with ethyl acetate and washed sequentially with 1N hydrochloric acid, with water, with a saturated sodium hydrogencarbonate aqueous solution and with a saturated sodium chloride aqueous solution. The organic layer was dried over anhydrous sodium sulfate. Then, the solvent was distilled off under reduced pressure to obtain 64 mg of the above-identified compound as colorless oily substance.

Rf value: 0.24 (n-hexane/ethyl acetate=3/1)

(8) L-N-[(2S)-3-[(2RS)-2,3-diacetoxypropyl]sulfonyl-2-(naphthylmethyl)propionyl]norleucine (a) 63 mg of the compound obtained in Example 1(7c) was dissolved in 1.0 ml of methanol, and 0.19 ml of 30% aqueous hydrogen peroxide and 7.2 mg of sodium tungstate dihydrate were added thereto. The mixture was stirred at room temperature for 2 hours. To the reaction solution, ethyl acetate was added, and washed sequentially with water and with a saturated sodium chloride aqueous solution. The organic layer was dried over anhydrous sodium sulfate. Then, the solvent was distilled off under reduced pressure, and the residue was purified by silica gel column chromatography (n-hexane/ethyl acetate =2/1) to obtain 53 mg of L-N-[(2S)-3-[(2RS)-2,3-diacetoxypropyl]sulfonyl-2-(1-naphthylmethyl)propionyl]norleucine tert-butyl ester as colorless oily substance.

Rf value: 0.46 (n-hexane/ethyl acetate=1/1)

(b) 51.5 mg of the compound obtained in Example 1(8a) was dissolved in 0.3 ml of dichloromethane, and 0.3 ml of trifluoroacetic acid (hereinafter referred to simply as TFA) was added thereto. The mixture was stirred at room temperature for 1 hour. To the reaction solution, ethyl acetate was added, washed sequentially with water and with a saturated sodium chloride aqueous solution and dried over anhydrous sodium sulfate. Then, the solvent was distilled off under reduced pressure to obtain 45 mg of the above-identified compound as colorless oily substance.

(9) (2S,3R,4S)-4-{(L-N,[(2S)-3-[(2RS)-2,3-diacetoxypropyl]sulfonyl-2-(1-naphthylmethyl)propionyl]norleucyl}amino-5-cyclohexyl-1-morpholino-2,3-pentanediol 45 mg of the compound obtained in Example 1(8b) was dissolved in 0.3 μl of dry DMF, and 14 μl of triethylamine, 21 μl of diphenylphosphoryl azide (hereinafter referred to simply as DPPA), 0.6 ml of a dry DMF solution of 40 mg of (2S,3R,4S)-4-amino-5-cyclohexyl-1-morpholino-2,3-pentanediol dihydrochloride and 28 μl of triethyl amine were added thereto at −15° C. under stirring. The mixture was stirred at room temperature overnight, and then 30 ml of ethyl acetate was added to the reaction solution. The mixture was washed sequentially with 1N hydrochloric acid, with water, with a 4% sodium hydrogencarbonate aqueous solution, with water and with a saturated sodium chloride aqueous solution and then dried over anhydrous sodium sulfate. The solvent was distilled off under reduced pressure, and the residue was purified by silica gel column chromatography (chloroform/methanol=50/1) to obtain 41.1 mg of the above-identified compound as white powder.

Rf value: 0.56 (chloroform/methanol=10/1)

Mass spectrum (FAB) m/z 818(M+1)+ NMR (300 MHz, CDCl$_3$) δ ppm : 0.80∼0.95(3H,m), 1.10∼1.82(19H,m), 1.97(1.5H,s),2.07(4.5H,s),2.40∼2.82(6H,m),2.99∼3.86(-14H,m),3.97∼4.07(1H,m),4.18∼4.32(3H,m),4.60(1H,b-s),5.26∼5.35(0.5H,m),5.35∼5.48(0.5H,m),5.91∼6.01(1.5H,m), 6.05(0.5H,d,J=7 Hz),7.34∼7.49(2H, m), 7.50∼7.65(2H,m),7.81(1H,d,J=7.9 Hz), 7.91(1H,d,J=7.9 Hz),7.99(0.5H,d,J=7.9 Hz),8.01(0.5H,d,J=7.9 Hz)

EXAMPLE 2

(2S,3R,4S)-4-{L-N-[(2S)-3-[(2RS)-3-pivaloyloxy-2-hydroxypropyl]sulfonyl-2-(1-naphthylmethyl)propionyl]norleucyl}amino-5-cyclohexyl-1-morpholino-2,3-pentanediol (a) 105.7 mg of the compound obtained in Example 1(7b) was dissolved in 1.8 ml of dry pyridine, and 46 μl of pivaloyl chloride was added thereto under cooling with ice and stirring. The mixture was stirred at room temperature overnight. Then, a small amount of water was added to the reaction solution, and the mixture was diluted with 50 ml of ethyl acetate. The ethyl acetate layer was washed sequentially with 1N hydrochloric acid, with water, with a saturated sodium hydrogencarbonate aqueous solution and with a saturated sodium chloride aqueous solution and dried over anhydrous sodium sulfate. The solvent was distilled off under reduced pressure, and then the residue was purified by silica gel column chromatography (n-hexane/ethyl acetate=2/1) to obtain 89.9 mg of L-N-[(2S)-3-[(2RS)-3-pivaloyloxy-2-hydroxypropyl]thio-2-(1-naphthylmethyl)propionyl]norleucine tert-butyl ester as colorless oily substance.

Rf value: 0.40 (n-hexane/ethyl acetate=2/1)

(b) 89.9 mg of the compound obtained in Example 2(a) was subjected to oxidation to form a sulfone compound in the same manner as in Example 1(8a) by using hydrogen peroxide-sodium tungstate, and then the sulfone compound was treated with TFA in the same manner as in Example 1(8b) to obtain 76.4 mg of L-N-[(2S)-3-[(2SR)-3-pivaloyloxy-2-hydroxypropyl]sulfonyl-2-(1-naphthylmethyl)propionyl]norleucine as colorless oily substance. Then, the compound was subjected to coupling reaction with 73 mg of (2S,3R,4S)-4-amino-5-cyclohexyl-1-morpholino-2,3-pentanediol dihydrochloride by DPPA method in the same manner as in Example 1(9) to obtain 16.1 mg of the above-identified compound as white powder.

Rf value: 0.55 (chloroform/methanol=10/1) Mass spectrum (FAB) m/z 819(M+1)+ δ ppm : 0.78~0.92(3H,m.),0.92~1.80(28H,m), 2.38~2.81(6H,m),2.81~3.53(9H,m), 3.53~3.84(5H,m),3.84~4.45(5H,m), 5.98~6.10(1.5H,m),6.10~6.19(0.5H, d,J=7 Hz),7.28~7.48(2H,m),7.50~7.65(2H,m),7.79(1H,d,J=-7.9 Hz), 7.89(1H,d,J=7.9 Hz),7.99(0.5H,d, J=7.9 Hz),8.01(0.5H,d,J=7.9 Hz)

EXAMPLE 3

(2S,3R,4S)-4-{L-N-[(2S)-3-(2-acetoxyethyl)sulfonyl-2-(1-naphthylmethyl)propionyl]norleucyl}amino-5-cyclohexyl-1-morpholino-2,3-pentanediol (1) (2RS)-3-(2-hydroxyethyl)thio-2-(1-naphthylmethyl)propionic acid (a) 3.2 g of sodium hydride (60% in oil) was washed three times with n-pentane, and dried in an argon stream. The powder thereby obtained was suspended in 30 ml of dry DMF under an argon stream, and 17.9 g of ethyl diethylphosphonoacetate was dropwise added thereto at 0° C. under stirring over a period of 1 hour. The mixture was stirred at room temperature for 1 hour and again cooled to 0° C. 17.0 g of 1-(chloromethyl)-naphthalene was dropwise added thereto under stirring over a period of 50 minutes. The mixture was stirred at 55° C. overnight. Then, 160 ml of water was added to the reaction solution, and the mixture was extracted with ethyl acetate (80 ml×3). The ethyl acetate layer was washed with a saturated sodium chloride aqueous solution and dried over anhydrous sodium sulfate. Then, the solvent was distilled off. The syrup thereby obtained was purified by silica gel column chromatography (n-hexane/ethyl acetate=2/3) to obtain 28.7 g of ethyl 2-diethylphosphono-3-(1-naphthyl) propionate as colorless oily substance.

Rf value: 0.37 (n-hexane/ethyl acetate=1/2)

1.92 g of lithium chloride was suspended in 50 ml of dry THF, and 15 g of the compound obtained in Example 3(1a) was dropwise added thereto. Then, 16 ml of a 50% dry THF solution of 1,5-diazabicyclo[5,4,0]undeca-5-ene (hereinafter referred to simply as DBU) was dropwise added thereto, and a suspension of 2.01 g of paraformaldehyde in dry THF was added thereto. The mixture was stirred at room temperature for 3 hours. Insolubles were removed by filtration and washed with a small amount of diethyl ether. The filtrate and the washing solution was put together, and the solvent was distilled off. The syrup thereby obtained was dissolved in 180 ml of diethyl ether. The diethyl ether layer was washed sequentially with a 10% citric acid aqueous solution, with water and with a saturated sodium chloride aqueous solution and dried over anhydrous sodium sulfate. The syrup obtained by the evaporation of the solvent was purified by silica gel column chromatography (n-hexane/diethyl ether=20/1) to obtain 6.48 g of ethyl 2-(1-naphthyl)methyl-2-propenoate as colorless oily substance.

Rf value: 0.45 (n-hexane/ethyl acetate=10/1) NMR (300 MHz, CDCl$_3$) δ ppm : 1.33(3H,t,J=6.9 Hz),4.10(2H,s), 4.27(2H,q,J=6.9 Hz),5.16(1H,d,J=1.5 Hz ), 6.24(1H,d,J=1.5 Hz),7.35(1H,d,J=8 Hz),7.40~7.52(3H),7.78(2H,d,j=8 Hz ),7.82~7.95(2H)

(c) 2.04 g of the compound obtained in Example 3(1b) was dissolved in 714 μl of 2-mercaptoethanol, and 102 mg of potassium tert-butoxide was added thereto at room temperature under stirring. The mixture was stirred at room temperature for 15 minutes. 500 μl of 2-mercaptoethanol was added thereto, and the mixture was further stirred for 15 minutes. Then, the reaction solution was diluted with 150 ml of diethyl ether. The diethyl ether layer was washed with water and with a saturated sodium chloride aqueous solution and dried over anhydrous sodium sulfate. The solvent was distilled off under reduced pressure to obtain 2.81 g of ethyl (2RS)-3-(2-hydroxyethyl)thio-2-(1-naphthylmethyl)propionate as colorless oily substance.

Rf value: 0.43 (n-hexane/ethyl acetate=1/1) NMR (300 MHz, CDCl$_3$) δ ppm : 1.08(3H,t,J=7.5 Hz),2.40(1H, br), 2.63(2H, t,J=5.9 Hz),2.69(1H,m), 2.84(1H,m),3.04(1H,m),3.35(2H,m), 3.61(2H,t,J=5.9 Hz),4.04(2H,q,j=7.5 Hz ),7.30(2H,m),7.48(2H,m), 7.70(1H,d,J=7.9 Hz),7.82(1H,d,J=7.9 Hz),8.00(1H,d,J=7.9 Hz )

(d) 151 mg of the compound obtained in Example 3(1c) was dissolved in 0.9 ml of an ethanol/water (10/1) solution, and 1.18 ml of a 2N potassium hydroxide ethanol/water (10/1) solution was added thereto. The mixture was stirred at room temperature for 2 hours. Then, the reaction solution was concentrated under reduced pressure. Water was added to the concentrate, and pH was adjusted to 2 with 2N hydrochloric acid at 0° C. under stirring. Then, the mixture was extracted with ethyl acetate. The ethyl acetate layer was washed with water and with a saturated sodium chloride aqueous solution and dried over anhydrous sodium sulfate. Then, the solvent was distilled off. The residue thereby obtained was purified by silica gel column chromatography (chloroform/ethyl acetate/acetic acid=6/3/0.1) to obtain 82 mg of (2RS) -3-(2-hydroxyethyl)thio-2-(1-naphthylmethyl)propionic acid as colorless solid.

Rf value: 0.28 (chloroform/methanol/acetic acid=10/0.5/0.1) NMR (300 MHz, CDCl$_3$) δ ppm : 2.68(2H,t,J=5.7 Hz),2.74(1H,m), 2.86(1H,m),3.14(1H,m),3.33(1H,dd, J=6.3,13.8 Hz),3.57(1H,dd,J=6.3, 13.8 Hz),3.64(2H,t,J=5.7 Hz),7.38(2H,m),7.52(2H,m),7.77(1H,d,J=7.2 Hz),7.88(1H,dd,J=1.8,7.8 Hz), 8.60(1H,d,J=8.4 Hz)

(2) L-N-[(2S)-3-(2-acetoxyethyl)thio-2-(1-naphthylmethyl)propionyl]norleucine tert-butyl ester (a) 80 mg of the compound obtained in Example 3(1d) was dissolved in 0.7 ml of dry DMF, and 56.9 mg of L-norleucine tert-butyl ester, 68.6 mg of 1-hydroxybenzotriazole and 79.2 mg of DCC were added thereto at 0° C. under stirring. The mixture was stirred at room temperature overnight. Precipitated dicyclohexylurea was removed by filtration, and the filtrate was diluted with 20 ml of ethyl acetate. The ethyl acetate layer was washed with a 10% citric acid aqueous solution, with water and with a saturated sodium chloride aqueous solution and dried over anhydrous sodium sulfate. Then, the solvent was distilled off. The residue was purified by silica gel column chromatography (chloroform/ethyl acetate=7/1) to obtain 35.7 mg of the isomer (2S) having a high Rf value of L-N-[(2RS)-3-(2-(hydroxyethyl)thio-2-(1-naphthylmethyl)propionyl]-norleucine tert-butyl ester, and 15.9 mg of the isomer (2R) having a low Rf value and 32.3 mg of the mixture thereof.

Isomer (2S) having a high Rf value:
Rf value: 0.60 (chloroform/ethyl acetate=1/1) NMR (300 MHz, CDCl$_3$) δ ppm : 0.85(3H,t,J=7.1 Hz),1.00~2.00(15H),2.64(2H,t,J=5.1 Hz),2.68~2.84(3H),2.96(1H,m),3.32(2H,m), 3.66(2H,d,J=5.1 Hz),4.35(1H,m), 6.10(1H,d,J=7.9 Hz),7.26~7.40(2H),7.44~7.60(2H),7.72(1H,d,J=7.9 Hz),7.84(1H,d,J=7.9. Hz),8.04(1H,d,J=7.9 Hz)

Isomer (2R) having a low Rf value:
Rf value: 0.52 (chloroform/ethyl acetate=1/1)

(b) 66.4 mg of L-N-[(2S)-3-(2-hydroxyethyl)thio-2-(1-naphthylmethyl)propionyl]norleucine tert-butyl ester was dissolved in 0.5 ml of dry pyridine, and 0.3 ml of acetic anhydride was added thereto. The mixture was stirred at room temperature for 2 hours. The work up was conducted in the same manner as in Example 1 to obtain 74.7 mg of the above-identified compound as colorless oily substance.

Rf value: 0.34 (n-hexane/ethyl acetate=3/1)

(3) (2S,3R,4S)-4-{L-N-[(2S)-3-(2-acetoxyethyl)sulfonyl-2-(naphthylmethyl)propionyl]norleucyl}amino-5-cyclohexyl-1-morpholino-2,3-pentanediol 74.7 mg of the compound obtained in Example 3(2b) was subjected to oxidation to form a sulfone compound in the same manner as in Example 1(8) by using hydrogen peroxide-sodium tungstate, and treated with TFA to obtain 55 mg of L-N-[(2S)-3-(2-acetoxyethyl)sulfonyl-2-(1-naphthylmethyl)propionyl]norleucine as colorless oily substance. Then, the coupling reaction with 54.1 mg of (2S,3R,4S)-4-amino-5-cyclohexyl-1-morpholino-2,3-pentanediol dihydrochloride was conducted by DPPA method in the same manner as in Example 1(9) to obtain 51.4 mg of the above-identified compound as white powder.

Rf value: 0.29 (chloroform/methanol=20/1) Mass spectrum (FAB) m/z 746(M+1)$^+$ NMR (300 MHz, CDCl$_3$) δ ppm : 0.74~1.02(4H,m),1.05~1.80(19H,m), 1.96(3H,s),2.35~2.78(6H,m),2.99~3.21(3H,m),3.21~3-.49(5H,m),3.49~3.71(5H,m),4.13~4.28(2H,m),4.28~4-.40(2H,m ),4.53(1H,bs),5.88~6.00(2H),7.28~7.43(2H,m) ,7.43~7.60(2H,m),7.75(1H,d,J =7.9 Hz),7.85(1H,d,J=7.9 Hz),7.96(1H,d,J=7.9 Hz)

EXAMPLE 4

(2S,3R,4S)-4-{(L-N-[(2S),-3-(2-pivaloyloxyethyl)sulfonyl-2-(1-naphthylmethyl)propionyl]norleucyl}amino-5-cyclohexyl-1-morpholino-2,3-pentanediol (a) 72.3 mg of L-N-[(2S)-3-(2-hydroxyethyl)thio-2-(1-naphthylmethyl)propionyl]norleucine tert-butyl ester was dissolved in 1.5 ml of dry pyridine, and 25 μl of pivaloyl chloride was added thereto. The mixture was stirred at room temperature overnight. The work up was conducted in the same manner as in Example 2(a), and then the residue was purified by silica gel column chromatography (n-hexane/ethyl acetate=4/1) to obtain 86 mg of L-N-[(2S)-3-(2-pivaloyloxyethyl)thio-2-(1-naphthylmethyl)propionyl]norleucine tert-butyl ester as colorless oily substance.

Rf value: 0.46 (n-hexane/ethyl acetate=3/1)

(b) 86 mg of the compound obtained in Example 4(a) was subjected to oxidation to form a sulfone compound in the same manner as in Example-1 by using hydrogen peroxide-sodium tungstate, and then treated with TFA. Then, 66 mg of L-N-[(2S)-3-(2-pivaloyloxyethyl)sulfonyl-2-(1-naphthylmethyl)propionyl]norleucine thereby obtained was subjected to coupling reaction with 59 mg of (2S,3R,4S)-amino-5-cyclohexyl-1-morpholino-2,3-pentanediol dihydrochloride by DPPA method to obtain 70.1 mg of the above-identified compound as white powder.

Rf value: 0.38 (chloroform/methanol=20/1) Mass spectrum (FAB) m/z. 788(M+1)$^+$ NMR (300 MHz, CDCl$_3$) δ ppm : 0.75~1.01(4H,m),1.01~1.80(28H,m), 2.37~2.79(6H,m),3.01~3.23(3H,m ), 3.23~3.49(5H,m),3.52~3.71(5H,m), 4.12~4.27(2H,m),4.27~4.38(2H,m), 5.85~5.94(2H),7.28 ~7.43(2H,m), 7.45~7.60(2H,m),7.75(1H,d,J=7.9 Hz),7.85(1H,d,J=7.9 Hz),7.94(1H,d, J=7.9 Hz)

EXAMPLE 5

(2S,3R,4S)-4-{L-N-[(2S)-3-(2-ethoxycarbonyloxyethyl)sulfonyl-2-(1-naphthylmethyl)propionyl]norleucyl}amino-5-cyclohexyl-1-morpholino-2,3-pentanediol (a) 99 mg of L-N-[(2S)-3-(2-hydroxyethyl)sulfonyl-2-(1-naphthylmethyl)propionyl]norleucine tert-butyl ester was dissolved in 4 ml of dry pyridine, and 87.2 mg of ethyl chloroformate was added thereto. The mixture was stirred at room temperature overnight. The reaction solution was concentrated under reduced pressure, and the residue thereby obtained was purified by silica gel column chromatography (n-hexane/ethyl acetate=3/1). The fractions containing the desired compound were put together and concentrated under reduced pressure. The residue thereby obtained was dissolved in 30 ml of ethyl acetate. Ethyl acetate layer was washed with a 10% citric acid aqueous solution, with a 4% sodium hydrogencarbonate aqueous solution and with a saturated sodium chloride aqueous solution and then dried over anhydrous sodium sulfate. The solvent was distilled off under reduced pressure to obtain 92 mg of L-N-[(2S)-3-(2-ethoxycarbonyloxyethyl)sulfonyl-2-

(1-naphthylmethyl)propionyl]norleucine tert-butyl ester as slightly yellow oily substance.

Rf value: 0.50 (n-hexane/ethyl acetate=1/1) NMR (300 MHz, CDCl$_3$) δ ppm : 0.84(3H,t,J=7.2 Hz),1.26(4H,m), 1.31(3H,t,J=7.2 Hz),1.37(9H,s), 1.58(1H,m),1.72(1H,m),3.09~3.50(6H),3.82(1H,dd,J=-9.0,14.1 Hz), 4.22(2H,q,J=7.2 Hz),4.24(1H),4.48(2H,m),5.90 (1H,d,J=7.9 Hz),7.28~7.40(2H),7.45~7.61(2H),7.74(1H,d,J=8.1 Hz ), 7.86(1H,d,J=8.1 Hz),8.02(1H,d,J=8.4 Hz)

(b) 88.7 mg of the compound obtained in Example 5(a) was dissolved in 1 ml of TFA, and the mixture was stirred at room temperature for 25 minutes. TFA was evaporated under reduced pressure. The residue was solidified by diethyl ether-n-hexane, and the solvent was distilled off to obtain 77.1 mg of L-N-[(2S)-3-(2-ethoxycarbonyloxyethyl)sulfonyl-2-(1-naphthylmethyl)propionyl]norleucine as colorless solid.

Rf value: 0.44 (chloroform/methanol/acetic acid=10/0.5/0.1) NMR (300 MHz, CDCl$_3$) δ ppm : 0.85(3H,t,J=6.9 Hz),1.26(4H,m), 1.31(3H,t,J=7.1 Hz),1.60(1H,m), 1.78(1H,m),3.20(2H,m),3.29~3.50(4 H),3.85(1H,dd,J=8.7,14.1 Hz), 4.22(2H,q,J=7.1 Hz),4.40(1H,m), 4.49(2H,m),5.92 (1H,d,J=7.9 Hz), 7.29~7.41(2H),7.43~7.60(2H),7.74(1H,d,J=8.1 Hz),8.01(1H,d,J=8.4 Hz)

(c) 77.1 mg of the compound obtained in Example 5(b) was dissolved in 0.2 ml of dry DMF, and 23.1 mg of triethylamine and 52.3 mg of DPPA were added thereto at −15° C. under stirring. The mixture was stirred at the same temperature for 5 minutes. Then, 65.8 mg of (2S,3R,4S)-4-amino-5-cyclohexyl-1-morpholino-2,3-pentanediol dihydrochloride was dissolved in 0.3 ml of dry DMF, and 37.1 mg of triethylamine was added thereto. This DMF solution was added to the above-mentioned reaction solution at −15° C. under stirring, and the mixture was stirred at the same temperature for 2 hours and at 5° C. overnight. 40 ml of ethyl acetate was added to the reaction solution, and the ethyl acetate layer was washed with water and with a saturated sodium chloride aqueous solution and dried over anhydrous sodium sulfate. The solvent was distilled off under reduced pressure, and the residue was purified by silica gel column chromatography (chloroform/methanol=100/1) to obtain 82 mg of the above-identified compound as colorless solid.

Rf value: 0.47 (chloroform/methanol=15/1) Mass spectrum FAB) m/z 776(M+1)+ NMR (300 MHz, CDCl$_3$) δ ppm : 0.78~1.07(6H),1.07~1.82(19H), 2.49(2H,m),2.61(1H),2.75(2H), 2.80(1H),3.09~3.51(1H),3.57~3.78(5H),4.12~4.32(4-H),4.46(2H,t,J=5.9 Hz),4.60(1H),5.90(1H,d,J=6.3 Hz),5.97(1H,d,J=7.9 Hz),7.32~7.48(2H),7.48~7.68(2H),7.80(1H,d,J=8.1 Hz),7.90(1H,d,J=7.8 Hz),8.00(1H,d,J=8.4 Hz)

EXAMPLE 6

(2S,3R,4S)-4-{L-N-[(2S)-3-[(2RS)-2,3-diacetoxypropyl]sulfinyl-2-(1-naphthylmethyl)propionyl]norleucyl}amino-5-cyclohexyl-1-morpholino-2,3-pentanediol (a) 125 mg of the compound obtained in Example 1(7c) was dissolved in 1.5 ml of methanol, and 0.35 ml of a 30% aqueous hydrogen peroxide was added thereto. The mixture was stirred at room temperature overnight, and then treated in the same manner as in Example 1(8a) to obtain 124 mg of L-N-[(2S)-3-[(2RS)-2,3-diacetoxypropyl]sulfinyl-2-(1-naphthylmethyl)propionyl]norleucine tert-butyl ester as colorless oily substance.

Rf value: 0.38 (n-hexane/ethyl acetate=½)

(b) 124 mg of the compound obtained in Example 6(a) was treated with TFA in the same manner as in Example 1(8b), and the carboxylic acid thereby obtained was subjected to coupling with 94.6 mg of (2S,3R,4S)-4-amino-5-cyclohexyl-1-morpholino-2,3-pentanediol dihydrochloride in the same manner as in Example 1(9) to obtain 35.6 mg of the isomer having a high Rf value of the above-identified compound, and 24.9 mg of the isomer having a low Rf value as white powder, respectively.

Isomer having a high Rf value:

Rf value: 0.49 (chloroform/methanol=10/1) Mass spectrum (FAB) m/z 802(M+1)+ NMR (300 MHz, CDCl$_3$) NMR (300 MHz, CDCl$_3$) δ ppm : 0.80~0.92(3H,m),0.92~1.07(1H,m), 1.10~1.87(18H,m),1.99(1.5H,s), 2.01~2.11(4.5 H,m),2.22~2.92(8H,m), 3.10~3.84(11H,m),3.94~4.02(0.5H,m),4.10~4.35(2.5-H,m),4.57~4.75(1H,m),4.80~4.90(0.5H,m), 5.22~5.31(0.5H,m),6.22(0.5H,d,J=8.2 Hz),6.32(0.5H,d,J=8.2 Hz),6.80(0.5H,d,J=6.4 Hz),6.96(0.5H,d,J=6.4 Hz),7.31~7.48(2H,m),7.48~7.65(2H,m),7.79(1H,d,J=-7.9 Hz),7.89(1H,d,J=7.9 Hz),7.98(1H,d,J=7.9 Hz)

Isomer having a low Rf value:

Rf value: 0.44 (chloroform/methanol=10/1) Mass spectrum (FAB) m/z 802(M+1)+ NMR (300 MHz, CDCl$_3$) δ ppm : 0.75~1.06(4H,m),1.10~1.94(18H,m), 2.03(5H,s),2.06(4.5H,s),2.36~3.08(9H,m),3.08~3.75(1-0H,m),4.06~4.72(4H,m),5.31~5.48(1H,m),6.08(1H,d,J-=7.9 Hz),6.22(1H,bs),7.32~7.48(2H,m),7.48~7.65 (2H,m),7.78(1H,d,J=7.9 Hz),7.89 (1H,d,J=7.9 Hz),8.04(1H,d,J=7.9 Hz)

EXAMPLE 7

(2S,3R,4S)-4-{L-N-[(2S)-3-[(2RS)-2,3,-diacetoxypropyl]thio-2-(1-naphthylmethyl)propionyl]norleucyl-}amino-5-cyclohexyl-1-morpholino-2,3-pentanediol 138.5 mg of the compound obtained in Example 1(7c) was treated with TFA in the same manner as in Example 1(8b)–(9), and then subjected to coupling with 101.6 mg of (2S,3R,4S)-4-amino-5-cyclohexyl-1-morpholino-2,3-pentanediol dihydrochloride to obtain 121.6 mg of the above-identified compound as white powder.

Rf value: 0.27 (chloroform/methanol=20/1) Mass spectrum (FAB) m/z 786(M+1)+ NMR (300 MHz, CDCl$_3$) δ ppm : 0.8~1.05(4H,m),1.05~1.84(18H,m), 2.01(1.5H,s),2.05(1.5H,s),2.06(1.5H,s),2.07(1.5H,s),2.41-~3.07(10H,m),3.27~3.76(8H,m),4.00~4.48(7H,m),4.6-3(1H,bs),4.95~5.07(1H,m),5.97(0.5H,d,J=7.1 Hz),6.02(0.5H,d,J=7.1 Hz),6.06(0.5H,d,J=7.1 Hz),6.16(0.5H,d,J=7.1 Hz),7.35~7.61(4H,m),7.76(1H,d,J=7.9 Hz) 7.89(1H,d,J=7.9 Hz),8.05(1H,d,J=7.9 Hz)

EXAMPLE 8

(2S,3R,4S)-4-{L-N-[(2S)-3-[(2RS)-2,3-dipropionyloxypropyl]sulfonyl,-2-(1-naphthylmethyl)propionyl]norleucyl}amino-5-cyclohexyl-1-morpholino-2,3-pentanediol (a) 135 mg of the compound obtained in Example 1(7b) was dissolved in 1.4 ml of dry dichloromethane, and 115 μl of triethylamine, 110 μl of propionic anhydride and 6 mg of dimethylaminopyridine were added thereto. The mixture was stirred at room temperature for 2 hours. A small amount of water was added to the reaction solution, and then the mixture was diluted with ethyl acetate and washed sequentially with 1N hydrochloric acid, with water, with a saturated sodium hydrogencarbonate aqueous solution and with a saturated sodium chloride aqueous solution. The organic layer was dried over anhydrous sodium sulfate. Then, the solvent was distilled off under reduced pressure, and the residue was purified by silica gel column chromatography (n-hexane/ethyl acetate=3/1) to obtain 188 mg of L-N-[(2S)-3-[(2RS)-2,3-dipropionyloxypropyl]thio-2-(1-naphthylmethyl)propionyl]norleucine tert-butyl ester as colorless oily substance.

Rf value: 0.51 (n-hexane/ethyl acetate=2/1)

(b) 119.5 mg of the compound obtained in Example 8(a) was subjected to oxidation to form a sulfone compound in the same manner as in Example 1(8) by using hydrogen peroxide-sodium tungstate, and then treated with TFA. Then, the coupling with 87 mg of (2S,3R,4S)-4-amino-5-cyclohexyl-1-morpholino-2,3-pentanediol dihydrochloride was conducted by DPPA method disclosed in Example 1(9) to obtain 88 mg of the above-identified compound as white powder.

Rf value: 0.65 (chloroform/methanol=20/1) Mass spectrum (FAB) m/z 846(M+1)+ NMR (300 MHz, CDCl3) δ ppm : 0.72~1.01(4H,m),1.01~1.87(24H,m), 2.04~2.84(10H,m),2.90~3.54(8H,m), 3.54~3.82(5H,m),3.95~4.09(1H,m), 4.09~4.70(4H,m),5.27~5.38(0.5H,m) 5.38~5.51(0.5H,m),5.91~6.01(2H,m),7.29~7.65(4H,m),7.80(1H,d, J=7.9 Hz),7.90(1H,d,J=7.9 Hz),7.95~8.04(1H,m)

EXAMPLE 9

L-N-[(2S)-3-[(2RS)-3-acetoxy-2-hydroxypropyl]thio-2-(1-naphthylmethyl)propionyl]norleucine tert-butyl ester 103 mg of the compound obtained in Example 1(7b) was dissolved in 1.0 ml of dry dichloromethane, and 31 μl of triethylamine and 13 μl of acetyl chloride were added thereto. The mixture was stirred at room temperature for hours, and then diluted with 30 ml of ethyl acetate. The ethyl acetate layer was washed sequentially with water, with a saturated sodium hydrogencarbonate aqueous solution and with a saturated sodium chloride aqueous solution and dried over anhydrous sodium sulfate. Then, the solvent was distilled off under reduced pressure, and the residue was purified by silica gel column chromatography (n-hexane/ethyl acetate=2/1) to obtain 73.6 mg of the above-identified compound as colorless oily substance.

Rf value: 0.15 (n-hexane/ethyl acetate=2/1) NMR (300 MHz, CDCl3) δ ppm : 0.86(3H,t,J=8.0 Hz),1.11~1.48(5H, m),1.42(9H,s),1.70~1.84(1H,m), 2.09(3H,s),2.45~2.81(4H,m)2.91~3.08(1.5H,m),3.20(0.5 H,d,J=4.0 Hz), 3.21~3.48(2H,m),3.68~3.79(0.5H,m),3.79~3.92(0.5H,m),4.04~4.19(2H,m),4.30~4.40(1H,m),5.93~6.04(1H,m),7.22~7.40(2H,m),7.42~7.60(2H,m),7.72(1H,d,J=7.9 Hz), 7.85(1H,d,J=7.9 Hz),8.02(1H,d,J=7.9 Hz)

EXAMPLE 10

The following compound was obtained in the same manner as in Example 9 except that propionyl chloride was used instead of acetyl chloride.

L-N-[(2S)-3-[(2RS)-3-propionyloxy-2-hydroxypropyl]thio-2-(naphthylmethyl)propionyl]norleucine tert-butyl ester Rf value: 0.22 (n-hexane/ethyl acetate=2/1) NMR (300 MHz, CDCl3) δ ppm : 0.85(3H,t,J=7.9 Hz),1.15(3H,t,J=7.9 Hz),1.40(9H,s),1.02~1.66(5H,m), 1.66~1.84(1H,m),2.34(2/2H,q, J=7.9 Hz),2.35(2/2H,q,J=7.9 Hz), 2.43~2.82(4H,m),2.89~3.09(1.5H,m), 3.16(0.5H,d,J=4.0 Hz),3.20~3.47(2H,m),3.79~3.94(1H,m),4.05~4.18(2H,m),4.30~4.40(1H,m),5.91~6.05(1H,m),7.22~7.41(2H,m), 7.41~7.60(2H,m),7.71(1H,d,J=7.9 Hz), 7.85(1H,d,J=7.9 Hz),8.01(1H,d, J=7.9 Hz)

EXAMPLE 11

(2S,3R,4S)-4-{L-N-[(2RS)-3-acetoxy-2-hydroxypropyl]sulfonyl-2-(1-naphthylmethyl)propionyl]norleucyl}amino-5-cyclohexyl-1-morpholino-2,3-pentanediol 72.1 mg of the compound obtained in Example 9 was oxidized to a sulfone compound in the same manner as in Example 1(8)-(9), then treated with TFA and subjected to coupling with 53 mg of (2S,3R,4S)-4-amino-5-cyclohexyl-1-morpholino-2,3-pentanediol dihydrochloride by DPPA method to obtain 56.3 mg of the above-identified compound as white powder.

Rf value: 0.47 (chloroform/methanol=10/1) Mass spectrum (FAB) m/z 776(M+1)+ NMR (300 MHz, CDCl3) δ ppm : 0.71~1.01(4H,m),1.01~1.95(18H), 2.05(1.5H,s),2.06(1.5H,s),2.32~2.80(6H,m),2.80~3.51(-8H,m),3.51~3.80(5H,m),3.82~4.71(5H,m),5.91~6.18(-2H,m),7.26~7.42(2H,m),7.42~7.60(2H,m),7.76(1H,d,J=7.9 Hz), 7.86(1H,d,J=7.9 Hz),7.94(0.5H,d, J=7.9 Hz), 7.96(0.5 H,d,J=7.9 Hz)

EXAMPLE 12

(2S,3R,4S)-4-{L-N-[(2S)-3-[(2RS)-3-propionyloxy-2-hydroxypropyl]sulfonyl-2-(1-naphthylmethyl)propionyl]norleucyl}amino-5-cyclohexyl-1-morpholino-2,3-pentanediol 63 mg of the compound obtained in Example 10 was treated in the same manner as in Example 1(8)-(9) to obtain 50.5 mg of the above-identified compound as white powder.

Rf value: 0.57 (chloroform/methanol=10/1) Mass spectrum (FAB) m/z 790(M+1)+ NMR (300 MHz, CDCl3) δ ppm : 0.71~1.06(4H,m),1.06~1.85(21H,m), 2.30~2.41(2H,m),2.41~2.56(2H,m), 2.56~2.85(4H,m),2.85~3.56(8H,m), 3.56~4.81(5H,m),3.88~4.78(7H,m), 5.95~6.09(1.5H,m),6.15(0.5H,d,J=7.9Hz),7.31~7.48(-2H,m),7.48~7.64(2H,m),7.79(1H,d,J=7.9 Hz),7.90(1H,d,J=7.9 Hz),7.98(0.5H,d,J=7.9 Hz),8.01(0.5H,d,J=7.9 Hz)

EXAMPLE 13

(2S,3R,4S)-4-{L-N-[(2S)-3-[(2RS)-2-acetoxy-3-propionyloxypropyl]sulfonyl-2-(1-naphthylmethyl)propionyl]norleucyl}amino-5-cyclohexyl-1-morpholino-2,3-pentanediol 96.7 mg of the compound obtained in Example 10 was acetylated in the same manner as in Example 1(7c), followed by the treatment in the same manner as in Example 1(8)-(9) to obtain 73.7 mg of the above-identified compound as white powder.

Rf value: 0.29 (chloroform/methanol=20/1) Mass spectrum (FAB) m/z 832(M+1)+ NMR (300 MHz, CDCl3) δ ppm : 0.75~1.05(4H,m),1.14(1.5H,t,J=7.9 Hz),1.15 (1.5H,t,J=7.9 Hz),1.05~1.84(18H,m),1.95(1.5H,s),2.08(1.5H,s),2.34(-

2H,q,J=7.9 Hz),2.40~2.55(2H,m),2.55~2.85(4H,m),2.85~3.53(10H,m),3.53~3.85(5-H,m), 3.95~4.07(1H,m),4.07~4.35(3H,m),4.60(1H,bs),5.26~5.38(0.5H,m),
5.38~5.49(0.5H,m),5.91~6.05(1.5H,m),
6.09(0.5H,d,J=6.3 Hz),7.31~749 (2H,m),7.49~7.65(2H,m),7.80(1H,d,J=7.9 Hz),7.90(1H,d,J=7.9 Hz),7.99(0.5H,d,J=7.9 Hz),8.00(0.5H,d,J=7.9 Hz)

EXAMPLE 14

(2S,3R,4S)-4-{L-N-[(2S)-3-[(2RS)-2-methoxy-3-propionyloxypropyl]sulfonyl-2-(1-naphthylmethyl)propionyl]norleucyl}amino-5-cyclohexyl-1-morpholino-2,3-pentanediol (a) 59 mg of the compound obtained in Example 10 was dissolved in 1.0 ml of dry DMF, and 0.1 ml of methyl iodide and 8.6 mg of sodium hydride (60% in oil) were added thereto. The mixture was stirred at room temperature for 2 hours. The reaction solution was diluted with ethyl acetate, washed sequentially with 1N hydrochloric acid, with water, with a saturated sodium hydrogencarbonate aqueous solution and with a saturated sodium chloride aqueous solution and dried over anhydrous sodium sulfate. Then, the solvent was distilled off under reduced pressure, and the residue was purified by silica gel column chromatography (n-hexane/ethyl acetate =3/1) to obtain 42.7 mg of L-N-[(2S)-3-[(2RS)-2-methoxy-3-propionyloxypropyl]thio-2-(1-naphthylmethyl)propionyl]norleucine tert-butyl ester as colorless oily substance.

Rf value: 0.32 (n-hexane/ethyl acetate=2/1)

(b) 41 mg of the compound obtained in Example 14(a) was treated in the same manner as in Example 1(8)-(9) to obtain 24.5 mg of the above-identified compound as white powder.

Rf value: 0.24 (chloroform/methanol=20/1) Mass spectrum (FAB) m/z 804(M+1)+

EXAMPLE 15

(2S,3R,4S)-4-{L-N-[(2S)-3-[(2RS)-2,3-diacetoxypropyl]sulfonyl-2-benzylpropionyl]norleucyl}amino-5-cyclohexyl-1-morpholino-2,3-pentanediol (a) 1.2 g of the compound obtained in Example 1(2b) was subjected to Grignard reaction by using benzyl magnesium bromide (0.8M diethyl ether solution) in the same manner as in Example 1(2c) to obtain 975 mg of (2R,3R)-3-benzyl-4-benzyloxy-1-tert-butyldimethylsilyloxy-2-butanal as colorless oily substance. Then, the removal of a silyl group was conducted in the same manner as in Example 1(3)–(4) by using 5 ml of tetra-n-butylammonium fluoride (1M THF solution), followed by conversion to an aldehyde by using 625 mg of sodium metaperiodate and oxidation with chromic acid (John's reagent) to obtain 427 mg of (2R)-2-benzyl-3-benzyloxypropionic acid.

Rf value: 0.57 (n-hexane/ethyl acetate/acetic acid =6/6/0.2) Angle of rotation: $[\alpha]_D^{26}$=4.8° (C 0.765, CHCl3) Mass spectrum (FAB) m/z 293(M+Na)+271(M+1)+

(b) 420 mg of the compound obtained in Example 15(a) was dissolved in 5.5 ml of ethanol, and hydrogenation was conducted at a normal temperature under atmospheric pressure for 2 hours by using palladium black. Insolubles were removed by filtration, and then the solvent was distilled off under reduced pressure to obtain 290 mg of (2R)-2-benzyl-3-hydroxypropionic acid as colorless oily substance.

Rf value: 0.24 (n-hexane/ethyl acetate/acetic acid =6/6/0.2) Angle of rotation: $[\alpha]_D^{26}$=+4.9° (C 0.853, CHCl3) Mass spectrum (FAB) m/z-203(M+Na)+181(M+1)+

(c) 274 mg of the compound obtained in Example 15(b) was dissolved in 2 ml of dry DMF, and the coupling reaction with 322 mg of L-norleucine tert-butyl ester by DCC-HOBT method in the same manner as in Example 2(6) to obtain 306 mg of L-N-[(2S)-2-benzyl-3-hydroxypropionyl]norleucine tert-butyl ester as white solid.

Rf value: 0.25 (n-hexane/ethyl acetate=2/1)

(d) 70 mg of the compound obtained in Example 15(c) was treated in the same manner as in Example 1(7)–(9) to obtain 99.9 mg of the above-identified compound as white powder.

Rf value: 0.50 (chloroform/methanol=10/1) Mass spectrum (FAB) m/z 768(M+1)+ NMR (300 MHz, CDCl3) δ ppm : 0.80~1.08(5H,m),1.10~1.85(17H,m), 2.01(1.5H,s),2.10(4.5H,s),2.41~3.51(14H),3.5~3.85(5-H,m),4.01~4.68(4H),5.34~5.42(0.5H,m),5.42~5.58(0.-5H,m),5.89~6.00(1.5H,m), 6.05(0.5H,d,J=6.3 Hz),7.12~7.40(5H,m)

EXAMPLE 16

(2S,3R,4S)-4-{L-N-[(2S)-3-[(2RS)-2,3-diacetoxypropyl]thio-2-benzylpropionyl]norleucyl}amino-5-cyclohexyl-1-morpholino-2,3-pentanediol 97.5 mg of L-N-[(2S)-3-[(2RS)-2,3-diacetoxypropyl]thio-2-benzylpropionyl]norleucine tert-butyl ester was treated in the same manner as in Example 1(8b)–(9) to obtain 91.7 mg of the above-identified compound as white powder.

Rf value: 0.55 (chloroform/methanol=10/1) Mass spectrum (FAB) m/z 736(M+1)+ NMR (300 MHz, CDCl3) δ ppm : 0.75~1.05(5H,m),1.05~1.85(17H,m), 2.07(6H,s),2.36~3.03(13H,m),3.47(2H,bs),3.69(4H,bs),-4.06(0.5H,dd, J=7.1,11.9 Hz),4.12(0.5H,dd,J=7.1, 11.9 Hz),4.16~4.33(2H,m),4.45(0.5H,dd,J=14.2,3.1 Hz),4.60(1H, m),4.98~5.21(1H,m),5.92~6.06(1H, m),6.19(0.5H,d,J=7.1 Hz),7.12~7.38(5H,m)

EXAMPLE 17

(2S,3R,4S)-4- {L-N-[(2S)-3-[(2RS)-2,3-dipropionyloxypropyl]sulfonyl-2-benzylpropionyl]norleucyl}amino-5-cyclohexyl-1-morpholino-2,3-pentanediol 100.6 mg of L-N-[(2S)-3-[(2RS)-2,3-dihydroxypropyl]thio-2-benzylpropionyl]norleucine tert-butyl ester was treated in the same manner as in Example 8 to obtain 74.4 mg of the above-identified compound.

Rf value: 0.27 (chloroform/methanol=20/1) NMR (300 MHz, CDCl3) δ ppm : 0.78~1.07(4H,m),1.16(3H,t,J=7.9 Hz),1.17(3H,t,J=7.9 Hz),1.07~1.87(18H,m),2.15~2.90(10H,m),2.90~3.52(-8H,m),3.52~3.78(5H,m),4.05~4.42(4H,m),4.55(1H,bs)-,5.35~5.45(0.5H,m),5.45~5.56(0.5H,m),5.85~5.98(1.5-H,m),6.01(0.5H,d,J=7.9 Hz),7.18~7.40(5H,m)

EXAMPLE 18

(2S,3R,4S)-4-{L-N-[(2S)-3-(4-acetoxyphenylthio)-2-(1-naphthylmethyl)propionyl]norleucyl}amino-5-cyclohexyl-1-morpholino-2,3-pentanediol (a) 200 mg of L-N-[(2R)-2-(1-naphthylmethyl)-3-(p-toluenesulfonyloxy)propionyl]norleucine tert-butyl ester was dissolved in dry DMF, and 159 mg of 4-hydroxythiophenol and 141 mg of potassium tert-butoxide were added thereto. The mixture was treated in the same manner as in Example 1(7b) to obtain 164 mg of L-N-[(2S)-(4-hydroxyphenylthio)-2-(1-naphthylmethyl)propionyl]norleucine tert-butyl ester.

Rf value: 0.16 (hexane/ethyl acetate=3/1)

(b) 162 mg of the compound obtained in Example 18(a) was dissolved in 3 ml of dry pyridine, 0.5 ml of acetic anhydride was added thereto and treated in the same manner as in Example 1(7c) to obtain 164 mg of L-N-[(2S)--(4-acetoxyphenylthio)-2-(1-naphthylmethyl)propionyl]norleucine tert-butyl ester.

Rf value: 0.33 (hexane/ethyl acetate=3/1)

(c) 5.3 mg of the compound obtained in Example 18(b) was treated in the same manner as in Example 1(8b)–(9) to obtain 40.8 mg of the above-identified compound.

Rf value: 0.17 (chloroform/methanol=40/1) Mass spectrum (FAB) m/z 762(M+1)+ NMR (300 MHz, CDCl$_3$) δ ppm : 0.90(5H,m),1.22(8H,m),1.60(9H,m), 2.29(3H,s),2.49(2H,m),2.62(1H,m), 2.78(4H,m),3.08(1H,dd,J=4.5,13.5 Hz),3.20(1H,dd,J=9.0,13.5 Hz), 3.42(4H,m),3.68(4H,m),4.24 (2H,m), 4.59(1H,m),5.67(1H,d,J=6.3 Hz), 6.00(1H,d,J=7.9 Hz),6.88(3H,m), 7.11(2H,d,J=7.9 Hz),7.40(2H,m), 7.51(2H,m),7.78(1H,d,J=7.1 Hz), 7.91(2H,m)

EXAMPLE 19

(2S ,3R,4S)-4-{L-N-[(2S)-3-(4-acetoxyphenylsulfonyl)-2-(1-napthylmethyl)propionyl]norleucyl}amino-5-cyclohexyl-1-morpholino-2,3-pentanediol (a) 57.8 mg of L-N-[(2S)-3-(4-hydroxyphenylthio)-2-(1-naphthylmethyl)propionyl]norleucine tert-butyl ester was dissolved in 1 ml of acetic acid, and 320 μl of 30% aqueous hydrogen peroxide was added thereto. The mixture was stirred at room temperature overnight and subjected to azeotropic operation by using benzene to obtain 64.9 mg of L-N-[(2S)-3-(4-hydroxyphenylsulfonyl)-2-(1-naphthylmethyl)propionyl]norleucine tert-butyl ester.

Rf value: 0.35 (hexane/ethyl acetate=1/1)

(b) 64.9 mg of the compound obtained in Example 19(a) was treated in the same manner as in Example 1(8b)–(9) to obtain 26.2 mg of (2S,3R,4S)-4-[L-N-[(2S)-3-(4-hydroxyphenylsulfonyl)-2-(1-naphthylmethyl)propionyl]norleucyl)amino-5-cyclohexyl-1-morpholino-2,3-pentanediol.

Rf value: 0.12 (chloroform/methanol=20/1)

(c) 28 mg of the compound obtained in Example 19(b) was dissolved in 200 μl of dry dichloromethane, and 3.8 μl of acetic anhydride and 3.3 μl of pyridine were added thereto. The mixture was stirred at room temperature overnight. Water was added thereto, and the mixture was extracted with ethyl acetate, followed by purification by silica gel column chromatography (chloroform/methanol= 40/1) to obtain 8.1 mg of the above-identified compound.

Rf value: 0.39 (chloroform/methanol=20/1) Mass spectrum (FAB) m/z 794(M+1)+ NMR (300 MHz, CDCl$_3$) δ ppm : 0.90(5H,m),1.22(8H,m),1.60(9H,m), 2.35(3H,s ),2.48(2H,m),2.63(1H,m), 2.78(4H,m),3.33(6H,m),3.68(5H,m), 4.22(2H,m),4.63(1H,m),6.03(2H,m), 7.15(2H,d,J=7.9 Hz),7.31(2H,m), 7.52(2H,m),7.72(3H,m),7.88(2H,m)

EXAMPLE 20

(2S,3R,4S)-4-{(L-N-[(2S)-3-(4-acetoxyphenylsulfinyl)-2-(1-naphthylmethyl)propionyl]norleucyl}amino-5-cyclohexyl-1-morpholino-2,3-pentanediol (a) 126 mg of L-N-[(2S)-3-(4-hydroxyphenylthio)-2-(1-naphthylmethyl)propionyl]norleucine tert-butyl ester was treated in the same manner as in Example 1(8b) and (9) to obtain 107.2 mg of (2S,3R,4 S)-4-{L-N-[(2S)-3-(4-hydroxyphenylthio)-2-(1-naphthylmethyl)-propionyl]norleucyl}amino-5-cyclohexyl-1-morpholino-2,3-pentanediol.

Rf value: 0.2 (chloroform/methanol=20/1)

(b) 105 mg of the compound obtained in Example 20(a) was treated in the same manner as in Example 19(a) to obtain 103.4 mg of the mixture of the isomers of (2S,3R,4S)-4-{L-N-[(2S)-3-(4-hydroxyphenylsulfinyl)-2-(1-naphthylmethyl)propionyl]norleucyl}amino-5-cyclohexyl-1-morpholino-2,3-pentanediol.

Rf value: 0.31, 0.28 (chloroform/methanol=10/1)

(c) 103 mg of the compound obtained in Example 20(b) was treated in the same manner as in Example 19(c) to obtain 16.5 mg of isomer A resulted from the sulfoxide group of the above-identified compound, and 4.6 mg of isomer B and 10.7 mg of the mixture of isomers A and B.

Isomer A (isomer having a high Rf value):

Rf value: 0.33(chloroform/methanol=20/1) Mass spectrum (FAB) m/z 778(M+1)+ NMR (300 MHz, CDCl$_3$) δ ppm : 0.90(5H,m),1.25(8H,m),1.65(9H,m), 2.33(3H,s),2.47(2H,m),2.62(1H,m), 2.77(4H,m),3.14(4H,m),3.42(4H,m), 3.62(4H,m),4.29(2H,m),4.69(1H,m), 6.20(1H,d,J=8.7 Hz),6.96(2H,d,J=9.5 Hz),7.06(1H,d,J=6.3 Hz), 7.20 (2H,m),7.32(2H,m),7.45(2H,m), 7.78(3H,m)

Isomer B (isomer having a low Rf value):

Rf value: 0.30(chloroform/methanol=20/1) Mass spectrum (FAB) m/z 778(M+1)+ NMR (300 MHz, CDCl$_3$) δ ppm : 0.90(5H,m),1.23(8H,m),1.60(9H,m), 2.32(3H,s),2.48(2H,m),2.62(1H,m), 2.77(4H,m),2.95(1H,m),3.18(1H,m), 3.33(1H,m),3.47(3H,m),3.63(4H,m), 4.07(1H,m),4.25(1H,m),4.62(1H,m), 6.08(1H,d,J=8.7 Hz),6.16(1H,d,J=6.3 Hz),7.22(3H,m),7.45(5H,m), 7.80(1H,d,J=7.9 Hz),7.91(1H,d,J=7.9 Hz),8.10(1H,d,J=7.9 Hz)

EXAMPLE 21

(2RS)-3-[(2RS)-2,3-diacetoxypropyl]sulfonyl-2-(1-naphthylmethyl)propionic acid (a) 223 mg of ethyl 2-(1-naphthyl)methyl-2-propenoate was dissolved in 1 ml of dry DMF, reacted with 232 μl of α-thioglycerol in the same manner as in Example 3(1c) to obtain 320 mg of ethyl (2 RS[-3-[(2RS)-2,3-dihydroxypropyl]thio-2-(1-naphthylmethyl)propionate as colorless oily substance.

Rf value: 0.21(chloroform/ethyl acetate=1/1)

(b) 294 mg of the compound obtained in Example 21(a) was hydrolyzed by 1.02 ml of a 2N potassium hydroxide ethanol/water (10/1) solution in the same manner as in Example 3(1 d) to obtain 183 mg of (2RS)-3-[(2RS)-2,3-dihydroxypropyl]thio-2-(1-naphthylmethyl)propionic acid as colorless solid.

Rf value: 0.23(chloroform/methanol/acetic acid=10/1/0.1)

(c) 183 mg of the compound obtained in Example 21(b) was acetylated in the same manner as in Example 3(2b) to obtain 199 mg of (2RS)-3-[(2RS)-2,3-diacetoxypropyl]thio-2-(1-naphthylmethyl)propionic acid.

Rf value: 0.55(chloroform/methanol/acetic acid=10/1/0.1) Mass spectrum (FAB) m/z 443(M+K)+

(d) 228 mg of the compound obtained in Example 21(c) was sulfonated in the same manner as in Example 1(8) by hydrogen peroxide-sodium tungstate to obtain 177 mg of the above-identified compound as colorless solid.

Rf value: 0.52(chloroform/methanol/acetic acid=10/1/0.1) Mass spectrum (FAB) m/z 475(M+K)+

EXAMPLE 22

(2S,3R,4S)-4-(L-N$^{im}$-2,4-dinitrophenylhistidyl)amino-5-cyclohexyl-1-morpholino-2,3-pentanediol (a) 4 g of L-N$^α$-tert-butyloxycarbonylhistidine was suspended in 20.7 ml of a saturated sodium hydrogencarbonate aqueous solution, and a methanol solution (24 ml) of 3.25 g of 1-fluoro-2,4-dinitrobenzene was dropwise added thereto under shielding the light at room temperature under stirring. The reaction solution was stirred at room temperature for 3 hours and at 5° C. overnight and then concentrated under reduced pressure. The aqueous solution thereby obtained was extracted with diethyl ether, and then pH of the aqueous solution was adjusted to 3.5 with 1N hydrochloric acid under cooling with ice and extracted with ethyl acetate. The ethyl acetate layer thereby obtained was washed with a saturated sodium chloride aqueous solution and dried over anhydrous sodium sulfate. Then, the solvent was distilled off under reduced pressure. The residue was recrystallized from ethanol-petroleum ether to obtain 6.0 g of L-N$^α$-tert-butyloxycarbonyl-N$^{im}$-2,4-dinitrophenylhistidine as yellow solid.

Rf value: 0.32(chloroform/methanol/acetic acid=10/2/0.1)

(b) 763 mg of the compound obtained in Example 22(a) and 780 mg of (2S,3R,4S)-4-amino-5-cyclohexyl-1-morpholino-2,3-pentanediol dihydrochloride were subjected to coupling under shielding the light in the same manner as in Example 3(2a) to obtain 990 mg of (2S,3R,4S)-4-(L-N$^α$-tert-butyloxycarbonyl-N$^{im}$-2,4-dinitrophenylhistidyl)amino-5-cyclohexyl-1-morpholino-2,3-pentanediol as yellow solid.

Rf value: 0.43(chloroform/methanol=10/1)

(c) 171 mg of the compound obtained in Example 22(b) was dissolved in 0.5 ml of dry dichloromethane, and 0.4 ml of trifluoroacetic acid was added thereto. The mixture was stirred at room temperature under shielding the light for 1 hour. Then, the solvent was distilled off under reduced pressure. Benzene and diethyl ether were added to the residue, and the mixture was subjected to distillation under reduced pressure. This operation was repeated to obtain 203 mg of (2S,3R,4S)-4-(L-N$^{im}$-2,4-dinitrophenylhistidyl)amino-5-cyclohexyl-1-morpholino-2,3-pentanediol ditrifluoroacetate.

Rf value: 0.30(chloroform/methanol/aqueous ammonia=10/1/0.1)

EXAMPLE 23

(2S,3R,4S)-4-{L-N-[(2S)-3-[(2RS)-2,3-diacetoxypropyl]sulfonyl-2-(1-naphthylmethyl)propionyl]histidyl}amino-5-cyclohexyl-1-morpholino)-2,3-pentanediol (a) 85 mg of (2RS)-3-[(2RS)-2,3-diacetoxypropyl]sulfonyl-2-(1-naphthylmethyl)propionic acid and 203 mg of (2S,3R,4S)-4-(L-N$^{im}$-2,4-dinitrophenylhistidyl)amino-5-cyclohexyl-1-morpholino-2,3-pentanediol ditrifluoroacetate were subjected to coupling under shielding the light in the same manner as in Example 3(2a) to obtain 181 mg of (2S,3R,4S)-4-{L-N$^α$-[(2RS)-3[(2RS)-2,3-diacetoxypropyl]sulfonyl-2-( 1-naphthylmethyl)propionyl]-N$^{im}$-2,4-dinitrophenylhistidyl)amino-5-cyclohexyl-1-morpholino-2,3-pentanediol as yellow solid.

Rf value: 0.35(chloroform/methanol=10/1) Mass spectrum (FAB) m/z 1008(M+1)+1030(M+Na)+

(b) 170 mg of the compound obtained in Example 23(a) was dissolved in 2 ml of methanol, and 59 µl of 2-mercaptoethanol was added thereto. The mixture was stirred at room temperature for 4 hours. The reaction solution was diluted with 30 ml of ethyl acetate, and the ethyl acetate layer was washed with a 4% sodium hydrogencarbonate aqueous solution, with water and with a saturated sodium chloride aqueous solution and dried over anhydrous sodium sulfate. The solvent was distilled off under reduced pressure, and the residue was purified by silica gel column chromatography (chloroform/methanol=20/1) to obtain 68 mg of (2S,3R,4S)-4-(L-N$^α$-[(2S)-3-[(2RS)-2,3-diacetoxypropyl]sulfonyl-2-(1-naphthylmethyl)propionyl]histidyl}amino-5-cyclohexyl-1-morpholino-2,3-pentanediol.

Rf value: 0.13(chloroform/methanol=10/1) Mass spectrum (FAB) m/z 842(M+1)+ NMR (300 MHz, CDCl$_3$) δ ppm : 0.70~1.00(2H),1.00~1.34(4H),1.34~1.80(7H),1.92~2.11(6H),2.32~2.89(6H),2.89~3.58(10H),3.58~3.93(5-H),3.93~4.38(3H),4.50(1H,m), 5.32(0.5H,m),5.49(0.5H,m), 6.32(1H),6.89(1H),7.30~7.62(6H), 7.77(1H,d,J=8.1 Hz),7.87(1H,d,J=8.1 Hz),8.02(1H,d,J=8.7 Hz)

EXAMPLE 24

(2S,3R,4S)-4-amino-5-cyclohexyl-1-morpholino-2,3-pentanediol dihydrochloride (1) L-N-benzyloxycarbonylcyclohexylalaninal (a) 5.3 g of L-N-benzyloxycarbonylcyclohexylalanine was dissolved in 30 ml of dry methanol, and 1 ml of 10% hydrochloric acid-methanol was added thereto. The mixture was stirred at room temperature overnight. Methanol was distilled off from the reaction solution under reduced pressure, and the residue was dissolved in 300 ml of ethyl acetate. The solution was washed sequentially with water and with a saturated sodium chloride aqueous solution and dried over anhydrous magnesium sulfate. Then, the solvent was distilled off under reduced pressure, and the residue was purified by silica gel column chromatography (n-hexane/ethyl acetate=5/1) to obtain 4.4 g of L-N-benzyloxycarbonylcyclohexylalanine methyl ester as colorless oily substance.

Rf value: 0.35(n-hexane/ethyl acetate=5/1)

(b) 8.8 g of the compound obtained in Example 24(a) was dissolved in 90 ml of ethanol/THF (2/1), and 3.3 g of lithium chloride and 2.1 g of sodium borohydride were added thereto. The mixture was stirred at room temperature overnight. 1N hydrochloric acid was added to the reaction solution, and then the solvent was distilled off under reduced pressure. The residue was extracted with ethyl acetate. The ethyl acetate layer was washed with water and with a saturated sodium chloride aqueous solution and dried over anhydrous magnesium sulfate. Then, the solvent was distilled off under reduced pressure, and the residue was purified by silica gel column chromatography (n-hexane/ethyl acetate=2/1) to obtain 8.0 g of L-N-benzyloxycarbonylcyclohexylalaninol as colorless oily substance.

Rf value: 0.27 (n-hexane/ethyl acetate=2/1) (c) 6.8 g of the compound obtained in Example 24(1b) was dissolved in 50 ml of dry DMSO, 9.8 ml of triethylamine was added thereto, and 50 ml of a dry DMSO solution of 11.2 g of sulfur trioxide-pyridine complex was dropwise added thereto while keeping the temperature below 10° C. over a period of 30 minutes. The mixture was stirred for 10 minutes. The reaction solution was poured into ice water and extracted with ethyl acetate. The ethyl acetate layer was washed sequentially with 1N hydrochloric acid, with water, with a saturated sodium hydrogencarbonate aqueous solution and with a saturated sodium chloride aqueous solution and dried over anhydrous magnesium sulfate. Then, the solvent was distilled off under reduced pressure to obtain 6.5 g of L-N-benzyloxycarbonylcyclohexylalaninal as yellow oily substance.

(2) (4S,5R)-3-benzyloxycarbonyl-4-cyclohexylmethyl-5-ethenyl-2,2-dimethyloxazolidine (a) 3.4 g of the compound obtained in Example 24(1c) was dissolved in 25 ml of dry THF, and 36 ml of a 0.88M vinyl magnesium bromide THF solution was dropwise added thereto at −78° C. under an argon gas over a period of 40 minutes. After the dropwise addition, the reaction mixture solution was returned to room temperature and stirred at room temperature for 30 minutes. The reaction solution was poured into 250 ml of a saturated ammonium chloride aqueous solution, and extracted with ethyl acetate. The ethyl acetate layer was washed with a saturated sodium chloride aqueous solution and then dried over anhydrous magnesium sulfate. The solvent was distilled off under reduced pressure. The residue was purified by silica gel column chromatography (toluene/ethyl acetate=7/1) to obtain 1.9 g of (3RS,4S)-4-(benzyloxycarbonyl)amino-5-cyclohexyl-3-hydroxypentene as colorless oily substance.

Rf value: 0.18(n-hexane/ethyl acetate=4/1)

(b) 983 mg of the compound obtained in Example 24(2a) was dissolved in 5 ml of dichloromethane, and 4 ml of 2,2-dimethoxypropane and 30 mg of p-toluenesulfonic anhydride were added thereto. The mixture was stirred at room temperature overnight. 100 ml of ethyl acetate was added to the reaction mixture solution and washed with a saturated sodium hydrogencarbonate aqueous solution and with a saturated sodium chloride aqueous solution. Then, the organic layer was dried over anhydrous magnesium sulfate. The solvent was distilled off under reduced pressure, and the residue was purified by silica gel column chromatography (n-hexane/ethyl acetate=20/1) to obtain 967 mg of (4S,5RS)-3-benzyloxycarbonyl-4-cyclohexylmethyl-5-ethenyl-2,2-dimethyloxazolidine as colorless oily substance.

Rf value: 0.74(n-hexane/ethyl acetate=3/1)

(c) 3.76 g of the compound obtained in Example 24(2b) was dissolved in 25 ml of dioxane, and 20 ml of a dioxane solution of 132 mg of osmium tetraoxide was added thereto under shielding the light. The mixture was stirred at room temperature for 15 minutes. 6 ml of water was added thereto and then 30 ml of an aqueous solution of 4.5 g of sodium metaperiodate was added over a period of 30 minutes. The mixture was further stirred for 3 hours. Insolubles were removed by filtration, and then the filtrate was extracted with ethyl acetate. Ethyl acetate layer was washed with a 5% sodium sulfide aqueous solution and with a saturated sodium chloride aqueous solution and dried over anhydrous magnesium sulfate. Then, the solvent was distilled off under reduced pressure to obtain 3.82 g of (4S,5RS)-3-benzyloxycarbonyl-4-cyclohexylmethyl-5-formyl-2,2-dimethyloxazolidine as yellow oily substance.

Rf value: 0.42(n-hexane/ethyl acetate=3/1)

(d) 3.82 g of the compound obtained in Example 24(2c) was dissolved in 45 ml of methanol, 1.45 g of potassium carbonate was added thereto. The mixture was stirred at room temperature for 2 hours. 1.20 ml of acetic acid was added thereto at 0° C., and the mixture was stirred for 15 minutes. Then, 3.7 ml of a 1M phosphoric acid buffer solution (pH7) was added thereto, and the mixture was stirred at room temperature for 30 minutes. The solvent was distilled off under reduced pressure, and the residue was extracted with ethyl acetate. The ethyl acetate layer was washed with a saturated sodium chloride aqueous solution and dried over anhydrous magnesium sulfate. The solvent was distilled off under reduced pressure, and the residue was purified by silica gel column chromatography (n-hexane/ethyl acetate=2/1) to obtain 2.96 g of (4S,5R)-3-benzyloxycarbonyl-4-cyclohexylmethyl-5-formyl-2,2-dimethyloxazolidine as colorless oily substance.

(e) 6.3 g of methyltriphenylphosphonium bromide was suspended in dry THF, and 9 ml of a 2.3M n-butyl lithium n-hexane solution was dropwise added thereto at −78° C. under argon gas. The mixture was stirred for 1 hour until the temperature of the mixture was returned to room temperature. Then, a dry THF solution of 2.96 g of the compound obtained in Example 24(2d) was dropwise added at −78° C. over a period of 30 minutes. The reaction solution was returned to room temperature and stirred overnight. 100 ml of a sodium hydrogencarbonate aqueous solution was added to the reaction solution, and the mixture was stirred. 800 ml of ethyl acetate was added thereto, and the mixture was washed sequentially with a saturated sodium hydrogencarbonate aqueous solution, with water and with a saturated sodium chloride aqueous solution and dried over anhydrous magnesium sulfate. Then, the solvent was distilled off under reduced pressure, and the residue was purified by silica gel column chromatography (n-hexane/ethyl acetate=10/1) to obtain 2.39 g of (4S,5R)-3-benzyloxycarbonyl-4-cyclohexylmethyl-5-ethenyl-2,2-dimethyloxazolidine as colorless oily substance.

(3) (1S)-1-[(4S,5R)-3-benzyloxycarbonyl-4-cyclohexylmethyl-2,2-dimethyloxazolidin-5-yl]oxirane (a) 2.38 g of the compound Obtained in Example 24(2e) was dissolved in 36 ml of acetone/water (8/1), 1.6 g of n-methylmorpholine N-oxide and 8.3 ml of a tert-butanol solution (10 mg/ml) of osmium tetraoxide were added thereto. The mixture was stirred at room temperature overnight. 10 ml of a saturated sodium hydrogensulfite was added to the reaction solution. The mixture was stirred and diluted with ethyl acetate and washed with water and with a saturated sodium chloride aqueous solution and dried over anhydrous magnesium sulfate. Then, the solvent was distilled off under reduced pressure, and the residue was purified by silica gel column chromatography (n-hexane/ethyl acetate=½) to obtain 2.46 g of (4S,5R)-3-benzyloxycarbonyl-4-cyclohexylmethyl-5-[(1RS)-1,2-dihydroxyethyl]-2,2-dimethyloxazolidine as colorless oily substance.

(b) 10.2 g of the compound obtained in Example 24(3a) was dissolved in 100 ml of dry pyridine, and 6.2 g of p-toluenesulfonyl chloride was added thereto. The mixture was stirred at room temperature overnight. The reaction solution was poured into ice water and extracted with ethyl acetate. The ethyl acetate layer was washed with 1N hydrochloric acid, with water and with a saturated sodium chloride aqueous solution and dried over anhydrous magnesium sulfate. Then, the solvent was distilled off under reduced pressure, and the residue was subjected to silica gel column chromatography (n-hexane/ethyl acetate=4/1). The diastereomers were separated and purified to obtain 10.3 g of (4S,5R)-3-benzyloxycarbonyl-4-cyclohexylmethyl-2,2-dimethyl-5-[(1 S)-1-hydroxy-2-p-toluenesulfonyloxy]ethyloxazolidine as colorless oily substance.

Rf value: 0.32(n-hexane/ethyl acetate=3/1)

(c) 10.3 g of the compound obtained in Example 24(3b) was dissolved in 160 ml of methanol, and 5.2 g of potassium carbonate was added thereto. The mixture was stirred at room temperature for 2 hours. Insolubles were removed by filtration, and then the filtrate was concentrated under reduced pressure. Ethyl acetate was added to the residue, washed with 1N hydrochloric acid, with water, with a saturated sodium hydrogencarbonate aqueous solution and with a saturated sodium chloride aqueous solution and dried over anhydrous magnesium sulfate. The solvent was distilled off under reduced pressure, the residue was purified by silica gel column chromatography (n-hexane/ethyl acetate=5/1) to obtain 5.9 g of (1S)-1-[(4S,5R)-3-benzyloxycarbonyl-4-cyclohexylmethyl-2,2-dimethyloxazolidin-5-yl]oxirane as colorless oily substance.

Rf value: 0.57 (n-hexane/ethyl acetate=3/1)

(4) (2S,3R,4S)-4-amino-5-cyclohexyl-1-morpholino-2,3-pentanediol dihydrochloride (a) 80 mg of the compound obtained in Example 24(3c) was dissolved in 3.5 ml of methanol, and 22 μl of morpholine was added thereto. The mixture was refluxed under heating for 5 hours. The reaction mixture solution was distilled under reduced pressure to remove the solvent, and the residue was purified by silica gel column chromatography (n-hexane/ethyl acetate=1/1) to obtain 78 mg of (4S,5R)-3-benzyloxycarbonyl-4-cyclohexylmethyl-2,2-dimethyl-5-[(1S)-1-hydroxy-2-morpholinoethyl]oxazolidine as colorless oily substance.

Rf value: 0.32(n-hexane/ethyl acetate=1/1)

(b) 2.8 g of the compound obtained in Example 24(4a) was dissolved in 30 ml of methanol, and 2.9 g of p-toluenesulfonic acid monohydrate was added thereto. The mixture was stirred at room temperature overnight. Ethyl acetate was added to the reaction solution, washed with a saturated sodium hydrogencarbonate aqueous solution, with water and with a saturated sodium chloride aqueous solution and dried over anhydrous magnesium sulfate. Then, the solvent was distilled off under reduced pressure, and the residue was recrystallized from ethyl acetate to obtain 2.0 g of (2S,3R,4S)-4-benzyloxycarbonylamino-5-cyclohexylmethyl-1-morpholino-2,3-pentanediol as colorless needles.

Melting point: 124°–125° C. Rf value: 0.26(n-hexane/ethyl acetate=½)

(c) 598 mg of the compound obtained in Example 24(4b) was dissolved in 10 ml of methanol and subjected to hydrogenation at room temperature under atmospheric pressure by an addition of palladium black. The catalyst was removed by filtration, and then the solvent was distilled off under reduced pressure. The residue was dissolved in 10 ml of methanol and 2.8 ml of 1N hydrochloric acid was added thereto. The solvent was distilled off under reduced pressure to obtain 520 mg of the above-identified compound as white solid.

Rf value: 0.42 (chloroform/methanol/aqueous ammonia=10/2/0.2)

EXAMPLE 25

(2R,3R,4S)-4-{L-N-[(2S)-3-[(2RS)-2,3-diacetoxypropyl]sulfonyl-2-(1-naphthylmethylpropionyl]norleucyl}amino-1-isopropylthio-6-methyl-2,3-heptanediol (a) 5 g of L-N-tert-butoxycarbonylleucine monohydrate was dissolved in 50 ml of dichloromethane, and 2.1 g of 3,5-dimethylpyrazole was added thereto. 4.6 g of DCC was added thereto under cooling with ice, and the mixture was stirred at 0° C. for 2 hours and at room temperature overnight. The precipitates were removed by filtration, and then the solvent was distilled off under reduced pressure. The residue was recrystallized from methanol-water and washed with water to obtain 6.2 g of L-N-tert-butoxycarbonylleucine 3,5-dimethylpyrazolide as colorless crystals.

Rf value: 0.59 (n-hexane/ethyl acetate=3/1)

(b) 847 mg of lithium aluminum hydride was suspended in 18 ml of dry THF, and 72 ml of a dry THF solution of 6.2 g of the compound obtained in Example 25(a) was dropwise added thereto at −30° C. under argon gas over a period of 30 minutes. The reaction mixture was left to stand at the same temperature for 1 hour, and 4.5 ml of 5N hydrochloric acid was added thereto. Insolubles were removed by filtration, and the solvent was distilled off under reduced pressure. The residue was dissolved in diethyl ether. The organic layer was washed with 1N hydrochloric acid and with a saturated sodium chloride aqueous solution and then dried over anhydrous magnesium sulfate. The solvent was distilled off under reduced pressure to obtain 3.2 g of L-N-tert-butoxycarbonylleucinal as slightly yellow oily substance.

Rf value: 0.51 (n-hexane/ethyl acetate=3/1)

(c) 3.2 g of the compound obtained in Example 25(b) was dissolved in 30 ml of dry THF, and 50 ml of a 0.98M vinyl magnesium bromide THF solution was dropwise added thereto at −78° C. under argon gas over a period of 30 minutes. The reaction solution was returned to room temperature and further stirred overnight. Then, the reaction solution was poured into 20 ml of a saturated ammonium chloride aqueous solution and extracted with diethyl ether. The ether layer was washed with a saturated sodium chloride aqueous solution and then dried over anhydrous magnesium sulfate. The solvent was distilled off under reduced pressure. The residue was purified by silica gel column chromatography (n-hexane/ethyl acetate=5/1) to obtain 1.1 g of (3RS,4S)-4-(tert-butoxycarbonyl)amino-6-methylhepten-3-ol as colorless oily substance.

(d) The compound obtained in Example 25(c) was treated with p-toluenesulfonic acid in 2,2-dimethoxypropane to obtain (4S,5RS)-3-tert-butoxycarbonyl-2,2-dimethyl-4-isobutyloxazolidine. This compound was treated in the same manner as in Example 24(2) and (3) to obtain (1S)-1-[(4S,5R)-3-tert-butoxycarbonyl-2,2-dimethyl-4-isobutyloxazolidin-5-yl]oxirane.

Rf value: 0.56 (n-hexane/ethyl acetate=3/1)

(e) 510 mg of the compound obtained in Example 25(d) was dissolved in 8 ml of methanol, and 0.24 ml of triethylamine and 0.19 ml of isopropylmercaptane were added thereto. The mixture was refluxed under heating for 2 hours. The reaction solution was distilled under reduced pressure to remove the solvent, and the residue was purified by silica gel column chromatography (n-hexane/ethyl acetate=5/1) to obtain 510 mg of (4S,5R)3-tert-butoxycarbonyl-2,2-dimethyl-5-[(1 R)-1-hydroxy-2-isopropylthio]ethyl-4-isobutyloxazolidine as colorless oily substance.

Rf value: 0.68 (n-hexane/ethyl acetate=3/1)

(f) 85.1 mg of the compound obtained in Example 25(e) was dissolved in 2 ml of dioxane, and 2 ml of a 10% hydrochloric acid-methanol solution was added thereto. The mixture was stirred at room temperature for 3 hours. The reaction solution was distilled under reduced pressure to remove the solvent to obtain 61.4 mg of (2R,3R,4S)-4-amino-1-isopropylthio-6-methyl-2,3-heptanediol hydrochloride.

(g) 61.4 mg of the compound obtained in Example 25(f) and 95.0 mg of L-N-[(2S)-3-[(2RS)-2,3-diacetoxypropyl]sulfonyl-2-(1-naphthylmethyl)propionyl]norleucine were subjected to coupling by DPPA method described in Example 1(9). The purification was conducted by silica gel column chromatography (chloroform/methanol=50/1) to obtain 48.8 mg of the above-identified compound as white solid.

Rf value: 0.23 (chloroform/methanol=25/1) Mass spectrum (FAB) m/z 767(M+1)+ NMR (300 MHz, CDCl$_3$) δ ppm : 0.87(3H,t,J=7 Hz),0.91(3H,d,J=7 Hz),0.97(3H,d,J=7 Hz),1.12~1.90(15H,m),1.97(1.5H,s),2.06(4.5H,s), 2.36~3.50(10H,m),3.69~4.35(7H,m), 5.29~5.49(1H,m),6.06(0.5H,d, J=7 Hz),6.12(0.5H,d,J=7 Hz),6.23(0.5H,d,J=9 Hz),6.28(0.5 H,d,J=9 Hz),7.20~7.64(4H,m),7.79(1H,d,J=8 Hz),7.89(1H,d,J=8 Hz),8.00(1H,m)

EXAMPLE 26

(2R,3R,4S)-4-{L-N-[(2S)-3-[(2RS)-2,3-diacetoxypropyl]sulfonyl-2-(1-naphthylmethyl)propionyl]norleucyl}amino-1-isopropylsulfonyl-6-methyl-2,3-heptanediol (a) The compound obtained in Example 25(e) was subjected to sulfonation by hydrogen peroxide-sodium tungstate dihydrate in methanol, followed by removal of the protecting group in the same manner as in Example 25(f) to obtain (2R,3R,4S)-4-amino-1-isopropylsulfonyl-6-methyl-2,3-heptanediol monohydrochloride.

(b) 77.0 mg of the compound obtained in Example 26(a) and 97.9 mg of L-N-[(2S)-3-[(2RS)-2,3-diacetoxypropyl]sulfonyl-2-(1-naphthylmethyl)propionyl]norleucine were subjected to coupling by DPPA method described in Example 1(9), followed by purification by silica gel column chromatography (chloroform/methanol=50/1) to obtain 89.4 mg of the above-identified compound as white solid.

Rf value: 0.47(chloroform/methanol=10/1) Mass spectrum (FAB) m/z 799(M+1)+ NMR (300 MHz, CDCl$_3$) δ ppm : 0.76~0.95(9H,m),0.99~1.83(15H,m), 1.93(1.5H,s),2.01~2.03(4.5H,m), 3.10~3.50(11H,m),3.65~4.33(6H,m), 4.82(1H,d,J=4 Hz),5.25~5.45(1H,m), 6.08(0.5H,d,J=6 Hz),6.19(0.5H,d, J=6 Hz),6.68(0.5H,d,J=8 Hz),6.72(0.5H,d,J=8 Hz), 7.29~7.59(4H,m), 7.76(1H,d,J=8 Hz),7.85(1H,d,J=8 Hz),7.96(1H,m)

EXAMPLE 27

(2S,3R,4S)-4-{L-N-[(2RS)-3-acetoxy-2-methoxypropyl]thio-2-(1-naphthylmethyl)propionyl]norleucyl}amino-5-cyclohexyl-1-morpholino-2,3-pentanediol (1) L-N-[(2S)-3-[(2RS)-3-hydroxy-2-methoxypropyl]thio-2-(1-naphthylmethyl)propionyl]norleucine tert-butyl ester (a) 1.75 g of the compound obtained in Example 1(7b) was dissolved in 20 mg of dry pyridine, and 0.82 g of p-toluenesulfonyl chloride was added thereto at 0° C. The mixture was stirred at 10° C. overnight. The reaction solution was poured into ice water and extracted with ethyl acetate. The ethyl acetate layer was washed sequentially with 1N hydrochloric acid, with water and with a saturated sodium chloride aqueous solution and dried over anhydrous magnesium sulfate. The solvent was distilled off under reduced pressure. The residue was purified by silica gel column chromatography (n-hexane/ethyl acetate=½) to obtain 1.38 g of L-N[(2S)-3-[(2RS)-3-p-toluenesulfonyloxy-2-hydroxypropyl]thio-2-(1-naphthylmethyl)propionyl]norleucine tert-butyl ester as colorless oily substance.

Rf value: 0.23(n-hexane/ethyl acetate=2/1)

(b) 1.38 g of the compound obtained in Example 27(1) was dissolved in 15 ml of methanol, and 0.62 g of potassium carbonate was added thereto. The mixture was stirred at room temperature for 2 hours. Inorganic substances were removed by filtration, and the filtrate was concentrated under reduced pressure. Ethyl acetate was added to the residue, washed sequentially with 1N hydrochloric acid, with water and with a saturated sodium chloride aqueous solution and dried over anhydrous magnesium sulfate. The solvent was distilled off under reduced pressure. The residue was purified by silica gel column chromatography (n-hexane/ethyl acetate=5/1) to obtain 0.42 g of L-N-[(2S)-3-[(2RS)-2,3-epoxypropyl]sulfonyl-2-(1-naphthylmethyl)propionyl]norleucine tert-butyl ester as colorless oily substance.

Rf value: 0.48 (n-hexane/ethyl acetate=2/1)

(c) 192.2 mg of the compound obtained in Example 27(1b) was dissolved in 8 ml of methanol, and two drops of concentrated sulfuric acid was added thereto. The mixture was stirred at room temperature for 1 hour. The solvent was evaporated from the reaction solution, and the residue was diluted with ethyl acetate, washed sequentially with a saturated sodium hydrogencarbonate aqueous solution, with water and with a saturated sodium chloride aqueous solution and dried over anhydrous magnesium sulfate. The solvent was distilled off under reduced pressure. The residue was purified by silica gel column chromatography (n-hexane/ethyl acetate=1/1) to obtain 183.1 mg of the above-identified compound as colorless oily substance.

Rf value: 0.09, 0.15 (n-hexane/ethyl acetate=2/1)

(2)L-N-{(2S)-3-[(2RS)-3-acetoxy-2-methoxypropyl]thio-2-(1-naphthylmethyl)propionyl}norleucine tert-butyl ester 104.4 mg of the compound obtained in Example 27(1c) was dissolved in 1 ml of dry pyridine, and 0.5 ml of acetic anhydride was added thereto. The mixture was treated in the same manner as in Example 1(7c) to obtain 112.3 mg of the above-identified compound as colorless oily substance.

Rf value: 0.45, 0.48 (n-hexane/ethyl acetate=2/1)

(3) (2S,3R,4S)-4-{L-N-[(2S)-3-[(2RS)-3-acetoxy-2-methoxypropyl]thio-2-(1-naphthylmethyl)propionyl]norleucyl}amino-5-cyclohexyl-1-morpholino-2,3-pentanediol 111.3 mg of the compound obtained in Example 27(2) was treated in the same manner as in Example 1(8b)–(9)

to obtain 100.1 mg of the above-identified compound as white powder.

Rf value: 0.30(chloroform/methanol=20/1) Mass spectrum (FAB) m/z 758(M+1)+ NMR (300 MHz, CDCl$_3$) δ ppm : 0.83~1.85(23H,m),1.99~2.06(3H,m), 2.43~3.01(11H,m),3.08~3.54(10H,m), 3.58~3.90(5H,m),4.05~4.38(4H,m), 4.62(1H,brs),5.98~6.33(2H,m), 7.34~7.60(4H,m),7.77(1H,d,J=8 Hz), 7.89(1H,d,J=8 Hz),7.99~8.09(1H,m)

EXAMPLE 28

(2S,3R,4S)-4-{L-N-[(2S)-3-[(2RS)-2-acetoxy-3-methoxypropyl]sulfonyl-2-(1-naphthylmethyl)propionyl]norleucyl}amino-5-cyclohexyl-1-morpholino-2,3-pentanediol (1) L-N-[(2S)-3-[(2RS)-2-acetoxy-3-methoxypropyl]sulfonyl-2-(1-naphthylmethyl)propionyl]norleucine tert-butyl ester (a) 210.5 mg of the compound obtained in Example 27(1b) was dissolved in 2 ml of methanol, and 28.8 mg of sodium methoxide was added thereto. The mixture was stirred at room temperature for 1 day and then refluxed under heating for 2 hours. Ethyl acetate was added to the reaction solution, washed with water and with a saturated sodium chloride aqueous solution and dried over anhydrous magnesium sulfate. The solvent was distilled off under reduced pressure. The residue was purified by silica gel column chromatography to obtain 52.1 mg of L-N-[(2S)-3-[(2RS)-2-hydroxy-3-methoxypropyl]thio-2-(1-naphthylmethyl)propionyl]norleucine tert-butyl ester as colorless oily substance.

Rf value: 0.25(n-hexane/ethyl acetate=2/1)

(b) 49.2 mg of the compound obtained in Example 28(1) was dissolved in 0.5 ml of dry pyridine, and 0.25 ml of acetic anhydride was added thereto. The mixture was treated in the same manner as in Example 1(7c) to obtain 53.3 mg of the above-identified compound as colorless oily substance.

Rf value: 0.62 (n-hexane/ethyl acetate=1/1) 2S,3R,4S)-4-{L-N-[(2S)-3-[(2 RS )-2-acetoxy-3-methoxypropyl]sulfonyl-2(1-naphthylmethyl)propionyl]norleucyl}amino-5-cyclohexyl-1-morpholino-2,3-pentanediol The compound obtained in Example 28(1b) was treated in the same manner as in Example 1(8)–(9) to obtain 50.8 mg of the above-identified compound as white powder.

Rf value: 0.33(chloroform/methanol=20/1) Mass spectrum (FAB) m/z 790(M+1)+ NMR (300 MHz, CDCl$_3$) δ ppm : 0.81~1.79(22H,m),1.97(1.5H,s), 2.09(1.5H,s),2.44~2.82(6H,m), 3.09~3.53(14H,m),3.60~3.80(5H,m), 4.17~4.32(2H,m),4.59(1H,brs), 5.21~5.39(1H,m),5.90~6.01(2H,m), 7.33~7.64(4H,m),7.79(1H,d,J=8 Hz), 7.89(1H,d,J=8 Hz),8.01(1H,m)

EXAMPLE 29

(2S,3R,4S)-4-{L-N-[(2S)-3-[(2RS)-3-acetoxy-2-methoxypropyl]sulfonyl-2-(1-naphthylmethyl)propionyl]norleucyl}amino-5-cyclohexyl-1-morpholino-2,3-pentanediol 112.6 mg of the compound obtained in Example 27(2) was treated in the same manner as in Example 1(8)–(9) to obtain 103.9 mg of the above-identified compound as white powder.

Rf value: 0.24 (chloroform/methanol=20/1) Mass spectrum (FAB) m/z 790(M+1)+ NMR (300 MHz, CDCl$_3$) δ ppm : 0.79~0.92(3H,m),1.07~1.82(19H,m), 2.02(1.5H,s),2.08(1.5H,s)2.35~2.99(6H,m),3.06~3.75(-17H,m),3.75~4.71(4H,m),5.81~6.05(2H,m),7.32~7.49(2H,m),7.49~7.63(2H,m),7.80(1H,d,J=7.9 Hz),7.90(1H,d,J=7.9 Hz),7.99~8.08(1H,m)

EXAMPLE 30

(2S,3R,4S)-4-{L-N$^\alpha$-[(2S)-3-(2-acetoxyethyl)sulfonyl-1-naphthylmethyl)propionyl]histidyl}amino-5-cyclohexyl-1-morpholino-2,3-pentanediol (a) 800 mg of the compound obtained in Example 3(1d) was acetylated in the same manner as in Example 3(2b), and 423 mg of the acetyl compound was subjected to sulfonation in the same manner as in Example 1(8) to obtain 441 mg of (2RS)-3-(2-acetoxyethyl)sulfonyl-2-(1-naphthylmethyl)propionic acid.

Rf value: 0.31(chloroform/methanol/acetic acid=10/0.5/0.1)

(b) 62.2 mg of the compound obtained in Example 30(a) and 124 mg of the compound obtained in Example 22 were subjected to coupling under shielding the light in the same manner as in Example 3(2a) to obtain 138 mg of (2S,3R,4S)-4-{L-N$^\alpha$-[(2RS)-3-(2-acetoxyethyl)-sulfonyl-2-(1-naphthylmethyl)propionyl]-N$^{im}$-2,4-dinitrophenylhistidyl}amino-5-cyclohexyl-1-morpholino-2,3-pentanediol as yellow solid.

Rf value: 0.41 (chloroform/methanol=10/1)

(c) 135 mg of the compound obtained in Example 30(b) was subjected to removal of the protecting group in the same manner as in Example 23(b) to obtain 39.6 mg of the above-identified compound.

Rf value: 0.11 (chloroform/methanol=10/1) Mass spectrum (FAB) m/z 770(M+1)+ NMR (300 MHz, CDCl$_3$) δ ppm : 0.73~1.83(13H),1.98(3H,s),2.39~2.90(5H),2.95~3.60(-11H),3.60~3.82(5H),4.20(1H,br),4.38(2H,m), 4.52(1H,m),6.36(1H,br),6.90(1H,s), 7.30~7.62(5H),7.77(1H,d,J=8.1 Hz),7.87(1H,d,J=7.8 Hz),8.02(1H,d, J=8.1 Hz)

EXAMPLE 31

(2S,3R,4S)-4-(L-N$^\alpha$-[(2S)-3-(2-acetoxyethyl)thio-2-(1-naphthylmethyl)propionyl]histidyl}amino-5-cyclohexyl-1-morpholino-2,3-pentanediol (a) 73.1 mg of the compound obtained in Example 30(a) and 234 mg of the compound obtained in Example 22 were subjected to coupling under shielding the light in the same manner as in Example 3(2a) to obtain 169 mg of (2S,3R,4S)-4-(L-N$^\alpha$-[(2SR)-3-{2-acetoxyethyl)thio-2-naphthylmethyl)propionyl]-N$^{im}$-2,4-dinitrophenylhistidyl}amino-5-cyclohexyl-1-morpholino-2,3-pentanediol as yellow solid.

Rf value: 0.39, 0.45 (chloroform/methanol=10/1)

(b) 166 mg of the compound obtained in Example 31(a) was reacted in the same manner as in Example 23(b) to obtain 44.4 mg of the above-identified compound.

Rf value: 0.24(chloroform/methanol=10/1) Mass spectrum (FAB) m/z 738(M+1)+ NMR (300 MHz, CDCl$_3$) δ : 0.71~1.80(1H),1.98(3H,s),2.38~3.18 (13H),3.27~3.78(9H),4.06~4.26 (3H),4.55(1H,m),6.48(1H,d,$J$=9.3 Hz),6.86(1H,s),7.32~7.63(5H), 7.75(1H,d,J=7.5 Hz),7.87(1H,d,J=7.5 Hz),8.30(1H,d,J=8.1 Hz)

EXAMPLE 32

L-N-[(2S)-3-mercapto-2-(1-naphthylmethyl)propionyl]-norleucine tert-butyl ester (a) 500 mg of the compound obtained in Example 1(7 a) was dissolved in 5 ml of acetone, and 217 mg of potassium xanthogenate was added thereto. The mixture was stirred at room temperature overnight. 60 ml of ethyl acetate was added to the reaction solution, and the organic layer was washed with water and with a saturated sodium chloride aqueous solution. Then, the solvent was distilled off under reduced pressure, and the residue was purified by silica gel column chromatography (n-hexane/ethyl acetate=6/1) to obtain 418 mg of L-N-[(2S)-3-ethoxythiocarbonyl)thio-2-(1-naphthylmethyl)propionyl]norleucine tert-butyl ester as colorless solid.

Rf value: 0.53(n-hexane/ethyl acetate=6/1)

(b) 163 mg of the compound obtained in Example 32(a) was dissolved in 0.6 ml of methanol, and 29.2 mg of ethylene diamine was added thereto. The mixture was stirred at room temperature for 45 minutes. 30 mg of ethyl acetate was added to the reaction solution, and the organic layer was washed with a 5% potassium hydrogensulfate aqueous solution and with a saturated sodium chloride aqueous solution. Then, the solvent was distilled off. The residue was purified in the same manner as in Example 32(a) to obtain 115 mg of the above-identified compound as colorless solid.

Rf value: 0.46 (n-hexane/ethyl acetate=6/1)

EXAMPLE 33

(2S,3R,4S)-4-{L-N-[(2S)-3-(3-acetoxycylopentyl)sulfonyl-2-(1-naphthylmethyl)propionyl]norleucyl}amino-5-cyclohexyl-1-morpholino-2,3-pentanediol (a) 115 mg of the compound obtained in Example 32 was dissolved in 0.5 ml of dry DMF, and 34.2 mg of 2-cyclopentenone and 6.2 mg of potassium tert-butoxide were added thereto. The mixture was stirred at room temperature for 20 minutes. 20 ml of ethyl acetate was added to the reaction solution, and the organic layer was washed with water and with a saturated sodium chloride aqueous solution. Then, the solvent was distilled off, and the residue was purified by silica gel column chromatography (n-hexane/ethyl acetate=4/1) to obtain 102 mg of L-N-[(2S)-3-(3-oxocyclopentyl)thio-2-(1-naphthylmethyl)propionyl]norleucine tert-butyl ester as colorless oily substance.

Rf value: 0.63(n-hexane/ethyl acetate=1/1)

(b) 102 mg of the compound obtained in Example 33(a) was dissolved in 1 ml of ethanol, and 8.2 mg of sodium borohydride was added thereto. The mixture was stirred at room temperature for 35 minutes. The work up was conducted in the same manner as in Example 33(a), and the solvent was evaporated to obtain 101 mg of L-N-[(2S)-3-(3-hydroxycyclopentyl)thio-2-(1-naphthylmethyl)propionyl]norleucine tert-butyl ester as colorless oily substance.

Rf value: 0.38(n-hexane/ethyl acetate=1/1)

(c) 101 mg of the compound obtained in Example 33(b) was acetylated in the same manner as in Example 3(2b) to obtain 98 mg of L-N-[(2S)-3-(3-acetoxycyclopentyl)thio-2-(1-naphthylmethyl)propionyl]norleucine tert-butyl ester.

Rf value: 0.28(n-hexane/ethyl acetate=3/1)

(d) 98 mg of the compound obtained in Example 33(c) was subjected to sulfonation in the same manner as in Example 1(8) to obtain 19 mg of the isomer having a high Rf value of L-N-[(2S)-3-(3-acetoxycyclopentyl)-sulfonyl-2-(1-naphthylmethyl)propionyl]norleucine tert-butyl ester, and 63 mg of the isomer having a low Rf value.

Rf value: 0.4.1, 0.49 (n-hexane/ethyl acetate=1/1)

(e) 18 mg of the isomer having a high Rf value of the compound obtained in Example 33(d) was treated in the same manner as in Example 1(8b)–(9) to obtain 19 mg of isomer A of the above-identified compound as colorless solid.

Rf value: 0.39(chloroform/methanol=15/1) Mass spectrum (FAB) m/z 786(M+1)+ NMR (300 MHz, CDCl$_3$) δ ppm : 2.00(3H,s),2.49(2H),2.56~2.81(4H),3.02(1H,m),3.25~3.78(12H), 4.23(2H),5.21(1H,brs),5.91~6.09(2H),7.32~7.50(2H),7.50~7.67(2H), 7.80(1H,d,J=8.2 Hz),7.90(1H,d,J=8.2 Hz),8.00(1H,d,J=8.2 Hz)

Further, 57 mg of isomer B of the above-identified compound was obtained as colorless solid from 63 mg of the isomer having a low Rf value of the compound obtained in Example 33(d).

Rf value: 0.40 (chloroform/methanol=15/1) Mass spectrum (FAB) m/z 786(M+1)+ NMR (300 MHz, CDCl$_3$) δ ppm : 2.03(3H,s),2.49(2H),2.56~2.84(4H ),3.01(1H,dd,J=2.4,13.8 Hz), 3.12(2H),3.25~3.78(13H),4.22(2H), 5.02(1H,m),5.97(1H,d,J=8.4 Hz), 6.06(1H),7.31~7.50(2H),7.50~7.67(2H),7.80(1H,d,J=8.1 Hz),7.90(1H, d,J=8.1 Hz),8.00(1H,d,J=8.7 Hz)

EXAMPLE 34

(2S,3R,4S)-4-{L-N-[(2S)-3-(3-acetoxycyclopentyl)thio-2-(1-naphthylmethyl)propionyl]norleucyl}amino-5-cyclohexyl-1-morpholino-2,3-pentanediol 68 mg of the compound obtained in Example 33(c) was treated in the same manner as in-Example 1(8b)–(9) to obtain 61 mg of the above-identified compound as colorless solid.

Rf value: 0.60 (ethyl acetate/methanol=10/1) Mass spectrum (FAB) m/z 754(M+1)+ NMR (300 MHz, CDCl$_3$) δ ppm : 2.30~2.65(3H),2.65~3.13(7H),3.37~3.63(4H),3.77(4-H),4.33(2H), 5.12(0.75H,m),5.25(0.25H,m),5.80(1H), 6.10(1H),7.38~7.54(2H),7.54~7.70(2H),7.84(1H,d,J=-7.5 Hz),7.96(1H, d,J=7.5 Hz),8.10(1H,d,d=7.8 Hz)

EXAMPLE 35

(2S,3R,4S)-4-{L-N-[(2S)-3-(2-acetoxycyclopentyl)sulfonyl-2-(1-naphthylmethyl)propionyl]norleucyl}amino-5-cyclohexyl-1-morpholino-2,3-pentanediol (a) 179 mg of the compound obtained in Example 32 was dissolved in 4.3 ml of a 0.1N potassium hydroxide methanol/water (10/1) solution, and 146 mg of cyclopentene oxide was added thereto. The mixture was stirred at room temperature overnight. The reaction solution was concentrated under reduced pressure, and the residue was dissolved in 40 ml of ethyl acetate and washed with water and with a saturated sodium chloride aqueous solution. Then, the solvent was distilled off under reduced pressure. The residue was purified by silica gel column chromatography (n-hexane/ethyl acetate =4/1) to obtain 195 mg of L-N-[(2S)-3-(2-hydroxycyclopentyl)thio-2-(1-naphthylmethyl)propionyl]norleucine tert-butyl ester as colorless oily substance.

Rf value: 0.28 (n-hexane/ethyl acetate=2/1) (b) 140 mg of the compound obtained in Example 35(a) was acetylated in the same manner as in Example 3(2b) to obtain 145 mg of L-N-[(2S)-3-(2-acetoxycyclopentyl)thio-2-(1-naphthylmethyl)propionyl]norleucine tert-butyl ester as colorless oily substance.

Rf value: 0.71 (n-hexane/ethyl acetate=2/1)

(c) 76 mg of the compound obtained in Example 35(b) was subjected to sulfonation in the same manner as in Example 1(8) to obtain 70 mg of L-N,[(2S)-3-(2-acetoxycyclopentyl)sulfonyl-2-(1-naphthylmethyl)propionyl]-norleucine tert-butyl ester as colorless solid.

Rf value: 0.62 (n-hexane/ethyl acetate=1/1)

(d) 69 mg of the compound obtained in Example 35(c) was treated in the same manner as in Example 1(8b)–(9) to obtain 68 mg of the above-identified compound as colorless solid.

Rf value: 0.59 (ethyl acetate/methanol=10/1) Mass spectrum (FAB) m/z-786(M+1)+ NMR (300 MHz, CDCl$_3$) δ ppm : 2.04(1.5H,s),2.05(1.5H,s),2.40~2.83(5H),3.14~3.52(8-H),3.60~3.96 (5H),4.11~4.32(2H),5.38(1H),5.78(0.5H,d,J=6 Hz),5.88(0.5H,d,J=6 Hz),5.95(0.5H,d,J=9.3 Hz),6.02(0.5H,d,J=9.3 Hz),7.36~7.49(2H), 7.49~7.66(2H),7.79(1H,d,J=8.4 Hz), 7.90(1H,d,J=7.8 Hz),8.40(1H)

EXAMPLE 36

(2S,3R,4S)-4-{L-N-[(2S)-3-(2,3-diacetoxycyclopentyl)-sulfonyl-2-(1-naphthylmethyl)propionyl]norleucyl-}amino-5-cyclohexyl-1-morpholino-2,3-pentanediol (a) 2.97 g of 2-cyclopentenone was dissolved in dry THF, and the solution was stirred at 0° C. under an argon gas. 74.8 ml of a 0.5M 9-borabicyclo[3.3.1]nonane THF solution was dropwise added thereto, and the mixture was stirred at the same temperature for 2 hours and at room temperature for 1 hour. 0.18 ml of methanol was added to the reaction solution, and the solvent was distilled off under reduced pressure. The residue was dissolved in 20 ml of dry n-pentane, 2.28 ml of ethanolamine was added thereto, and precipitates were removed by centrifugation. n-pentane was evaporated and the residue was subjected to distillation under reduced pressure to obtain 1.01 g of 2-cyclopentenol as colorless oily substance.

Rf value: 0.26 (n-hexane/ethyl acetate=3/1) Boiling point: 79°–81° C. (61 mmHg)

(b) 2.20 g of 70% metachloroperbenzoic acid was dissolved in 18 ml of dry diethyl ether, 500 mg of 2-cyclopentenol was dropwise added thereto at 0° C. under stirring. The reaction solution was left to stand at 5° C. for 9 days. Then, 2.38 g of calcium hydroxide was added thereto, and the mixture was stirred at room temperature for 1 hour. Precipitates were removed by filtration and washed with dry diethyl ether. The filtrate and the washing solution were put together and concentrated. The residue was subjected to distillation under reduced pressure to obtain 281 mg of 2,3-epoxycyclopentenol as colorless oily substance.

Rf value: 0.24(n-hexane/ethyl acetate=1/1) Boiling point: 90°–95° C. (25 mmHg) (c) 99 mg of the compound obtained in Example 32 and 123 μl of the compound obtained in Example 36(b) were treated in the same manner as in Example 35(a) to obtain 85.2 mg of the mixture of L-N-[(2S)-3-(2,3-dihydroxycyclopentyl)thio-2-(1-naphthylmethyl)propionyl]norleucine tert-butyl ester and L-N-[(2S)-3-(2,5-dihydroxycyclopentyl)thio-2-(1-naphthylmethyl)propionyl]norleucine tert-butyl ester as colorless oily substance.

Rf value: 0.22, 0.26 (n-hexane/ethyl acetate=1/1)

(d) 85 mg of the mixture obtained in Example 36(c) was acetylated in the same manner as in Example 3(2b), followed by sulfonation in the same manner as in Example 1(8a) to obtain 49 mg of L-N-[(2S)-3-(2,3-diacetoxycyclopentyl)sulfonyl-2-(1-naphthylmethyl)propionyl]-norleucine tert-butyl ester and 22 mg of L-N-[(2S)-3-(2,5-diacetoxycyclopentyl)sulfonyl-2-(1-naphthylmethyl)propionyl]norleucine tert-butyl ester as colorless oily substance.

Rf value: 2,3-diacetoxy compound 0.44 (n-hexane/ethyl acetate=1/1) 2,5-diacetoxy compound 0.52(n-hexane/ethyl acetate=1/1)

(e) 49 mg of the 2,3-diacetoxy compound obtained in Example 36(d) was treated in the same manner as in Example 1(8b)–(9) to obtain 52 mg of the above-identified compound as colorless solid.

Rf value: 0.63 (chloroform/methanol=10/1) Mass spectrum (FAB) m/z 844(M+1)+

EXAMPLE 37

(2S,3R,4S)-4-{L-N-[(2S)-3-(2,5-diacetoxycyclopentyl)-sulfonyl-2-(1-naphthylmethyl)propionyl]norleucyl}amino-5-cyclohexyl-1-morpholino-2,3-pentanediol 22 mg of the 2,5-diacetoxy compound obtained in Example 36(d) was treated in the same manner as in Example 1(8b)–(9) to obtain 23 mg of the above-identified compound as colorless solid.

Rf value: 0.64(chloroform/methanol=10/1) Mass spectrum (FAB) m/z 844(M+1)+

EXAMPLE 38

(2S,3R,4S)-4-{L-N-[(2S)-3-[3-O-acetyl-5-deoxy-1,2-O-isopropylidene-α-D-ribofuranos-5-yl]sulfonyl-2-benzylpropionyl]norleucyl}amino-5-cyclohexyl-1-morpholino-2,3-pentanediol (a) 0.5 ml of dry DMF was added to 23 mg of sodium hydride, and 1 ml of a dry DMF solution of 279 mg of 3-O-benzyl-5-deoxy-1,2-O-isopropylidene-5-mercapto-α-D-ribofuranose was further added thereto under an argon stream. The mixture was stirred. 40 minutes later, 1 ml of a DMF solution of 158 mg of L-N-[(2R)-2-benzyl-3-(p-toluenesulfonyloxy)propionyl]norleucine tert-butyl ester was added thereto, and the mixture was stirred for 30 minutes. The reaction solution was diluted with ethyl acetate, washed with water and then with a saturated sodium chloride aqueous solution. The organic layer was dried over anhydrous sodium sulfate and then concentrated under reduced pressure. The residue was purified by silica gel column chromatography (n-hexane/ethyl acetate=3/1) to obtain 108 mg of L-N-[(2S)-3-[3-O-benzyl-5-deoxy-1,2-O-isopropylidene-α-D-ribofuranos-5-yl]thio-2-benzylpropionyl]norleucine tert-butyl ester as syrup.

NMR (300 MHz, CDCl$_3$) δ ppm : 0.87(3H,t,J=7.0 Hz),1.41(6H,s), 1.57(9H,s),2.51~2.72(3H,m),2.78~2.97(4H,m),3.67(1-H,dd,J=3.9,8.7 Hz),4.22(1H,ddd,J=2.8,5.6,8.7 Hz), 4.37(1H,m),4.54(1H,t,J=4.2 Hz), 4.55(1H,d,J=11.7 Hz),4.76(1H,d,J=12.0 Hz),5.69(1H,d,J=3.9 Hz),6.05(1H,d,J=8.1 Hz),7.1~7.4(10H,m)

(b) 108 mg of the compound obtained in Example 38(a) was treated in the same manner as in Example 1(8a) to obtain 110 mg of a sulfonyl compound.

Then, the same treatment was conducted in the same manner as in Example 15(b), followed by subjecting to removal of a benzyl group. Then, 101 mg of the solid thereby obtained was dissolved in 2 ml of dry pyridine. 0.2 ml of acetic anhydride was added thereto, followed by treatment in the same manner as in Example 1(7c) to obtain 101 mg of L-N-[(2S)-3-[3-O-acetyl-5-deoxy-1,2-O-isopropylidene-α-D-ribofuranos-5-yl]sulfonyl-2-benzylpropionyl]norleucine tert-butyl ester as a jelly-like substance.

NMR (300 MHz, CDCl₃) δ ppm : 2.14(3H,s),2.89~3.26(6H,m),3.69(1H,dd,J=7.5,12.3 Hz),4.35(1H,m), 4.52(1H,dt,J=2.9,8.0 Hz),4.60(1H, dd,J =4.5,9.0 Hz),4.76(1H,t,J=3.9 Hz),5.69(1H,d,J=4.2 Hz),6.09(1H,d, J=7.8 Hz),7.16~7.33(5H,m)

(c) 101 mg of the compound obtained in Example 38(b) was treated in the same manner as in Example 1(8b)–(9) to obtain 86 mg of the above-identified compound as white solid.

Rf value: 0.27 (chloroform/methanol=20/1) NMR (300 MHz, CDCl₃) δ ppm : 4.23(2H,m),4.48~4.82(3H,m),4.77(1H,t,J=4.1 Hz),5.68(1H,d,J=3.6 Hz),5.97(1H,d,J=6.0 Hz),6.05(1H,d, J=9.3 Hz),7.2~7.4(5H,m)

EXAMPLE 39

(2S,3R,4S)-4-{L-N-[(2S)-3-[(2R(or S))-3-acetoxy-2-methoxypropyl]sulfonyl-2-(1-naphthylmethyl)propionyl]norleucyl}amino-5-cyclohexyl-1-morpholino-2,3-pentanediol (a) 90.5 mg of the compound obtained in Example 27(1) was treated in the same manner as in Example 1(8a), followed by purification by silica gel column chromatography to obtain 48.5 mg of the isomer having a high Rf value and 40.0 mg of the isomer having a low Rf value as colorless oily substance, respectively.

Rf value: Isomer having a high Rf value 0.22 (n-hexane/ethyl acetate=1/1) Isomer having a low Rf value 0.10 (n-hexane/ethyl acetate=1/1)

(b) 48.5 mg of the isomer having a high Rf value obtained in Example 39(a) was acetylated in the same manner as in Example 1(7c), followed by subjecting to the treatment in the same manner as in Example 1(8b)–(9) to obtain 50.1 mg of the above-identified compound as white powder.

Rf value: 0.24(chloroform/methanol=20/1) Mass spectrum (FAB) m/z 790(M+1)+

EXAMPLE 40

(2S,3R,4S)-4-{L-N-[(2S)-3[(2S(or R))-3-acetoxy-2-methoxypropyl]sulfonyl-2,(1-naphthylmethyl)propionyl]norleucyl}amino-5-cyclohexyl-1-morpholino-2,3-pentanediol 40.0 mg of the isomer having a low Rf value obtained in Example 39(a) was acetylated in the same manner as in Example 1(7c), followed by subjecting to the treatment in the same manner as in Example 1(8b)–(9) to obtain 42.3 mg of the above-identified compound as white powder.

Rf value: 0.24 (chloroform/methanol=20/1) Mass spectrum (FAB) m/z 790(M+1)+

EXAMPLE 41

(2S,3R,4S)-4-{L-N-[(2S)-3-(3-acetoxy-2-methoxyiminopropyl)sulfonyl-2-(1-naphthylmethyl)propionyl]norleucyl}amino-5-cyclohexyl-1-morpholino-2,3-pentanediol (1) L-N-[(2S)-3-(3-acetoxy-2-oxopropyl)thio-2-(1-naphthylmethyl)propionyl]norleucine benzyl ester (a) The same treatment was conducted in the same manner as in Example 1(6)–(7b) except that L-norleucine benzyl ester was used instead of L-norleucine tert-butyl ester to obtain L-N-[(2S)-3-(2,3-dihydroxypropyl)thio-2-(1-naphthylmethyl)propionyl]norleucine benzyl ester.

Rf value: 0.29 (n-hexane/ethyl acetate=1/2)

(b) The compound obtained in Example 41(1) was treated in the same manner as in Example 9 to obtain L-N-[(2S)-3-(3-acetoxy-2-hydroxypropyl)thio-2-(1-naphthylmethyl)propionyl]norleucine benzyl ester.

Rf value: 0.32 (n-hexane/ethyl acetate=1/1)

(c) 329 mg of the compound obtained in Example 41(1b) was dissolved in 1.5 ml of dry DMSO, and 0.25 ml of triethylamine was added thereto. The mixture was stirred at room temperature, and then 1.0 ml of dry DMSO solution of 285 mg of sulfur trioxide-pyridine complex was dropwise added thereto. The mixture was stirred at room temperature overnight. The reaction solution was poured into ice water and extracted With ethyl acetate. The organic layer was washed sequentially with 1N hydrochloric acid, with water, with a saturated sodium hydrogencarbonate aqueous solution and with a saturated sodium chloride aqueous solution and dried over anhydrous magnesium sulfate. The solvent was distilled off under reduced pressure, and the residue was purified by silica gel column chromatography to obtain 250.7 mg of the above-identified compound as colorless solid.

Rf value: 0.32 (n-hexane/ethyl acetate=2/1)

(2) L-N-[(2S)-3-acetoxy-2-methoxyiminopropyl)sulfonyl-2-(1-napthylmethyl)propionyl]norleucine benzyl ester (a) 89.1 mg of the compound obtained in Example 41(1c) was dissolved in 1 ml of methanol, and 316 μl of a 1N potassium hydroxide methanol/water (9/1) solution of 26 mg of O-methylhydroxylamine hydrochloride was added thereto. The mixture was stirred at room temperature overnight. 1N hydrochloric acid was added to the reaction solution and extracted with ethyl acetate. The organic layer was washed with 1N hydrochloric acid and with a saturated sodium chloride aqueous solution and dried over anhydrous magnesium sulfate. Then, the solvent was distilled off under reduced pressure, and the residue was purified by silica gel column chromatography to obtain 66.9 mg of L-N-[(2S)-3-(3-acetoxy-2-methoxyiminopropyl)thio-2-(1-naphthylmethyl)propionyl]norleucine benzyl ester as colorless oily substance.

Rf value: 0.76 (n-hexane/ethyl acetate=1/1)

(b) The compound obtained in Example 41(2a) was treated in the same manner as in Example 1(8a) to obtain the above-identified compound.

Rf value: 0.26 (n-hexane/ethyl acetate=2/1)

(3) (2S,3R,4S)-4-{L-N-[(2S)-3-acetoxy-2-methoxyiminopropyl)sulfonyl-2-(1-naphthylmethyl)propionyl]norleucyl}amino-5-cyclohexyl-1-morpholino-2,3-pentanediol (a) 42.5 mg of the compound obtained in Example 41(2b) was dissolved in 0.5 ml of dioxane, followed by hydrogenation at room temperature under atmospheric pressure by palladium black. The catalyst was removed by filtration, and then the solvent was distilled off under reduced pressure to obtain 31.5 mg of L-N-[(2S)-3-(3-acetoxy-2-methoxyiminopropyl)sulfonyl-2-(1-naphthylmethyl)propionyl]norleucine as white powder.

Rf value: 0.45(chloroform/methanol=5/1)

(b) 31.5 mg of the compound obtained in Example 41(3a) was treated in the same manner as in Example 1(9) to obtain 36.9 mg of the above-identified compound as white powder.

Rf value: 0.50 (chloroform/methanol=10/1) Mass spectrum (FAB) m/z 803(M+1)+ NMR (300 MHz, CDCl$_3$) δ ppm : 0.80~1.79(22H,m),1.99(1.5H,s), 2.00(1.5H,s),2.42~2.83(6H,m), 3.00~3.76(12H,m),3.81(1.5H,s), 3.87(1.5H,s),3.90~4.30(7H,m), 4.59(1H,brs),4.69~4.91(2H,m), 5.80~5.99(2H,m),7.32~7.63(4H,m), 7.79(1H,d,J=8 Hz),7.89(1H,d,J=8.01 Hz),8.01(1H,m)

EXAMPLE 42

(2S,3R,4S)-4-{L-N-[(2S)-3-(3-acetoxy-2-hydroxyiminopropyl)sulfonyl-2-(1-naphthylmethyl)propionyl]norleucyl}amino-5-cyclohexyl-1-morpholino-2,3-pentanediol (a) 124.3 mg of the compound obtained in Example 41(1) was dissolved in 2 ml of methanol, and 0.44 ml of a 1M potassium hydroxide methanol/water (9/1) solution of 30.5 mg of hydroxylamine was added thereto. The mixture was stirred at room temperature overnight. The reaction solution was diluted with ethyl acetate, washed with water and with a saturated sodium chloride aqueous solution and dried over anhydrous magnesium sulfate. Then, the solvent was distilled off under reduced pressure, and the residue was purified by silica gel column chromatography to obtain 14.3 mg of L-N-[(2S)-3-(3-acetoxy-2-hydroxyiminopropyl)thio-2-(1-naphthylmethyl)propionyl]norleucine benzyl ester as colorless oily substance.

Rf value: 0.25 (n-hexane/ethyl acetate=2/1)

(b) The compound obtained in Example 42(a) was treated in the same manner as in Example 41(2b)-(3) to obtain the above-identified compound as white powder.

Rf value: 0.44 (chloroform/methanol=10/1) Mass spectrum (FAB) m/z 789(M+1)+ NMR (300 MHz, CDCl$_3$) δ ppm : 0.75~1.90(22H,m),2.09(1.5H,s), 2.12(1.5H,s ),2.44~2.85(6H,m), 3.12~3.80(12H,m),3.89~4.40(3H,m), 4.37~4.99(2H,m),5.18(0.5H,brs), 6.39(0.5H,d,J=7 Hz),6.46(0.5H, brs),7.32~7.61(4H,m),7.26~7.91(2H,m),8.04(0.5H,d,J-=8 Hz),8.11(0.5H,d,J=8 Hz)

EXAMPLE 43

(2S,3R,4S)-4-{L-N-[(2S)-3-[(2RS)-3-acetoxy-2-ethoxypropyl]sulfonyl-2-(1-naphthylmethyl)propionyl]norleucyl}amino-5-cyclohexyl-1-morpholino-2,3-pentanediol (a) The same treatment was conducted in the same manner as in Example 27(1c) except that ethanol was used instead of methanol to obtain L-N-[(2S)-3-[(2RS)-2-ethoxy-3-hydroxypropyl]thio-2-(1-naphthylmethyl)-propionyl]norleucine tert-butyl ester.

Rf value: 0.42, 0.48 (n-hexane/ethyl acetate=1/1)

(b) 38 mg of the compound obtained in Example 43(a) was acetylated in the same manner as in Example 1(7c), followed by subjecting to the same treatment as in Example 1(8b)-(9) to obtain 38 mg of the above-identified compound as white powder.

Rf value: 0.29 (chloroform/methanol=20/1) Mass spectrum (FAB) m/z 804(M+1)+

EXAMPLE 44

(2S,3R,4S)-4-{L,N-[(2S)-3-[(2RS)-3-acetoxy-2- methoxypropyl]sulfonyl-2-(1-naphthylmethyl)propionyl]-(4-thiazolyl)alanyl}amino-5-cyclohexyl-1-morpholino-2,3-pentanediol (1) (2S)-3-[(2RS)-3-acetoxy-2-methoxypropyl]sulfonyl-2-(1-naphthylmethyl)propionic acid 700 mg of the compound obtained in Example 1(5) was dissolved in 10 ml of DMF, and 512 mg of sodium hydrogencarbonate and 1.8 ml of benzyl bromide were added thereto. The mixture was stirred at room temperature for 2 days. Water was added to the reaction solution, and the mixture was extracted with ethyl acetate. The ethyl acetate layer was washed with water and with a saturated sodium chloride aqueous solution and then dried over anhydrous magnesium sulfate. The solvent was distilled off under reduced pressure, and the residue was purified by silica gel column chromatography (n-hexane/ethyl acetate=10/1, 5/1 and 2/1) to obtain 558 mg of benzyl (2S)-3-hydroxy-2-(1-naphthylmethyl)propionate from the third fraction as colorless oily substance. Further, 270 mg of a O-formyl benzyl ester was obtained from the second fraction as colorless oily substance. The benzyl (2S)-3-hydroxy-2-(1-naphthylmethyl)propionate thereby obtained was derived to benzyl (2S)-3-[(2RS)-3-acetoxy-2 -methoxypropyl]sulfonyl-2-(1-naphthylmethyl)propionate by the method described in Example 29.

204 mg of the benzyl ester compound thereby obtained was dissolved in 10 ml of ethanol, and the hydrogenation was conducted at room temperature under an atmospheric pressure for 2 hours by an addition of palladium black to obtain 185 mg of the above-identified compound as colorless oily substance.

Rf value: 0.23 (benzene/methanol/acetic acid=10/1/0.05)

(2) L-(4-thiazolyl)alanine benzyl ester di-p-toluenesulfonate (a) 25 g of formamide was suspended in 250 ml of THF keeping the temperature below 30° C., 25 g of phosphorus pentasulfide was added thereto. The mixture was stirred at room temperature for 6 hours. Insolubles were removed by filtration, and then the filtrate was concentrated under reduced pressure. The residue was washed with petroleum ether. 15 g of the crude thioformamide thereby obtained was dissolved in 250 ml of acetone, and this solution was dropwise added to 100 ml of an acetone solution of 25 g of 1,3-dichloroacetone at room temperature. The mixture was stirred at room temperature for 5 days. Then, precipitates were collected by filtration and purified by sublimation (1-2 mmHg, 140°-150° C. in oil bath) to obtain 14.5 g of 4-chloromethylthiazole hydrochloride having a melting point of from 148° to 151° C. as slightly yellow prism. 21.7 g of diethyl acetamidemalonate was added to an ethoxide solution prepared from 2.3 g of sodium metal and 200 ml of dry ethanol and stirred at room temperature until a transparent solution was obtained. To this solution, 8.5 g of 4-chloromethylthiazole hydrochloride previously obtained was added, and the mixture was stirred at room temperature for 5 days and further at 40° C. for 2 days. The filtration was conducted by using a pad of celite and activated carbon, and the filtrate was concentrated under reduced pressure. The residue was recrystallized from hot water to obtain 9.6 g of diethyl (4-thiazolyl)methylacetamidemalonate as colorless needle-like crystals.

Rf value: 0.22 (n-hexane/ethyl acetate=1/1) Melting point: 104°-105° C.

(b) 9.1 g of the compound obtained in Example 44(2a) was dissolved in 50.7 ml of a 2N sodium hydroxide aqueous solution, and the solution was heated at 90° C. for 2 hours. 51 ml of 2N hydrochloric acid was added to the reaction solution, and the mixture was refluxed under heating for 1 hour and then left to stand until the temperature was cooled to room temperature. To the reaction solution, 750 ml of a 0.1M phosphoric acid buffer solution, 3 ml of concentrated aqueous ammonia and 100 ml of an L-amino acylase $S_2$ solution (180 μ/ml disclosed in Japanese Unexamined Patent Publication No. 101,042/1986) were added, and the incuvation was conducted at 37° C. for 39 hours. The reaction solution was applied to a Dowex-50(H+) column having a volume of 800 ml, washed with water and then eluted with 2N aqueous ammonia. Then, the eluted portion was applied to a Dowex-50(pyridine type) column having a volume of 200 ml. The passing portion wag further applied to a Dowex WGR (OH−) column having a volume of 200 ml and washed with water. The passing portion and the washing portion were put together and concentrated under reduced pressure to dryness to obtain 2.9 g of crude L-(4-thiazolyl)alanine as colorless powder.

1 g of the crude L-(4-thiazolyl)alanine, 2.4 g of p-toluenesulfonic acid and 3 ml of benzyl alcohol were suspended in 6 ml of benzene, and the suspension was refluxed under heating for 4 hours. The reaction solution was left to stand until it was cooled. Then, precipitated crystals were collected by filtration and recrystallized from benzene to obtain 2.0 g of the above-identified compound as colorless needle-like crystals.

Rf value: 0.73 (chloroform/methanol/33% acetic acid=6/3/1) Melting point: 118°-121° C.

(3) (2S,3R,4S)-4-{L-N-[(2S)-3-[(2RS)-3-acetoxy-2-methoxypropyl]sulfonyl-2-(1-naphthylmethyl)propionyl]-(4-thiazolyl)alanyl}amino-5-cyclohexyl-1-morpholino-2,3-pentanediol (a) 179 mg of the compound obtained in Example 44(1) and 294 mg of the compound obtained in Example 44(2) were dissolved in 3 ml of DMF, and 114 μl of DPPA and 208 μl of triethylamine were successively dropwise added thereto under cooling with ice. The mixture was stirred at room temperature overnight, and then water was added to the reaction solution. The mixture was extracted with ethyl acetate. The ethyl acetate layer was washed with a 4% sodium hydrogencarbonate aqueous solution, with water and with a saturated sodium chloride aqueous solution and dried over anhydrous magnesium sulfate. The solvent was distilled off under reduced pressure, and the residue was purified by silica gel column chromatography (n-hexane/ethyl acetate=2/1 and 1/2) to obtain 103 mg of L-N-{(2S)-3-[(2RS)-3-acetoxy-2-methoxypropyl]sulfonyl-2-(1-naphthylmethylpropionyl}-(4-thiazolyl)alanine benzyl ester from the second fraction as colorless powder.

Rf value: 0.16, 0.23 (n-hexane/ethyl acetate=1/1)

(b) 100 mg of the compound obtained in Example 44(3a) was dissolved in 3 ml of ethanol, and the hydrogenation was conducted at room temperature under an atmospheric pressure overnight by an addition of palladium black. The catalyst was removed by filtration, and then the filtrate was concentrated under reduced pressure to obtain a carboxylic acid.

The carboxylic acid thereby obtained was dissolved in 2 ml of DMF and treated in the same manner as in Example 1(9) to obtain 56 mg of the above-identified compound as colorless powder.

Rf value: 0.31 (chloroform/methanol=20/1) Mass spectrum (FAB) m/z 831(M+1)+

EXAMPLE 45

(2R)-2-benzyl-3-hydroxypropionic acid (a) 5 g of diethyl benzylmalonate was dissolved in a mixture of 120 ml of ethanol and 80 ml of THF, and 3.8 g of sodium borohydride and 4.3 g of lithium chloride were added thereto under cooling with ice. The mixture was stirred at room temperature for 2 hours. Then, 5.8 ml of acetic acid was added thereto, and the solvent was distilled off under reduced pressure. Water and ethyl acetate were added to the residue. The ethyl acetate layer was separated, washed with water and with a saturated sodium chloride aqueous solution and then dried over anhydrous magnesium sulfate. The solvent was distilled off under reduced pressure to obtain 3.5 g of 2-benzyl-1,3-propanediol as colorless solid.

Rf value: 0.17(n-hexane/ethyl acetate=1/1)

(b) 20 g of the compound obtained in Example 45(a) was suspended in 50 ml of vinyl acetate, and 3 g of Lipase P (manufactured by Amano Seiyaku) was added thereto. The mixture was stirred at room temperature for 3 hours. The Lipase was removed by filtration, and then the filtrate was condensed under reduced pressure. The residue was purified by silica gel column chromatography (n-hexane/ethyl acetate=2/1) to obtain 25.6 g of (2R)-2-benzyl-1,3-propanediol-1-acetate as colorless oily substance.

Angle of rotation:$[\alpha]_D^{20}$ = +28.6° (C 1.07, CHCl$_3$)

Rf value: 0.29 (n-hexane/ethyl acetate=2/1)

(c) 28 g of the compound obtained in Example 45(b) was dissolved in 100 ml of dichloromethane, and 56.5 ml of diisopropylethylamine was added thereto. 24.6 ml of chloromethyl methyl ether in 20 ml of a dichloromethane solution was dropwise added thereto under cooling with ice. The mixture was stirred at room temperature overnight. Ethyl acetate was added to the reaction solution, the ethyl acetate layer was washed sequentially with water, with 1N hydrochloric acid, with a 4% sodium hydrogencarbonate aqueous solution, with water and with a saturated sodium chloride aqueous solution and dried over anhydrous magnesium sulfate. Then, the solvent was distilled off under reduced pressure. The residue was dissolved in 300 ml of methanol, and 230 ml of a 1.1M potassium carbonate aqueous solution was added thereto. The mixture was stirred at room temperature for 1.5 hours. Methanol was distilled off under reduced pressure. The residue was extracted with ethyl acetate. The ethyl acetate layer was washed with water and with a saturated sodium chloride aqueous solution, then dried over anhydrous magnesium sulfate and concentrated under reduced pressure. The residue was purified by silica gel column chromatography (n-hexane/ethyl acetate=2/1) to obtain 26.9 g of (2S)-2-benzyl-1-O-methoxymethyl-1,3-propanediol as colorless oily substance.

Angle of rotation:$[\alpha]_D^{20}$ = −18.1° (C 1.0, CHCl$_3$) Rf value: 0.32 (n-hexane/ethyl acetate=2/1)

(d) 26.8 g of the compound obtained in Example 45(c) was dissolved in 500 ml of acetone, and 57 ml of Jones reagent which was prepared by dissolving 26.7 g of chromium trioxide in 23 ml of concentrated sulfuric acid-40 ml of water, followed by bringing it to 100 ml with water, was dropwise added thereto under cooling with ice. The mixture was stirred at the same temperature for 2 hours. Excessive amount of Jones reagent was decomposed with isopropyl alcohol, and then the solvent was distilled off under reduced pressure. The residue was dissolved in 300 ml of THF, and 300 ml of 6N hydrochloric acid was added thereto. The mixture was heated at a temperature of from 50° to 55° C. for 1.5 hours. THF was distilled off under reduced pressure, and the residue was extracted with ethyl acetate. The organic layer was extracted with a saturated sodium hydrogencarbonate aqueous solution. The aqueous layer was adjusted to pH2 with 6N hydrochloric acid and then extracted with ethyl acetate. The extract layer was washed with water and with a saturated sodium chloride aqueous solution and then dried over anhydrous magnesium sulfate. The solvent was distilled off under reduced pressure. The residue was recrystallized from diethyl ether-n-hexane to obtain 15.7 g of the above-identified compound as colorless needles.

The product was subjected to coupling with norleucine tert-butyl ester and analyzed by an HPLC analysis. The product has at least 98% of excess ratio of enantiomer.

Melting point: 67.5°–68.5° C. Angle of rotation:- $[\alpha]_D^{20} = +13.9°$ (C 0.97, CHCl$_3$) Rf value: 0.14 (benzene/methanol/acetic acid = 10/1/0.1)

EXAMPLE 46

(2R)-3-hydroxy-2-(1-naphthylmethyl)propionic acid (a) 2 g of 1-naphthoaldehyde, 2.3 g of diethyl malonate and 0.2 ml of piperidine were dissolved in 10 ml of benzene, and the solution was refluxed under heating for 6 hours while removing water by azeotropic distillation. The reaction solution was diluted with benzene, washed sequentially with 1N hydrochloric acid, with a saturated sodium hydrogencarbonate aqueous solution, with water and with a saturated sodium chloride aqueous solution and dried over anhydrous magnesium sulfate. Then, the solvent was distilled off under reduced pressure. The residue was dissolved in a mixture consisting of 55 ml of ethanol and 37 ml of THF, and 2.7 g of sodium borohydride and 3.0 g of lithium chloride were added thereto under cooling with ice. The mixture was stirred at room temperature for 1 hour and then concentrated under reduced pressure. Water was added to the residue, and the solution was neutralized with 6N hydrochloric acid and extracted with ethyl acetate. The extract layer was washed with a saturated sodium hydrogencarbonate aqueous solution, with water and with a saturated sodium chloride aqueous solution and dried over anhydrous magnesium sulfate. Then, solvent was distilled off under reduced pressure. The residue was recrystallized from diethyl ether-n-hexane to obtain 2.5 g of 2-(1-naphthylmethyl)-1,3-propanediol.

Rf value: 0.17 (n-hexane/ethyl acetate=2/1)

(b) The compound obtained in Example 46(a) was treated in the same manner as in Example 45(b)–(d) to obtain the above-identified compound.

The product was subjected to coupling with norleucine tert-butyl ester and then analyzed by an HPLC analysis. The product has at least 96% enantio excess.

Melting point: 116.5°–118.0° C. (slightly brown powder, benzene) Angle of rotation:$[\alpha]_D^{20} = +33.1°$ (C 0.98, CHCl$_3$)

Rf value: 0.33 (benzene/methanol/acetic acid=8/1/0.1)

EXAMPLE 47

(2R)-2-benzyl-3-hydroxypropionic acid (another method)

(a) 3.5 g of the compound obtained in Example 45(a) was dissolved in 9.8 ml of triethylamine, and 1.2 g of 4-dimethylaminopyridine was added thereto. 6.2 g of acetic anhydride was dropwise added thereto under cooling with ice, and the mixture was stirred at room temperature for 1 hour. The reaction solution was diluted with diethyl ether, washed with 2N hydrochloric acid, with a saturated sodium hydrogencarbonate aqueous solution, with water and with a saturated sodium chloride aqueous solution and dried over anhydrous magnesium sulfate. Then, the solvent was distilled off under reduced pressure. The residue was purified by silica gel column chromatography (n-hexane/ethyl acetate=4/1) to obtain 5.0 g of 2-benzyl-1,3-diacetoxypropane as colorless oily substance.

Rf value: 0.42 (n-hexane/ethyl acetate=4/1)

(b) 2 g of the compound obtained in Example 47(a) was dissolved in 75 ml of acetone, and 175 ml of a 0.1M phosphate buffer (pH7.0) was added thereto. 1 g of Lipase P (manufactured by Amano Seiyaku) was added thereto, and the mixture was-stirred at 30° C. for 2 days. Acetone was distilled off under reduced pressure, and sodium chloride was added to the residue until it became a saturated state. The mixture was extracted with ethyl acetate, and the extract layer was washed with water and with a saturated sodium chloride aqueous solution. The solvent was distilled off under reduced pressure, and then the residue was purified by silica gel column chromatography (n-hexane/ethyl acetate=5/1, 2/1) to obtain 594 mg of (2S)-2-benzyl-1,3-propanediol-1-acetate as colorless oily substance from the second fraction.

Angle of rotation:$[\alpha]_D^{20} = -28.1°$ (C 1.01, CHCl$_3$)
Rf value: 0.29 (n-hexane/ethyl acetate=2/1)

(c) 590 mg of the compound obtained in Example 47(b) was dissolved in 10 ml of acetone, and 1.2 ml of Jones reagent was added thereto under cooling with ice. The mixture was stirred at room temperature for 1 hour. Then, an excessive amount of Jones reagent was decomposed with diisopropyl alcohol, and the solvent was distilled off under reduced pressure. The residue was dissolved in ethyl acetate, the ethyl acetate layer was washed with water and with a saturated sodium chloride aqueous solution and dried over anhydrous magnesium sulfate. The solvent was distilled off under reduced pressure, and the residue was dissolved in 10 ml of methanol. Then, 8 ml of a 1M potassium carbonate aqueous solution was added thereto, and the mixture was stirred at room temperature overnight. Methanol was distilled off under reduced pressure, and then the residue was extracted with diethyl ether. The aqueous layer was adjusted to pH2 with 1N hydrochloric acid and extracted with ethyl acetate. Then, the extract layer was washed with water and with a saturated sodium chloride aqueous solution and dried over anhydrous magnesium sulfate. Then, the solvent was distilled off under reduced pressure, and the residue was recrystallized from diethyl ether-n-hexane to obtain 305 mg of the above-identified compound as colorless needles.

EXAMPLE 48

(2S,3R,4S)-4-{L-N-[(2S)-3-(3-acetoxy-2,2-diethoxy-propyl)sulfonyl-2-(1-naphthylmethyl)propionyl]norleucyl}amino-5-cyclohexyl-1-morpholino-2,3-pentanediol (a) 53.4 mg of the compound obtained in Example 41(1) was dissolved in 1.0 ml of ethyl orthoformate, and 5 mg of anhydrous p-toluenesulfonic acid was added thereto. The mixture was stirred at room temperature overnight. The reaction solution was diluted with ethyl acetate, washed sequentially with a saturated sodium hydrogencarbonate aqueous solution, with water and with a saturated sodium chloride aqueous solution and dried over anhydrous magnesium sulfate. Then, the solvent was distilled off under reduced pressure, and the residue was purified by silica gel column chromatography to obtain 44.1 mg of L-N-[(2S)-3-(3-acetoxy-2,2-diethoxypropyl)thio-2-(1-naphthylmethyl)propionyl]-norleucine benzyl ester as colorless oily substance.

Rf value: 0.55 (n-hexane/ethyl acetate=2/1)

(b) The compound obtained in Example 48(a) was treated in the same manner as in Example 41(2b)-(3) to obtain the above-identified compound as white solid.

Rf value: 0.55 (chloroform/methanol=10/1) Mass spectrum (FAB) m/z 848(M+1)+ NMR (300 MHz, CDCl$_3$) δ ppm : 0.80~1.85(22H,m),2.07(3H,s),2.41~2.96(7H,m),3.10~3.81(13H,m), 4.18~4.41(5H,m),5.94(1H,d,J=6 Hz), 6.00(1H,d,J=9 Hz),7.31~7.62(4H,m), 7.79(1H,d,J=8 Hz),7.89(1H,d,J=8 Hz),8.02(1H,d,J=8 Hz)

EXAMPLE 49

(2 R,3R,4S)-4-{(2S)-3-[2-(3-hydroxymethyl) pyridylthio]-2-(1-naphthylmethyl)propionyl}histidyl}amino-5-cyclohexyl-1-morpholino-2,3-pentanediol
(a) (2S,3R,4S)-4-{L-N-{(2S)-3-[2-(3-hydroxymethyl) pyridylthio]-2-(1-naphthylmethyl)propionyl}-N$^{im}$-tritylhistidyl}amino-5-cyclohexyl-1-morpholino-2,3-pentanediol 300 mg of L-N-[(2R)-3-(p-toluenesulfonyl)oxy-2-(1-naphthylmethyl)propionyl]-N$^{im}$-tritylhistidine methyl ester was treated in the same manner as in Example 1(7b) except that 109 mg of 3-hydroxymethyl-2-mercaptopyridine was used instead of o-thioglycerol and then hydrolyzed by potassium hydroxide, to obtain a carboxylic acid compound.

Then, the carboxylic acid compound was condensed with (2S,3R,4S)-4-amino-5-cyclohexyl-1-morpholino-2,3-pentanediol dihydrochloride by using DCC in the same manner as in Example 1(6). The product thereby obtained was purified by silica gel column chromatography to obtain 188 mg of the above-identified compound as white solid.

Rf value: 0.24 (chloroform/methanol=20/1)

(b) 188 mg of the compound obtained in Example 49(a) was dissolved in dry pyridine, acetylated by using acetyl chloride and then, treated with trifluoroacetic acid in the presence of anisole. Then, the product thereby obtained was purified by silica gel column chromatography to obtain 28 mg of the above identified compound as white solid.

Rf value: 0.17 (chloroform/methanol/triethylamine=20/2/0.1) Mass spectrum (FAB) m/z 801(M+1)+ NMR (300 MHz, CDCl$_3$) δ ppm : 0.75~1.00(2H,m),1.00~1.85(11H,m), 2.18(3H,s),2.40~2.98(7H,m),3.00~3.27(2H,m),3.35~3.57(4H,m),3.57~3.80(6H,m),4.22(1H,m),4.39(1H,m) 4.92(1H,d,J=13.8 Hz),5.08(1H,d,J=13.8 Hz),6.11(1H,d,J=9.3 Hz),6.85~7.03(3H,m),7.31~7.58(6H,m),7.73(1H,m),7.87(1H,m),8.10(1H,m), 8.19(1H,m),9.64(1H,brs)

The compounds of the present invention have strong renin-inhibiting activities against a renin-angiotensin hypertensive system and thus expected to be useful as curing agents of hypertension due to the progress of the renin-angiotensin system.

We claim:
1. An N-substituted acylamino acid compound of the formula:

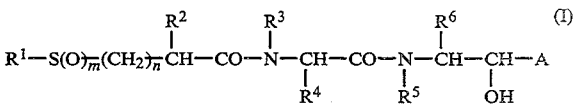

wherein R$^1$ is,
a) C$_{1-6}$ alkyl,
b) C$_{3-7}$ cycloalkyl,
c) C$_{4-10}$ cycloalkylalkyl,
d) tetrahydrofuranyl,
e) tetrahydrofuranyl C$_{1-6}$ alkyl,
f) tetrahydropyranyl,
g) tetrahydropyranyl C$_{1-6}$ alkyl,
h) C$_{6-10}$ aryl,
i) C$_{7-15}$ aralkyl wherein these substituents are substituted by 1 to 3 substituents selected from the group consisting of C$_{1-5}$ alkanoyloxy and C$_{2-5}$ alkoxycarbonyloxy, and may further be substituted by 1 to 3 substituents selected from the group consisting of hydroxyl and C$_{1-3}$ alkoxy, =N—OY$^1$ (wherein Y$^1$ is hydrogen, C$_{1-4}$ alkyl which may be substituted by carboxyl, or C$_{1-4}$ alkyl substituted by C$_{2-5}$ alkoxycarbonyl),

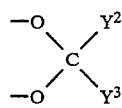

(wherein each of Y$^2$ and Y$^3$ which may be the same or different is hydrogen, C$_{1-4}$ alkyl or phenyl, or Y$^2$ and Y$^3$ together with the adjacent carbon atom form cyclohexylidene or oxo), or

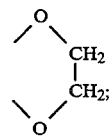

R$^2$ is C$_{7-15}$ aralkyl;
R$^4$ is C$_{1-6}$ alkyl which may be substituted by pyrolyl, furyl, thienyl, pyridyl, imidazolyl, pyrazolyl, thiazoyl, isothiazolyl, isoxazolyl, oxazolyl, pyrazinyl, pyrimidinyl, pyridazinyl;
R$^6$ is C$_{1-4}$ alkyl or C$_{4-10}$ cycloalkylalkyl;
each of R$^3$ and R$^5$ which may be the same or different is hydrogen or C$_{1-6}$ alkyl;
A is
i) —CH(OH)—(CH$_2$)$_q$—R$^7$ wherein R$^7$ is C$_{1-6}$ alkyl C$_{3-7}$ cycloalkyl, imidazolidinyl, 2-imidazolinyl, morpholinyl, piperazinyl, piperidinyl, thiomorpholinyl, morpholine-N-oxide, N-alkylmorpholino or C$_{1-6}$ alkyl-S(O)$_i$(wherein i is 0, 1 or 2),
q is 0, 1 or 2;
m is 0, 1 or 2;
and n is an integer of from 1 to 5;
or a salt thereof.

2. The N-substituted acylamino acid compound according to claim 1, which is (2S,3R,4S)-4-{L-N-[(2S)-3-[(2RS)-2,3-diacetoxypropyl]sulfonyl-2-(1-naphthylmethyl)propionyl]norleucyl}amino-5-cyclohexyl-1-morpholino-2,3-pentanediol, (2S,3R,4S)-4-{L-N-[(2S)-3-[(2RS)-3-pivaloyloxy- 2-hydroxypropyl]sulfonyl-2-(1-naphthylmethyl)propionyl]norleucyl}amino-5-cyclohexyl-1-morpholino-2,3-pentanediol, (2S,3R,4S)-4-{L-N-[(2S)-3-[(2-acetoxyethyl)sulfonyl-2-(1-naphthylmethyl)propionyl]norleucyl}amino-5-cyclohexyl-1-morpholino-2,3-pentanediol, (2S,3R,4S)-4-{L-N-[(2S)-3-(2-pivaloyloxyethyl)sulfonyl-2-(1-naphthylmethyl)propionyl]norleucyl}amino-5-cyclohexyl1-morpholino-2,3-pentanediol, (2S,3R,4S)-4-{L-N-[(2S)-3-(2-ethoxycarbonyloxyethyl)sulfonyl-2-(1-naphthylmethyl)propionyl]norleucyl}amino-5-cyclohexyl-1-morpholino-2,3-pentanediol, (2S,3R,4S)-4-{L-N-[(2S)-3-[(2RS)-2,3-diacetoxypropyl]sulfinyl-2-(1-naphthylmethyl)propionyl]norleucyl}amino-5-cyclohexyl-1-morpholino-2,3-pentanediol, (2S,3R,4S)-4-{L-N-[(2S)-3-[(2RS)-2,3-diacetoxypropyl]thio-2-(1-naphthylmethyl)-propionyl]norleucyl}amino-5-cyclohexyl-1-morpholino-2,3-pentanediol, (2S,3R,4S)-4-{L-N-[(2S)-3-[(2RS)-2,3-dipropionyloxypropyl]sulfonyl-2-(1-naphthylmethyl)propionyl]norleucyl}amino-5-cyclohexyl-1-morpholino-2,3-pentanediol, (2S,3R,4S)-4-{L-N-[(2S)-3-[(2RS)-3-acetoxy-2-hydroxypropyl]sulfonyl-2-(1-naphthylmethyl)propionyl]norleucyl}amino-5-cyclohexyl-1-morpholino-2,3-pentanediol, (2S,3R,4S)-4-{L-N-[(2S)-3-[(2RS)-3-propionyloxy-2-hydroxypropyl]sulfonyl-2-(1-naphthylmethyl)propionyl]norleucyl}amino-5-cyclohexyl-1-morpholino-2,3-pentanediol, (2S,3R,4S)-4-{L-N-[(2S)-3-[(2RS)-2-acetoxy-3-propionyloxypropyl]sulfonyl-2-(1-naphthylmethyl)propionyl]norleucyl}amino-5-cyclohexyl-1-morpholino-2,3-pentanediol, (2S,3R,4S)-4-{L-N-[(2S)-3-[(2RS)-2-methoxy-3-propionyloxypropyl]sulfonyl-2-(1-naphthylmethyl)propionyl]norleucyl}amino-5-cyclohexyl-1-morpholino-2,3-pentanediol, (2S,3R,4S)-4-[L-N-[(2S)-3-[(2RS)-2,3-diacetoxypropyl]sulfonyl-2-benzylpropionyl]norleucyl}amino-5-cyclohexyl-1-morpholino-2,3-pentanediol, (2S,3R,4S)-4-{L-N-[(2S)-3-[(2RS)-2,3-diacetoxypropyl]thio-2-benzylpropionyl]-norleucyl}amino-5-cyclohexyl-1-morpholino-2,3-pentanediol, (2S,3R,4S)-4-{L-N-[(2S)-3-[(2RS)-2,3-dipropionyloxypropyl]sulfonyl-2-benzylpropionyl]norleucyl}amino-5-cyclohexyl-1-morpholino-2,3-pentanediol, (2S,3R,4S)-4-{L-N-[(2S)-3-(4-acetoxyphenylthio)-2-(1-naphthylmethyl)propionyl]norleucyl}amino-5-cyclohexyl-1-morpholino-2,3-pentanediol, (2S,3R,4S)-4-{L-N-[(2S)-3-(4-acetoxyphenylsulfonyl)-2-(1-naphthylmethyl)propionyl]norleucyl}amino-5-cyclohexyl-1-morpholino-2,3-pentanediol, (2S,3R,4S)-4-{L-N-[(2S)-3-(4-acetoxyphenylsulfinyl)-2-(1-naphthylmethyl)propionyl]norleucyl}amino-5-cyclohexyl-1-morpholino-2,3-pentanediol, (2S,3R,4S)-4-{L-N-[(2S)-3-[(2RS)-2,3-diacetoxypropyl]sulfonyl-2-(1-naphthylmethyl)propionyl]histidyl}amino-5-cyclohexyl-1-morpholino-2,3-pentanediol, (2 R,3R,4S)-4-{L-N-[(2S)-3-[(2RS)-2,3-diacetoxypropyl]sulfonyl-2-(1-naphthylmethyl)propionyl]norleucyl}amino-1-isopropylthio-6-methyl-2,3-heptanediol, (2 R,3R,4S)-4-{L-N-[(2S)-3-[(2RS)-2,3-diacetoxypropyl]sulfonyl-2-(1-naphthylmethyl)propionyl]norleucyl}amino-1-isopropylsulfonyl-6-methyl-2,3-heptanediol, (2S,3R,4S)-4-{L-N-[(2S)-3-[(2RS)-3-acetoxy-2-methoxypropyl]thio-2-(1-naphthylmethyl)propionyl]norleucyl}amino-5-cyclohexyl-1-morpholino-2,3-pentanediol, (2S,3R,4S)-4-{L-N-[(2S)-3-[(2RS)-2-acetoxy-2-methoxypropyl]sulfonyl-2-(1-naphthylmethyl)propionyl]norleucyl}amino-5-cyclohexyl-1-morpholino-2,3-pentanediol, (2S,3R,4S)-4-{L-N-[(2S)-3-[(2RS)-3-acetoxy-2-methoxypropyl]sulfonyl-2-(1-naphthylmethyl)propionyl]norleucyl}amino-5-cyclohexyl-1-morpholino-2,3-pentanediol, (2S,3R,4S)-4-{L-N<sup>α</sup>-[(2S)-3-(2-acetoxyethyl)sulfonyl-2-(1-naphthylmethyl)propionyl]histidyl}amino-5-cyclohexyl-1-morpholino-2,3-pentanediol, (2S,3R,4S)-4-{L-N<sup>α</sup>-[(2S)-3-(2-acetoxyethyl)thio-2-(1-naphthylmethyl)propionyl]histidyl}amino-5-cyclohexyl-1-morpholino-2,3-pentanediol, (2S,3R,4S)-4-{L-N-[(2S)-3-(3-acetoxycyclopentyl)sulfonyl-2-(1-naphthylmethyl)propionyl]norleucyl}amino-5-cyclohexyl-1-morpholino-2,3-pentanediol, (2S,3R,4S)-4-{L-N-[(2S)-3-(3-acetoxycyclopentyl)thio-2-(1-naphthylmethyl)propionyl]norleucyl}amino-5-cyclohexyl-1-morpholino-2,3-pentanediol, (2S,3R,4S)-4-{L-N-[(2S)-3-(2-acetoxycyclopentyl)sulfonyl-2-(1-naphthylmethyl)propionyl]norleucyl}amino-5-cyclohexyl-1-morpholino-2,3-pentanediol, (2S,3R,4S)-4-{L-N-[(2S)-3-(2,3-diacetoxycyclopentyl)sulfonyl-2-(1-naphthylmethyl)propionyl]norleucyl}amino-5-cyclohexyl-1-morpholino-2,3-pentanediol, (2S,3R,4S)-4-{L-N-[(2S)-3-(2,5-diacetoxycyclopentyl)sulfonyl-2-(1-naphthylmethyl)propionyl]norleucyl}amino-5-cyclohexyl-1-morpholino-2,3-pentanediol, (2S,3R,4S)-4-{L-N-[(2S)-3-(3-O-acetyl-5-deoxy-1,2-O-isopropyliden-α-D-ribofuranose-5-yl)sulfonyl-2-benzylpropionyl]norleucyl}amino-5-cyclohexyl-1-morpholino-2,3-pentanediol, (2S,3R,4S)-4-{L-N-[(2S)-3-[(2 R(or S))-3-acetoxy-2-methoxypropyl]sulfonyl-2-(1-naphthylmethyl)propionyl]norleucyl}amino-5-cyclohexyl-1-morpholino-2,3-pentanediol, (2S,3R,4S)-4-{L-N-[(2S)-3-[(2S(or R))-3-acetoxy-2-methoxypropyl]sulfonyl-2-(1-naphthylmethyl)propionyl]norleucyl}amino-5-cyclohexyl-1-morpholino-2,3-pentanediol, (2S,3R,4 S )-4-{L-N-[(2 S )-3-(3-acetoxy-2-methoxyiminopropyl)sulfonyl-2-(1-naphthylmethyl)propionyl]norleucyl}amino-5-cyclohexyl-1-morpholino-2,3-pentanediol, (2S,3R,4S)-4-{L-N-[(2S)-3-(3-acetoxy-2-hydroxyiminopropyl)sulfonyl-2-(1-naphthylmethyl)propionyl]norleucyl}amino-5-cyclohexyl-1-morpholino-2,3-pentanediol, (2S,3R,4S)-4-{L-N-[(2S)-3-[(2RS)-3-acetoxy-2-ethoxypropyl]sulfonyl-2-(1-naphthylmethyl)propionyl]norleucyl}amino-5-cyclohexyl-1-morpholino-2,3-pentanediol, (2S,3R,4S)-4-{L-N-(2S)-3-[2-(3-hydroxymethyl)pyridylthio]-2-(1-naphthylmethyl)propionyl}histidinyl}amino-5-cyclohexyl-1-morpholino-2,3-pentanediol, (2S,3R,4S)-4-{L-N-[(2S)-3-[(2RS)-3-acetoxy-2-methoxypropyl]sulfonyl-2-(1-naphthylmethyl)propionyl]-(4-thiazolyl)alanyl}amino-5-cyclohexyl-1-morpholino-2,3-pentanediol or (2S,3R,4S)-4-{L-N-[(2S)-3-(3-acetoxy-2,2-diethoxypropyl)sulfonyl-2-(1-naphthylmethyl)propionyl]norleucyl}amino-5-cyclohexyl-1-morpholino-2,3-pentanediol; or a salt thereof.

3. The N-substituted acylamino acid compound according to claim 1, wherein A is

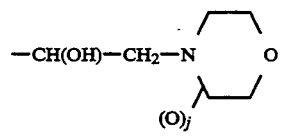

(wherein j is 0 or 1); or a salt thereof.

4. A hypotensive composition comprising an effective amount of an N-substituted acylamino acid compound of the formula I as defined in claim 1 or its pharmaceutically acceptable salt and a pharmaceutically acceptable carrier.

5. The N-substituted acylamino acid compound of claim 1, of the formula (2S,3R,4S)-4-{L-N-[(2RS)-2,3-diacetoxypropyl]sulfonyl-2-(1-naphthylmethyl)propionyl]norleucyl}amino-5-cyclohexyl-1-morpholino-2,3-pentanediol.

* * * * *

UNITED STATES PATENT AND TRADEMARK OFFICE
CERTIFICATE OF CORRECTION

PATENT NO. : 5,424,309
DATED : June 13, 1995
INVENTOR(S) : Hajime MORISHIMA, et al.

It is certified that error appears in the above-indentified patent and that said Letters Patent is hereby corrected as shown below:

On the title page, Item [75], the second inventor's name should read:

--Yutaka Koike--

Signed and Sealed this

First Day of August, 1995

Attest:

BRUCE LEHMAN

Attesting Officer   Commissioner of Patents and Trademarks